(12) United States Patent
Lee et al.

(10) Patent No.: US 9,783,859 B2
(45) Date of Patent: Oct. 10, 2017

(54) METHOD OF SCREENING AND QUANTIFYING VARIOUS ENZYMATIC ACTIVITIES USING ARTIFICIAL GENETIC CIRCUITS

(75) Inventors: Seung Goo Lee, Daejeon (KR); Eugene Rha, Daejeon (KR); Su Lim Choi, Daejeon (KR); Jae Jun Song, Daejeon (KR); Jong Hyun Choi, Daejeon (KR); Hee Sik Kim, Gyeonggi-do (KR)

(73) Assignee: KOREA RESEARCH INSTITUTE OF BIOSCIENCE AND BIOTECHNOLOGY, Deajeon (KR)

( * ) Notice: Subject to any disclaimer, the term of this patent is extended or adjusted under 35 U.S.C. 154(b) by 1439 days.

(21) Appl. No.: 13/376,783

(22) PCT Filed: Jun. 8, 2010

(86) PCT No.: PCT/KR2010/003674
§ 371 (c)(1),
(2), (4) Date: Apr. 25, 2012

(87) PCT Pub. No.: WO2010/143871
PCT Pub. Date: Dec. 16, 2010

(65) Prior Publication Data
US 2012/0238470 A1    Sep. 20, 2012

(30) Foreign Application Priority Data

Jun. 8, 2009    (KR) .................. 10-2009-0050596
Dec. 23, 2009   (KR) .................. 10-2009-0130204

(51) Int. Cl.
*C40B 30/00* (2006.01)
*C12Q 1/68* (2006.01)
*C12N 15/10* (2006.01)

(52) U.S. Cl.
CPC ....... *C12Q 1/6897* (2013.01); *C12N 15/1086* (2013.01)

(58) Field of Classification Search
CPC .......................... C12Q 1/6897; C12N 15/1086
See application file for complete search history.

(56) References Cited

U.S. PATENT DOCUMENTS 6,329,160 B1 * 12/2001 Schneider ............. C12Q 1/001
                                              435/189
6,773,918 B2    8/2004 Wise et al.
(Continued)

FOREIGN PATENT DOCUMENTS

KR    10-2004-0061588 A    7/2004
KR    10-0464068 B1        1/2005
(Continued)

OTHER PUBLICATIONS

Park et al., A new variant activator involved in the degradation of phenolic compounds from a strain of Pseudomonas putida, Journal of Biotechnology 103 (2003) 227_/236.*
(Continued)

*Primary Examiner* — Reza Ghafoorian
(74) *Attorney, Agent, or Firm* — Hultquist, PLLC; Steven J. Hultquist

(57) ABSTRACT

A method of detecting and quantifying various enzymatic activities using a constructed artificial genetic circuit GESS (genetic enzyme screening system) for sensing phenolic compounds and a method of screening a trace of activities of target enzymes from a metagenome using the artificial genetic circuit, thereby securing target enzyme genes. When the method for screening and quantifying target enzymatic activity is used, useful genes can be screened from various genetic communities, including environmental or metagenomic libraries, at a single cell level in high throughput (million/day). Further, the sensitivity of the genetic circuit to
(Continued)

phenol derivatives and the expression thereof can be controlled, and thus the genetic circuit can rapidly sense and quantify various enzymatic activities. Thus, the method can be advantageously used in the protein engineering technology for enzyme modification. Particularly, it can quantitatively investigate enzymatic activity, and thus can be applied to molecular evolution technology.

24 Claims, 24 Drawing Sheets

(56) References Cited

U.S. PATENT DOCUMENTS

| | | | |
|---|---|---|---|
| 6,803,224 | B2 | 10/2004 | Ramirez et al. |
| 6,806,076 | B1 | 10/2004 | Miyake et al. |
| 7,132,268 | B2 | 11/2006 | Miyake et al. |
| 7,208,298 | B2 | 4/2007 | Miyake et al. |
| 7,364,885 | B2 | 4/2008 | Miyake et al. |
| 7,531,333 | B2 | 5/2009 | Miyake et al. |
| 2005/0032169 | A1 | 2/2005 | Miyake et al. |
| 2007/0004000 | A1 | 1/2007 | Miyake et al. |
| 2007/0269857 | A1 | 11/2007 | Miyake et al. |
| 2008/0131926 | A1 | 6/2008 | Miyake et al. |
| 2008/0227141 | A1 | 9/2008 | Miyake et al. |

FOREIGN PATENT DOCUMENTS

| | | |
|---|---|---|
| KR | 10-0681815 B1 | 2/2007 |
| KR | 10-0724004 B1 | 6/2007 |
| KR | 10-0865216 B1 | 10/2008 |

OTHER PUBLICATIONS

Jean-Louis Reymond, Enzyme Assays, High-throughput Screening, Genetic Selection and Fingerprinting, (2006) a publication by WILEY-VCH Verlag GmbH & Co. KGaA, Weinheim, Germany, Printed in the Federal Republic of Germany, ISBN-13: 978-3-527-31095-1, ISBN-10: 3-527-31095-9.*
Recorbet et al., Conditional Suicide System of *Escherichia coli* Released into Soil That Uses the Bacillus subtilis sacB Gene, Applied and Environmental Microbiology, May 1993, p. 1361-1366.*
Siham Beggah et al., "Mutant HbpR transcription activator isolation for 2-chlorobiphenyl via green fluorescent protein-based flow cytometry and cell sorting", Microbial Biotechnology, 2008, pp. 68-78, vol. 1, No. 1.
Haoyuan Chen et al., "Binding of Phenol and Analogues to Alanine Complexes of Tyrosine Phenol-Lyase from *Citrobacter freundii*: Implications for the Mechanisms of α,β-Elimination and Alaine Racemization", Biochemistry, 1993, pp. 11591-11599, vol. 32.
Haoyuan Chen et al., "Site-directed mutagenesis of His343→Ala in *Citrobacter freundii* tyrosine phenol-lyase Effects on the kinetic mechanism and rate-determining step", Eur. J. Biochem., 1995, pp. 540-549, vol. 229.
T.V. Demidkina et al., "Crystallization and crystal data on tyrosine phenol-lyase", FEBS Letters, 1988, pp. 381-382, vol. 232, No. 2.
Jae-Seok Ha et al., "Design and Application of Highly Responsive Fluorescence Resonance Energy Transfer Biosensors for Detection of Sugar in Living *Saccharomyces cerevisiae* Cells", Applied and Environmental Microbiology, 2007, pp. 7408-7414, vol. 73, No. 22.

Jo Handelsman et al., "Molecular biological access to the chemistry of unknown soil microbes: a new frontier for natural products", Chemistry & Biology, 1998, pp. R245-R249, vo. 5, No. 10.
Dennis M. Kiick et al., Mechanistic Deductions from Kinetic Isotope Effects and pH Studies of Pyridoxal Phosphate Dependent Carbon-Carbon Lyases: *Erwinia herbicola* and *Citrobacter freundii* Tyrosine Phenol-Lyase, Biochemistry, 1988, pp. 7333-7338, vol. 27.
Seung-Goo Lee et al., "Inactivation of tyrosine phenol-lyase by Pictet-Spengler reaction and alleviation by T15A mutation on intertwined N-terminal arm", The FEBS Journal, 2006, pp. 5564-5572, vol. 273.
Martin Neuenschwander et al., "A simple selection strategy for evolving highly efficient enzymes", Nature Biotechnology, 2007, pp. 1145-1147, vol. 25, No. 10.
Lee Ching Ng et al., "Genetic Evidence for Interdomain Regulation of the Phenol-responsive $\sigma^{54}$-dependent Activator DmpR*", The Journal of Biological Chemistry, 1996, pp. 17281-17286, vol. 271, No. 29.
Hendrik Pavel et al., "An Aromatic Effector Specificity Mutant of the Transcriptional Regulator DmpR Overcomes the Growth Constraints of *Pseudomonas* sp. Strain CF600 on para-Substituted Methylphenols", Journal of Bacteriology, 1994, pp. 7550-7557, vol. 176, No. 24.
Juan L. Ramos et al., "Transcriptional Control of the *Pseudomonas* Tol Plasmid Catabolic Operons is Achieved through an Interplay of Host Factors and Plasmid-Encoded Regulators", Annu. Rev. Microbiol, 1997, pp. 341-372, vol. 51.
Victoria Shingler et al., "Cloning and Nucleotide Sequence of the Gene Encoding the Positive Regulator (DmpR) of the Phenol Catabolic Pathway Encoded by pVI150 and Identification of DmpR as a Member of the NtrC Family of Transcriptional Activators", Journal of Bacteriology, 1993, pp. 1596-1604, vol. 175, No. 6.
Annemarie Simons et al., "Possible ideal lac operator: *Escherichia coli* lac operator-like sequences from eukaryotic genomes lack the central G.C pair", Proc. Natl. Acad. Sci., 1984, pp. 1624-1628, vol. 81.
Lubert Stryer et al., "Biochemistry", 1995.
Chun Chau Sze et al., "Growth Phase-Dependent Transcription of the $\sigma^{54}$-Dependent Po Promoter Controlling the *Pseudomonas*-Derived (Methyl)phenol dmp Operon of pVI150", Journal of Bacteriology, 1996, pp. 3727-3735, vol. 178, No. 13.
Taku Uchiyama et al., "Substrate-induced gene-expression screening of environmental metagenome libraries for isolation of catabolic genes", Nature Biotechnology, 2005, pp. 88-93, vol. 23, No. 1.
J. Craig Venter et al., "Environmental Genome Shotgun Sequencing of the Sargasso Sea", Science, 2004, pp. 66-74, vol. 304.
Youming Zhang et al., "A new logic for DNA engineering using recombination in *Escherichia coli*", Nature Genetics, 1998, pp. 123-128, vol. 20.
Youming Zhang et al., "DNA cloning by homologous recombination in *Escherichia coli*", 2000, Nature Biotechnology, pp. 1314-1317, vol. 18.
English Language Abstract of KR 10-2003-0089115 A which is an application publication of KR 10-0464068 B1.
English Language Abstract of KR 10-2003-0044520 A which is an application publication of KR 10-0865216 B1.
English Language Abstract of KR 10-2004-0061588 A.
English Language Abstract of KR 10-2006-0015359 A which is an application publication of KR 10-0724004 B1.
English Language Abstract of KR 10-0681815 B1 which is a published application of KR 10-2005-0116672 A.
International Search Report of PCT/KR2010/003674 dated Feb. 23, 2011.

* cited by examiner

FIG. 11A

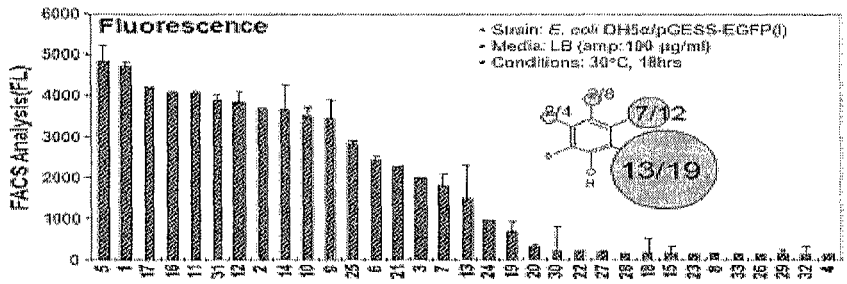

FIG. 11B

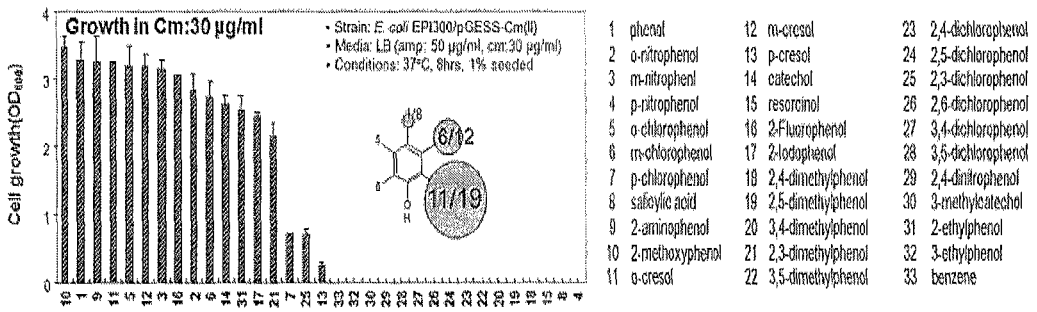

| | | | |
|---|---|---|---|
| 1 phenol | 12 m-cresol | 23 2,4-dichlorophenol |
| 2 o-nitrophenol | 13 p-cresol | 24 2,5-dichlorophenol |
| 3 m-nitrophenol | 14 catechol | 25 2,3-dichlorophenol |
| 4 p-nitrophenol | 15 resorcinol | 26 2,6-dichlorophenol |
| 5 o-chlorophenol | 16 2-Fluorophenol | 27 3,4-dichlorophenol |
| 6 m-chlorophenol | 17 2-Iodophenol | 28 3,5-dichlorophenol |
| 7 p-chlorophenol | 18 2,4-dimethylphenol | 29 2,4-dinitrophenol |
| 8 salicylic acid | 19 2,5-dimethylphenol | 30 3-methylcatechol |
| 9 2-aminophenol | 20 3,4-dimethylphenol | 31 2-ethylphenol |
| 10 2-methoxyphenol | 21 2,3-dimethylphenol | 32 3-ethylphenol |
| 11 o-cresol | 22 3,5-dimethylphenol | 33 benzene |

FIG. 11C

| No | | Aromatic side chains | | | | | |
|---|---|---|---|---|---|---|---|
| | | 1 | 2 | 3 | 4 | 5 | 6 |
| 1 | phenol | OH | | | | | |
| 2 | o-nitrophenol | OH | NO$_2$ | | | | |
| 3 | m-nitrophenol | OH | | NO$_2$ | | | |
| 4 | p-nitrophenol | OH | | | NO$_2$ | | |
| 5 | o-chlorophenol | OH | Cl | | | | |
| 6 | m-chlorophenol | OH | | Cl | | | |
| 7 | p-chlorophenol | OH | | | Cl | | |
| 8 | salicylic acid | OH | COOH | | | | |
| 9 | 2-aminophenol | OH | NH$_2$ | | | | |
| 10 | 2-methoxyphenol | OH | OCH$_3$ | | | | |
| 11 | o-cresol | OH | CH$_3$ | | | | |
| 12 | m-cresol | OH | | CH$_3$ | | | |
| 13 | p-cresol | OH | | | CH$_3$ | | |
| 14 | catechol | OH | OH | | | | |
| 15 | resorcinol | OH | | OH | | | |
| 16 | 2-Fluorophenol | OH | F | | | | |
| 17 | 2-Iodophenol | OH | I | | | | |
| 18 | 2,4-dimethylphenol | OH | CH$_3$ | | CH$_3$ | | |
| 19 | 2,5-dimethylphenol | OH | CH$_3$ | | | CH$_3$ | |
| 20 | 3,4-dimethylphenol | OH | | CH$_3$ | CH$_3$ | | |
| 21 | 2,3-dimethylphenol | OH | CH$_3$ | CH$_3$ | | | |
| 22 | 3,5-dimethylphenol | OH | | CH$_3$ | | CH3 | |
| 23 | 2,4-dichlorophenol | OH | Cl | | Cl | | |
| 24 | 2,5-dichlorophenol | OH | Cl | | | Cl | |
| 25 | 2,3-dichlorophenol | OH | Cl | Cl | | | |
| 26 | 2,6-dichlorophenol | OH | Cl | | | | Cl |
| 27 | 3,4-dichlorophenol | OH | | Cl | Cl | | |
| 28 | 3,5-dichlorophenol | OH | | Cl | | Cl | |
| 29 | 2,4-dinitrophenol | OH | NO$_2$ | | NO$_2$ | | |
| 30 | 3-methylcatechol | OH | OH | CH$_3$ | | | |
| 31 | 2-ethylphenol | OH | CH$_2$CH$_3$ | | | | |
| 32 | 3-ethylphenol | OH | | CH$_2$CH$_3$ | | | |
| 33 | benzene | | | | | | |

FIG. 14A
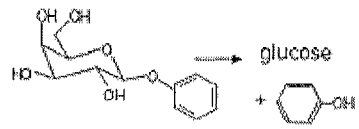 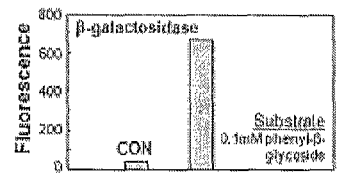
FIG. 14B
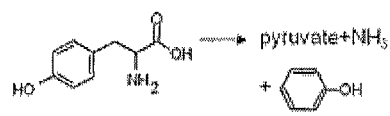 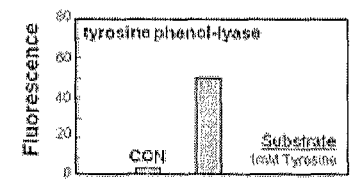
FIG. 14C
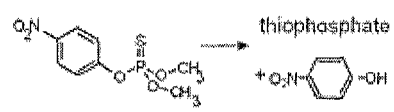 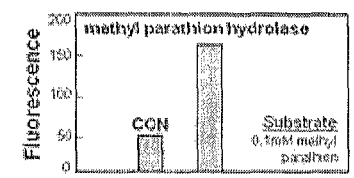

A: Tyrosine phenol-lyase from *Citrobacter freundii*
B: Tyrosine phenol-lyase from *Symbiobacterium toebii*
C: vector(psHCE)

Electrophoresis photograph of fosmid digested with
restriction enzymes
(B; *BamH*I, E; *EcoR*I)

METHOD OF SCREENING AND QUANTIFYING VARIOUS ENZYMATIC ACTIVITIES USING ARTIFICIAL GENETIC CIRCUITS

TECHNICAL FIELD

The present invention relates to a method of screening and quantifying various enzymatic activity and to a method of screening enzymatic activity derived from a metagenomic library based thereon in a high-throughput manner. More specifically, the invention relates to a method of screening and quantifying various enzymatic activity using an artificial genetic circuit for sensing phenolic compounds and to a method of screening target enzymatic activity derived from a metagenome in a high-throughput manner, thereby securing target enzyme genes.

BACKGROUND ART

Biocatalysts are recognized as key materials for "sustainable economic development", including clean technology for the production of energy, industrial materials, etc, and various efforts have been made to screen enzymes having new chemical reactivity, specificity, and stability. Methods for high-throughput screening of antibiotic resistance genes, enzymes essential for growth, several industrial enzymes (e.g., amylase, lipase, protease, etc.), and the like on solid media have been known, but most enzymatic functions depend on the technology for analysis of individual activity that requires much time and cost.

In recent years, studies on the application of directed evolution technology to secure new genetic resources from microbial genomes or metagenomes or improve the activity of existing genes to develop highly useful biocatalysts have emerged as important strategies in bioengineering technology. Thus, there is a need to develop novel high-sensitivity screening technology for high-throughput detection of the activities of very small amounts of enzymes.

Methods of obtaining new enzyme genes from various genetic resources, such as microbial genomes and environmental DNA (metagenome), include a sequence-based screening method that comprises sequencing DNA, performing a PCR reaction, and obtaining the amplified gene. Utilizability of this method is increasing day by day as genome information increases rapidly, and it has an advantage in that only desired genes can be specifically selected. However, this method has a shortcoming in that, because it can be applied only when accurate information about the nucleotide sequences of target genes is known, the application thereof is limited to a portion of genetic resources.

In addition, a function-based screening method that selects genes based on gene function, that is, enzyme activity, is also widely used. To screen enzyme activity by this method, methods of isolating microorganisms directly from environmental samples, including samples from soil, rivers, industrial wastewater, seawater, and forests, have been mainly used. However, the amount of microbial species that can actually be cultured in laboratories is as small as less than 1% of microorganisms present in nature. In recent years, a strategy of constructing genetic resources as metagenomic libraries by isolating DNA directly from environmental samples without culturing microorganisms has been actively attempted. Thus, there is a rising interest on developing a screening technology for detecting industrially useful enzymatic activities directly from metagenomic libraries.

Meanwhile, main technologies for high-throughput analysis of enzymatic activities include: 1) automated multiplex assay technology utilizing well plates; 2) a method of observing color development or a clear zone (halo) on solid medium; and 3) a selective isolation method utilizing nutritionally deficient microorganisms. These methods are based on the actual activity of an enzyme, and thus have an advantage in that they can precisely select a gene of desired function. However, because each detection technology is required for each enzymatic activity, the general use of these methods is limited. Additionally, the effects of these methods are further reduced when the transcription, translation, or expression of a foreign gene in host cells is low or problems such as protein folding or secretion arise. Indeed, in the case of new enzymes derived from genetic resources, such as new microbial genomes and metagenomes, which have high genetic diversity and the genetic characteristics of which is unknown, their expression levels in recombinant microorganisms is very low, and thus it is very difficult to apply the above high-throughput assay method to these enzymes. Thus, there has been a continual need to develop a new high-throughput screening principle according to which even the activity of an enzyme that is expressed at a very low level can be detected with high sensitivity.

In this context, a study on artificial genetic circuitry of detecting the activity of enzymes such as intracellular protease by genetic engineering technology based on the principle of transcriptional activation in a yeast 3-hybrid system was reported and received attention. In addition, technology of detecting enzymatic activities using products resulting from the action of foreign enzymes as nutrients for cells or detecting the enzymatic activities of foreign genes in recombinant E. coli by introducing the recombinant E. coli with transcription regulatory proteins from other microorganisms, by redesigning microbial metabolic pathways, is being actively studied. In addition, efforts to develop protein engineering technology for modifying the substrate specificity of regulatory proteins are being actively made. For example, modifying the substrate specificity of the regulatory protein HbpR, which binds to 2-hydroxybiphenyl (2-HBP), so as to specifically recognize 2-chlorobiphenyl (2-CBP) having chloro- in place of hydroxy-, was also studied (Beggah et al., (2008) Microb. Biotechnol. 1(1): 68-78).

Thus, detecting the products of enzymatic reactions using regulatory proteins can be used as innovative technologies for screening new enzymes. However, such technologies are merely technologies for screening a small number of specific enzymatic activities for which substrate products and regulatory proteins are elucidated, and these technologies cannot be universal systems that can be applied to various enzymatic activities.

Other technologies for screening new enzymes include SIGEX (substrate-induced gene expression screening) reported by the Watanabe research group in 2005. This technology is based on screening promoters whose transcriptional activity is induced by added substrates. Thus, it is not a technology for directly screening enzymatic activity, but is a technology for indirectly detecting genes. Namely, enzymatic functions which are not associated with transcriptional activation are not detected by this technology. In this technology, there is an advantage in that, because FACS analysis can be used, large amounts of samples can be treated within a short time. However, this technology is difficult to apply to a metagenomic library containing large genes having a size of 20-30 kb, and GFP activation in the direction of genes in a library cannot appear (Uchiyama et al., (2005) *Nat. Biotech.* 23: 88-93).

Meanwhile, studies on a technology for detecting phenolic compounds have been Known (Korean Patent Registration No. 10-0464068), but a study on the use of this technology to detect enzymatic activities has not yet been reported before.

The present inventors have conducted studies on a method capable of detecting various enzymatic activities. As a result, based on the fact that various phenol-release compounds capable of liberating phenol can be used as substrates in many enzymatic reactions, the present inventors have constructed artificial genetic circuits detecting phenols and found that the use of the artificial genetic circuits allows the measurement of quantitative activities of reporter genes, such as fluorescent reporter genes and antibiotic resistance genes, the expression of which was induced. Thus, the present inventors have confirmed the effectiveness and general utility of this technology by collecting and isolating genes having tyrosine phenol-lyase and alkaline phosphatase enzyme activities from a metagenomic library by high-throughput screening (million/day) using such genetic circuits, thereby completing the present invention.

DISCLOSURE OF INVENTION

It is an object of the present invention to provide a method of screening target enzyme activity using an artificial genetic circuit, the method comprising the steps of: (a) either providing an artificial genetic circuit for detecting a phenolic compound, the artificial genetic circuit comprising (i) a gene encoding a phenolic compound-degrading enzyme regulatory protein which recognizes a phenolic compound, (ii) at least one reporter gene selected from the group consisting of fluorescence protein-encoding genes and antibiotic resistance genes, and (iii) a gene expression regulatory region consisting of a promoter regulating the expression of the phenolic compound-degrading enzyme regulatory protein, a region to which the phenolic compound-degrading enzyme regulatory protein binds to induce the expression of a downstream reporter gene, and a promoter regulating the expression of the reporter gene, or providing microorganisms containing the genetic circuit in their chromosomal DNA or cytoplasm; (b) providing a clone or gene library containing a gene encoding an enzyme to be screened; (c) introducing the clone or gene library and the artificial gene circuit for detecting the phenolic compound into host microorganisms to prepare recombinant microorganisms; (d) treating the recombinant microorganisms with a phenol-release compound capable of liberating a phenolic compound by an enzymatic reaction; and (e) detecting the activity of the reporter protein whose expression was induced by sensing the phenolic compound liberated by the enzymatic reaction.

Another object of the present invention is to provide a method of quantifying target enzyme activity using an artificial genetic circuit, the method comprising the steps of: (a) either providing an artificial genetic circuit for detecting a phenolic compound, the artificial genetic circuit comprising (i) a gene encoding a phenolic compound-degrading enzyme regulatory protein which recognizes a phenolic compound, (ii) at least one reporter gene selected from the group consisting of fluorescence protein-encoding genes and antibiotic resistance genes, and (iii) a gene expression regulatory region consisting of a promoter regulating the expression of the phenolic compound-degrading enzyme regulatory protein, a region to which the phenolic compound-degrading enzyme regulatory protein binds to induce the expression of a downstream reporter gene, and a promoter regulating the expression of the reporter gene, or providing microorganisms containing the genetic circuit in their chromosomal DNA or cytoplasm; (b) providing a clone or gene library containing a gene encoding an enzyme to be screened; (c) introducing the clone or gene library and the artificial gene circuit for detecting the phenolic compound into host microorganisms to prepare recombinant microorganisms; (d) treating the recombinant microorganisms with a phenol-release compound capable of liberating a phenolic compound by an enzymatic reaction; and (e) quantifying the activity of the reporter protein whose expression was induced by sensing the phenolic compound liberated by the enzymatic reaction.

Still another object of the present invention is to provide a method of screening a target enzyme capable of liberating a phenolic compound by the reaction of an enzyme from a metagenomic library, the method comprising the steps of: (a) providing a metagenomic library from a natural environment; (b) either providing an artificial genetic circuit for detecting a phenolic compound, the artificial genetic circuit comprising (i) a gene encoding a phenolic compound-degrading enzyme regulatory protein which recognizes a phenolic compound, (ii) at least one reporter gene selected from the group consisting of fluorescence protein-encoding genes and antibiotic resistance genes, and (iii) a gene expression regulatory region consisting of a promoter regulating the expression of the phenolic compound-degrading enzyme regulatory protein, a region to which the phenolic compound-degrading enzyme regulatory protein binds to induce the expression of a downstream reporter gene, and a promoter regulating the expression of the reporter gene, or providing microorganisms containing the genetic circuit in their chromosomal DNA or cytoplasm; (c) introducing the metagenomic library and the artificial genetic circuit into host microorganisms to construct a library of transformed microorganisms; (d) treating the library of transformed microorganisms with a phenol-release compound capable of liberating a phenolic compound by an enzymatic reaction; (e) measuring the activity of the reporter protein whose expression was induced by sensing the phenolic compound liberated by the enzymatic reaction, thereby performing high-throughput screening of microorganisms having activity of liberating the phenolic compound by the enzymatic reaction; and (f) collecting a gene of the enzyme, which is capable of liberating the phenolic compound by the enzymatic reaction, from the screened microorganisms, and then identifying the gene by sequencing.

To achieve the above objects, the present invention provides a method of screening target enzyme activity using an artificial genetic circuit, the method comprising the steps of: (a) providing an artificial genetic circuit for detecting a phenolic compound, the artificial genetic circuit comprising (i) a gene encoding a phenolic compound-degrading enzyme regulatory protein which recognizes a phenolic compound, (ii) at least one reporter gene selected from the group consisting of fluorescence protein-encoding genes and antibiotic resistance genes, and (iii) a gene expression regulatory region consisting of a promoter regulating the expression of the phenolic compound-degrading enzyme regulatory protein, a region to which the phenolic compound-degrading enzyme regulatory protein binds to induce the expression of a downstream reporter gene, and a promoter regulating the expression of the reporter gene; (b) providing a clone or gene library containing a gene encoding an enzyme to be screened; (c) introducing the clone or gene library and the artificial gene circuit for detecting the phenolic compound into host microorganisms to prepare recombinant microorganisms; (d) treating the recombinant microorganisms with a phenol-release compound capable of liberating a phenolic compound by an enzymatic reaction; and (e) detecting the activity of the reporter protein whose expression was induced by sensing the phenolic compound liberated by the enzymatic reaction.

The present invention also provides a method of screening target enzyme activity using an artificial genetic circuit, the method comprising the steps of: (a) providing microorganisms containing in their chromosomal DNA or cytoplasm an artificial genetic circuit for detecting a phenolic compound, the artificial genetic circuit comprising (i) a gene encoding a phenolic compound-degrading enzyme regulatory protein which recognizes a phenolic compound, (ii) at least one reporter gene selected from the group consisting of fluorescence protein-encoding genes and antibiotic resistance genes, and (iii) a gene expression regulatory region consisting of a promoter regulating the expression of the phenolic compound-degrading enzyme regulatory protein, a region to which the phenolic compound-degrading enzyme regulatory protein binds to induce the expression of a downstream reporter gene, and a promoter regulating the expression of the reporter gene; (b) providing a clone or gene library containing a gene encoding an enzyme to be screened; (c) introducing the clone or gene library into microorganisms containing the artificial gene circuit for detecting the phenolic compound to prepare recombinant microorganisms; (d) treating the recombinant microorganisms with a phenol-release compound capable of liberating a phenolic compound by an enzymatic reaction; and (e) detecting the activity of the reporter protein whose expression was induced by sensing the phenolic compound liberated by the enzymatic reaction.

The present invention also provides a method of quantifying target enzyme activity using an artificial genetic circuit, the method comprising the steps of: (a) providing an artificial genetic circuit for detecting a phenolic compound, the artificial genetic circuit comprising (i) a gene encoding a phenolic compound-degrading enzyme regulatory protein which recognizes a phenolic compound, (ii) at least one reporter gene selected from the group consisting of fluorescence protein-encoding genes and antibiotic resistance genes, and (iii) a gene expression regulatory region consisting of a promoter regulating the expression of the phenolic compound-degrading enzyme regulatory protein, a region to which the phenolic compound-degrading enzyme regulatory protein binds to induce the expression of a downstream reporter gene, and a promoter regulating the expression of the reporter gene; (b) providing a clone or gene library containing a gene encoding an enzyme to be screened; (c) introducing the clone or gene library and the artificial gene circuit for detecting the phenolic compound into host microorganisms to prepare recombinant microorganisms; (d) treating the recombinant microorganisms with a phenol-release compound capable of liberating a phenolic compound by an enzymatic reaction; and (e) quantifying the activity of the reporter protein whose expression was induced by sensing the phenolic compound liberated by the enzymatic reaction.

The present invention also provides a method of quantifying target enzyme activity using an artificial genetic circuit, the method comprising the steps of: (a) providing microorganisms containing in their chromosomal DNA or cytoplasm an artificial genetic circuit for detecting a phenolic compound, the artificial genetic circuit comprising (i) a gene encoding a phenolic compound-degrading enzyme regulatory protein which recognizes a phenolic compound, (ii) at least one reporter gene selected from the group consisting of fluorescence protein-encoding genes and antibiotic resistance genes, and (iii) a gene expression regulatory region consisting of a promoter regulating the expression of the phenolic compound-degrading enzyme regulatory protein, a region to which the phenolic compound-degrading enzyme regulatory protein binds to induce the expression of a downstream reporter gene, and a promoter regulating the expression of the reporter gene; (b) providing a clone or gene library containing a gene encoding an enzyme to be screened; (c) introducing the clone or gene library into microorganisms containing the artificial gene circuit for detecting the phenolic compound to prepare recombinant microorganisms; (d) treating the recombinant microorganisms with a phenol-release compound capable of liberating a phenolic compound by an enzymatic reaction; and (e) quantifying the activity of the reporter protein whose expression was induced by sensing the phenolic compound liberated by the enzymatic reaction.

The present invention also provides a method of screening a target enzyme capable of liberating a phenolic compound by the reaction of an enzyme from a metagenomic library, the method comprising the steps of: (a) providing a metagenomic library from a natural environment; (b) providing an artificial genetic circuit for detecting a phenolic compound, the artificial genetic circuit comprising (i) a gene encoding a phenolic compound-degrading enzyme regulatory protein which recognizes a phenolic compound, (ii) at least one reporter gene selected from the group consisting of fluorescence protein-encoding genes and antibiotic resistance genes, and (iii) a gene expression regulatory region consisting of a promoter regulating the expression of the phenolic compound-degrading enzyme regulatory protein, a region to which the phenolic compound-degrading enzyme regulatory protein binds to induce the expression of a downstream reporter gene, and a promoter regulating the expression of the reporter gene; (c) introducing the metagenomic library and the artificial genetic circuit into host microorganisms to construct a library of transformed microorganisms; (d) treating the library of transformed microorganisms with a phenol-release compound capable of liberating a phenolic compound by an enzymatic reaction; (e) measuring the activity of the reporter protein whose expression was induced by sensing the phenolic compound liberated by the enzymatic reaction, thereby performing high-throughput screening of microorganisms having activity of liberating the phenolic compound by the enzymatic reaction; and (f) collecting a gene of the enzyme, which is capable of liberating the phenolic compound by an enzymatic reaction, from the screened microorganisms, and then identifying the gene by sequencing.

The present invention also provides a method of screening a target enzyme capable of liberating a phenolic compound by the reaction of an enzyme from a metagenomic library, the method comprising the steps of: (a) providing a metagenomic library from a natural environment; (b) providing microorganisms containing in their chromosomal DNA or cytoplasm an artificial genetic circuit for detecting a phenolic compound, the artificial genetic circuit comprising (i) a gene encoding a phenolic compound-degrading enzyme regulatory protein recognizing a phenolic compound, (ii) at least one reporter gene selected from the group consisting of fluorescence protein-encoding genes and antibiotic resistance genes, and (iii) a gene expression regulatory region consisting of a promoter regulating the expression of the phenolic compound-degrading enzyme regulatory protein, a region to which the phenolic compound-degrading enzyme regulatory protein binds to induce the expression of a downstream reporter gene, and a promoter regulating the expression of the reporter gene; (c) introducing the metagenomic library into the microorganisms containing in their chromosomal DNA or cytoplasm the artificial genetic circuit to construct a library of transformed microorganisms; (d) treating the library of transformed microorganisms with a phenol-release compound capable of liberating a phenolic compound by an enzymatic reaction; (e) measuring the activity of the reporter protein whose expression was induced by sensing the phenolic compound liberated by the enzymatic reaction, thereby performing high-throughput screening of microorganisms having activity of liberating the phenolic compound by the enzymatic reaction; and (f) collecting a gene of the enzyme, which is capable of liberating the phenolic compound by the enzymatic reaction, from the screened microorganisms, and then identifying the gene by sequencing.

BRIEF DESCRIPTION OF THE DRAWINGS

FIG. 2 is a schematic view showing high-throughput screening of a metagenomic library using a genetic circuit including a fluorescence protein or antibiotic resistance protein reporter, wherein

FIG. 3 shows a method comprising removing an artificial genetic circuit from a selected microbial strain and collecting a pure fosmid vector containing a useful gene, wherein

FIG. 9 shows the results of examining the reaction of pGESS in various E. coli strains (DH5a, EPI300, JM109 (DE3), BL21, BL21(DE3)) in order to construct an optimum E. coli host for the GESS system, in which

FIG. 10 shows the ability of pGESS-EGFP to quantify phenol, in which

FIG. 11 shows the results of measuring the sensing ability of pGESS to detect various phenolic compounds, in which FIG. 11A shows responses obtained when using a fluorescence protein as a reporter, FIG. 11B shows responses obtained when using a chloramphenicol resistance protein as a reporter, and FIG. 11C shows information about phenolic compounds used in the experiments.

FIG. 12 shows the results of examining quantitative responses according to concentrations of various phenolic compounds, in which

FIG. 13 shows the results of examining the phenol content of wastewater using pGESS.

FIG. 14 shows the results of detecting the activities of various enzymes using pGESS, in which FIG. 14A shows the results of detecting the enzymatic activity of E. coli-derived β-galactosidase, FIG. 14B shows the results of detecting the enzymatic activity of Citrobacter freundii-derived tyrosine-phenol-lyase, and FIG. 14C shows the results of detecting the enzymatic activity of Pseudomonas sp.-derived methyl parathion hydrolase.

FIG. 15 shows the results of detecting the activity of tyrosine phenol-lyase (TPL) using various reporters, in which

FIG. 16 shows the results of quantitatively measuring the difference in activity between enzymes using pGESS.

FIG. 17 shows the results of examining the effect of medium components on the ability of pGESS to detect phenol, in which

FIG. 19 shows the results of attempting separation between a cell growth step and a genetic circuit activating step during measurement of enzymatic activity in order to optimize a reaction for sensing enzymatic activity, in which

FIG. 20 shows the results of improving phenol sensitivity and recognition specificity by modifying genetic circuits, in which

FIG. 21 shows the results of performing high-throughput screening of tyrosine phenol-lyase from a genomic library from *Citrobactor freundii* using the GESS system, in which

FIG. 22 shows the results of constructing a metagenomic fosmid library, in which

FIG. 25 shows the results of examining the properties of novel alkaline phosphatase at various pHs and temperatures, in which

BEST MODE FOR CARRYING OUT THE INVENTION

Figure 1A:
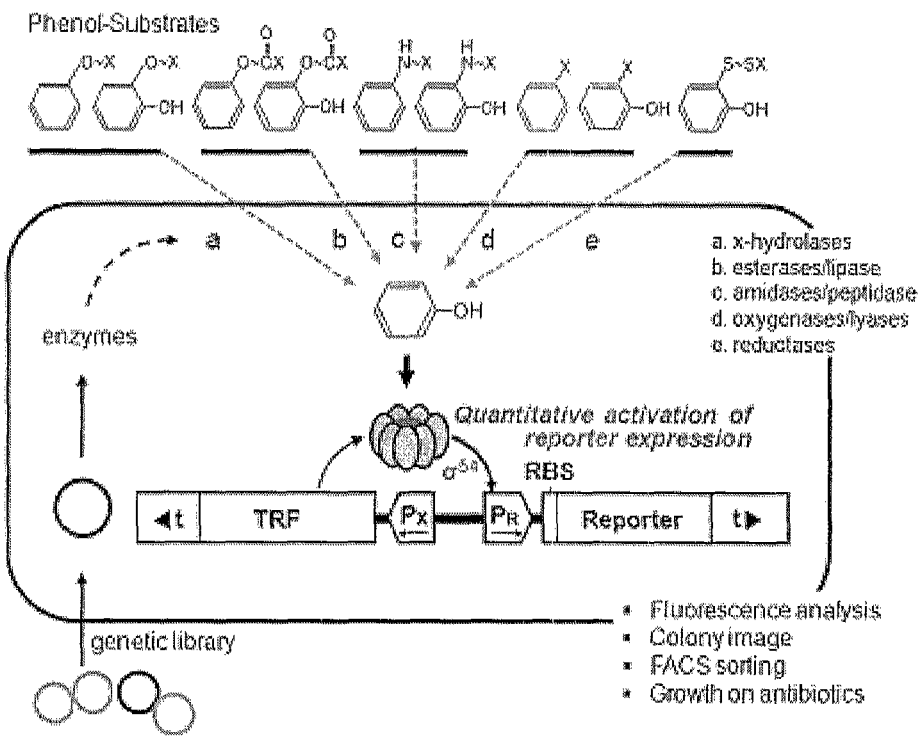
FIG. 1(A) shows a principle (genetic enzyme screening system (GESS)) of detecting various types of enzymatic activities using an artificial genetic circuit according to the present invention, and FIG. 1B schematically shows a GESS vector (pGESS) employing the artificial genetic circuit according to the present invention and is an enlarged view of the gene expression regulatory region of the vector.

Unless defined otherwise, all technical and scientific terms used herein have the same meaning as commonly understood by one of ordinary skill in the art to which the invention pertains. Generally, the nomenclature used herein is well known and commonly employed in the art.

The present invention is directed to a technology (genetic enzyme screening system; GESS) of performing high-throughput screening of various enzymatic activities with high sensitivity using artificial genetic circuits.

Phenol is contained in various hydrocarbon resources, including petroleum, coal, lignin and the like, and is also contained in artificially synthesized compounds. Thus, enzymatic reactions involving phenolic residues as reaction substrates or products are very various, and for example, enzymatic species that liberate phenolic compounds in the reactions of 40,000 enzymes listed in the Brenda database (www.brenda-enzymes.info) providing information associated with a wide kind of enzymes reached about 2,000 species (about 5% of the total list) as a result of search. The present invention relates to the technology comprising performing enzymatic reactions using various compounds having a phenol group bound thereto as synthetic substrates and detecting the liberated phenol by a genetic engineering method. Thus, the technology of the present invention is a general-purpose enzyme screening technology that can be generally applied to a very wide range of enzymes. O/p-nitrophenol compounds are colorless when coupled with other organic compounds, but nitrophenol liberated from substrates develops a yellow color. Thus, synthetic substrates for rapidly measuring the activity of various hydrolytic enzymes have been developed. For example, Sigma-Aldrich sells about 500 nitrophenol compounds. However, these compounds show low absorbance and easily diffuse through the cell wall, so that various cellular reaction products are mixed with each other. Thus, these nitrophenol compounds are not suitable to detect the activity of each type of cell or colony.

In addition, phenolic compounds are not easily degraded in *E. coli* cells, and thus even very small amounts of reaction products produced by enzymatic reactions can be detected with high sensitivity. This property is consistent with the fact that, when IPTG (isopropylthiogalactoside) which is non-degradable is used to induce the expression of a lactose promoter, even a small amount of IPTG shows a strong effect of inducing the expression. Recently, a study on regulating the intracellular stability of a reporter protein to regulate the sensitivity and quantification of a promoter was reported (Neuenschwander et al., (2007) *Nat. Biotech.* 25(10): 1145-1147). Although some phenol derivatives show cytotoxicity, about 100 ppm or less of phenolic compounds did not have a significant influence on the growth of *E. coli*.

As such, because phenolic compounds are not easily degraded in cells, they can highly sensitively detect even trace amounts of reaction products produced by enzymatic reactions, and various phenol-release compounds capable of liberating phenol in enzymatic reactions can be used as substrates. Based on this fact, the present inventors have developed methods for screening and quantifying enzymatic activity, the method comprising designing an artificial genetic circuit sensing phenolic compounds, introducing the genetic circuit into microorganisms to obtain recombinant microorganisms, adding a phenol group-containing substrate fit for the purpose to the recombinant microorganisms, and measuring the quantitative activity of reporters, such as fluorescence or antibiotic resistance reporters, the expression of which was induced by sensing phenols produced according to the function of enzymatic genes.

In one aspect, the present invention is directed to a method of screening target enzyme activity using an artificial genetic circuit, the method comprising the steps of: (a) providing an artificial genetic circuit for detecting a phenolic compound, the artificial genetic circuit comprising (i) a gene encoding a phenolic compound-degrading enzyme regulatory protein which recognizes a phenolic compound, (ii) at least one reporter gene selected from the group consisting of fluorescence protein-encoding genes and antibiotic resistance genes, and (iii) a gene expression regulatory region consisting of a promoter regulating the expression of the phenolic compound-degrading enzyme regulatory protein, a region to which the phenolic compound-degrading enzyme regulatory protein binds to induce the expression of a downstream reporter gene, and a promoter regulating the expression of the reporter gene; (b) providing a clone or gene library containing a gene encoding an enzyme to be screened; (c) introducing the clone or gene library and the artificial gene circuit for detecting the phenolic compound into host microorganisms to prepare recombinant microorganisms; (d) treating the recombinant microorganisms with a phenol-release compound capable of liberating a phenolic compound by an enzymatic reaction; and (e) measuring the activity of the reporter protein whose expression was induced by sensing the phenolic compound liberated by the enzymatic reaction.

In the method of the present invention, the step of preparing the recombinant microorganisms, which have introduced therein the clone or gene library and the artificial genetic circuit for detecting the phenolic compound, may be carried out by providing microorganisms containing the artificial genetic circuit for detecting the phenolic compound and introducing the clone or gene library into the microorganisms.

In another aspect, the present invention is directed to a method of screening target enzyme activity using an artificial genetic circuit, the method comprising the steps of: (a) providing microorganisms containing in their chromosomal DNA or cytoplasm an artificial genetic circuit for detecting a phenolic compound, the artificial genetic circuit comprising (i) a gene encoding a phenolic compound-degrading enzyme regulatory protein which recognizes a phenolic compound, (ii) at least one reporter gene selected from the group consisting of fluorescence protein-encoding genes and antibiotic resistance genes, and (iii) a gene expression regulatory region consisting of a promoter regulating the expression of the phenolic compound-degrading enzyme regulatory protein, a region to which the phenolic compound-degrading enzyme regulatory protein binds to induce the expression of a downstream reporter gene, and a promoter regulating the expression of the reporter gene; (b) providing a clone or gene library containing a gene encoding an enzyme to be screened; (c) introducing the clone or gene library into microorganisms containing the artificial gene circuit for detecting the phenolic compound to prepare recombinant microorganisms; (d) treating the recombinant microorganisms with a phenol-release compound capable of liberating a phenolic compound by an enzymatic reaction; and (e) measuring the activity of the reporter protein whose expression was induced by sensing the phenolic compound liberated by the enzymatic reaction.

In step (a) of the method of the present invention, the artificial genetic circuit for detecting the phenolic compound may be contained in the cytoplasm of the microorganisms using a plasmid or inserted into the chromosomal DNA.

In still another aspect, the present invention is directed to a method of quantifying target enzyme activity using an artificial genetic circuit, the method comprising the steps of: (a) providing an artificial genetic circuit for detecting a phenolic compound, the artificial genetic circuit comprising (i) a gene encoding a phenolic compound-degrading enzyme regulatory protein which recognizes a phenolic compound, (ii) at least one reporter gene selected from the group consisting of fluorescence protein-encoding genes and antibiotic resistance genes, and (iii) a gene expression regulatory region consisting of a promoter regulating the expression of the phenolic compound-degrading enzyme regulatory protein, a region to which the phenolic compound-degrading enzyme regulatory protein binds to induce the expression of a downstream reporter gene, and a promoter regulating the expression of the reporter gene; (b) providing a clone or gene library containing a gene encoding an enzyme to be screened; (c) introducing the clone or gene library and the artificial gene circuit for detecting the phenolic compound into host microorganisms to prepare recombinant microorganisms; (d) treating the recombinant microorganisms with a phenol-release compound capable of liberating a phenolic compound by an enzymatic reaction; and (e) quantifying the activity of the reporter protein whose expression was induced by sensing the phenolic compound liberated by the enzymatic reaction.

In yet another aspect, the present invention is directed to a method of quantifying target enzyme activity using an artificial genetic circuit, the method comprising the steps of: (a) providing microorganisms containing in their chromosomal DNA or cytoplasm an artificial genetic circuit for detecting a phenolic compound, the artificial genetic circuit comprising (i) a gene encoding a phenolic compound-degrading enzyme regulatory protein which recognizes a phenolic compound, (ii) at least one reporter gene selected from the group consisting of fluorescence protein-encoding genes and antibiotic resistance genes, and (iii) a gene expression regulatory region consisting of a promoter regulating the expression of the phenolic compound-degrading enzyme regulatory protein, a region to which the phenolic compound-degrading enzyme regulatory protein binds to induce the expression of a downstream reporter gene, and a promoter regulating the expression of the reporter gene; (b) providing a clone or gene library containing a gene encoding an enzyme to be screened; (c) introducing the clone or gene library into microorganisms containing the artificial gene circuit for detecting the phenolic compound to prepare recombinant microorganisms; (d) treating the recombinant microorganisms with a phenol-release compound capable of liberating a phenolic compound by an enzymatic reaction; and (e) quantifying the activity of the reporter protein whose expression was induced by sensing the phenolic compound liberated by the enzymatic reaction.

In addition, the present invention is directed to a method for screening enzymatic activity from a metagenomic library. Specifically, the present invention is directed to a method for screening a target enzyme capable of liberating a phenolic compound by an enzymatic reaction.

As used herein, the term "metagenome" is defined as "the collective genomes of all microorganisms present in a given habitat" (Handelsman et al., (1998) *Chem. Biol.* 5: R245-R249). However, this term is also intended to include clones, including the genomes or genes extracted from environmental samples, and a series of studies associated with such metagenome are also called "metagenomics". In related studies, Venter et al. (Venter et al., (2004) *Science* 304: 66-74) performed new conceptual studies on ecosystem sequencing under the support of the US DOE and determined about one billion nucleotide sequences by applying whole-genome shotgun sequencing to a metagenomic library constructed from seawater samples collected from the Bermuda Triangle. The nucleotide sequencing revealed that the collected seawater samples contained at least 1800 microbial genomic species, including 148 unknown bacterial phylotypes and that 1.2 million or more new genes were found. Metagenomic studies are suitable for using microorganisms that are difficult or impossible to culture, and can be considered as molecular biological approaches which are performed using all DNAs extracted from any environment, if DNA isolation by culture is impossible.

Such environmental metagenomic libraries are gene clusters from various environments such as soli or seawater and can be constructed by various known methods.

In the present invention, a metagenomic library is constructed by collecting a microbial community from nature or any area (hot spring, farm, compost, oil-contaminated soil, etc.), extracting a genome directly from the microbial community and introducing the extracted genome into a vector. Examples of a vector that can be used in the present invention include plasmids, fosmids, cosmids, BAC (bacterial artificial chromosome), YAC (yeast artificial chromosome), etc. Plasmids have an advantage in that the degree of expression and the construction of a vector can be achieved according to the user's intension, so that gene expression can be optimized. However, there is a disadvantage in that, because a gene having a small size (~10 kb) is introduced, the recovery of an operon gene is impossible. A gene having a size of 37-52 kb can be introduced into a fosmid, a cosmid, or the like. Particularly, fosmid vectors are frequently used because they have high transformation efficiency. BACs can be introduced with a gene having large size (150-350 kb), and thus are used in the human genome project and the genomic analysis of rats and rice.

In a further aspect, the present invention is directed to a method of screening a target enzyme capable of liberating a phenolic compound by the reaction of an enzyme from a metagenomic library, the method comprising the steps of: (a) providing a metagenomic library from a natural environment; (b) providing an artificial genetic circuit for detecting a phenolic compound, the artificial genetic circuit comprising (i) a gene encoding a phenolic compound-degrading enzyme regulatory protein which recognizes a phenolic compound, (ii) at least one reporter gene selected from the group consisting of fluorescence protein-encoding genes and antibiotic resistance genes, and (iii) a gene expression regulatory region consisting of a promoter regulating the expression of the phenolic compound-degrading enzyme regulatory protein, a region to which the phenolic compound-degrading enzyme regulatory protein binds to induce the expression of a downstream reporter gene, and a promoter regulating the expression of the reporter gene; (c) introducing the metagenomic library and the artificial genetic circuit into host microorganisms to construct a library of transformed microorganisms; (d) treating the library of transformed microorganisms with a phenol-release compound capable of liberating a phenolic compound by an enzymatic reaction; (e) measuring the activity of the reporter protein whose expression was induced by sensing the phenolic compound liberated by the enzymatic reaction, thereby performing high-throughput screening of microorganisms having activity of liberating the phenolic compound by the enzymatic reaction; and (f) collecting a gene of the enzyme, which is capable of liberating the phenolic compound by an enzymatic reaction, from the screened microorganisms, and then identifying the gene by sequencing.

In the method of the present invention, the step of constructing the library of transformed microorganisms having introduced therein the color or gene library and the artificial genetic circuit for detecting the phenolic compound may be carried out by providing microorganisms containing the artificial genetic circuit for detecting the phenolic compound and introducing the metagenomic library into the microorganisms.

In a still further aspect, the present invention is directed to a method of screening a target enzyme capable of liberating a phenolic compound by the reaction of an enzyme from a metagenomic library, the method comprising the steps of: (a) providing a metagenomic library from a natural environment; (b) providing microorganisms containing in their chromosomal DNA or cytoplasm an artificial genetic circuit for detecting a phenolic compound, the artificial genetic circuit comprising (i) a gene encoding a phenolic compound-degrading enzyme regulatory protein which recognizes a phenolic compound, (ii) at least one reporter gene selected from the group consisting of fluorescence protein-encoding genes and antibiotic resistance genes, and (iii) a gene expression regulatory region consisting of a promoter regulating the expression of the phenolic compound-degrading enzyme regulatory protein, a region to which the phenolic compound-degrading enzyme regulatory protein binds to induce the expression of a downstream reporter gene, and a promoter regulating the expression of the reporter gene; (c) introducing the metagenomic library into the microorganisms containing in their chromosomal DNA or cytoplasm the artificial genetic circuit to construct a library of transformed microorganisms; (d) treating the library of transformed microorganisms with a phenol-release compound capable of liberating a phenolic compound by an enzymatic reaction; (e) measuring the activity of the reporter protein whose expression was induced by sensing the phenolic compound liberated by the enzymatic reaction, thereby performing high-throughput screening of microorganisms having activity of liberating the phenolic compound by the enzymatic reaction; and (f) collecting a gene of the enzyme, which is capable of liberating the phenolic compound by the enzymatic reaction, from the screened microorganisms, and then identifying the gene by sequencing.

In step (a) of the method of the present invention, the artificial genetic circuit for detecting the phenolic compound may be contained in the cytoplasm of the microorganisms using a plasmid or inserted into the chromosomal DNA.

According to the method of the present invention, an enzyme having desired activity can be screened and recovered by constructing a genetic circuit sensing phenols, constructing an environmental metagenomic library, stepwise or simultaneously transforming the library into a suitable microorganism, treating the microorganism with a phenol-release compound as a substrate, and measuring the quantitative activity of a reporter such as a fluorescence or antibiotic resistance reporter, the expression of which was induced by sensing a phenol produced according to the function and activity of the enzymatic gene introduced in the cell.

In the present invention, the reporter gene and the promoter regulating the expression of the reporter gene may be operably linked to each other.

In the present invention, the region to which the phenolic compound-degrading enzyme regulatory protein binds to induce the expression of the downstream reporter gene may be a region to which the phenolic compound-degrading enzyme regulatory protein binds to activate the promoter of the reporter gene such that the downstream reporter gene can be expressed.

In the present invention, the gene encoding the phenolic compound-degrading enzyme regulatory protein which recognizes the phenolic compound and the promoter regulating the expression of the regulatory protein may be operably linked to each other.

Figure 1B:
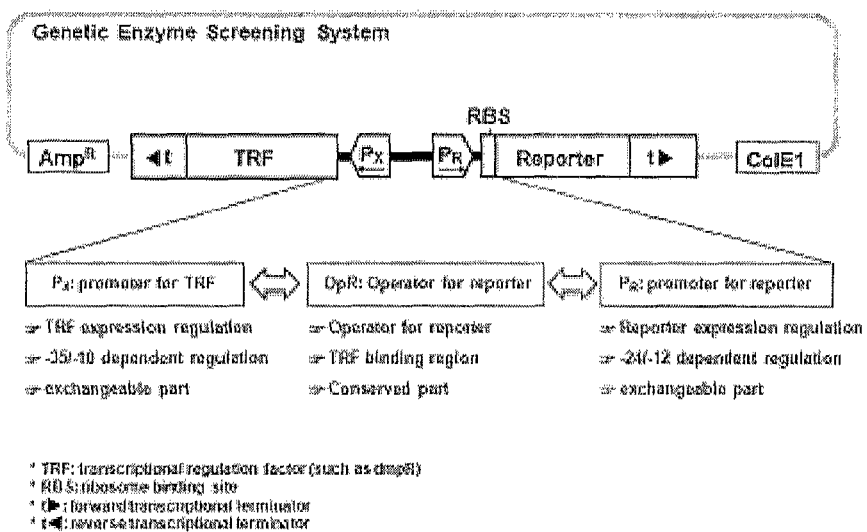
In FIG. 1, TRF: a transcriptional regulation factor that means a phenolic compound-degrading enzyme regulatory protein according to the present invention; OpR: a region to which the phenolic compound-degrading enzyme regulatory protein TRF binds to induce a downstream reporter gene; Px: a promoter regulating the expression of the phenolic compound-degrading enzyme regulatory protein; and $P_R$: a promoter regulating the expression of the reporter gene.

FIG. 1(A) shows a principle of detecting various types of enzymatic activities using an artificial genetic circuit (genetic enzyme screening system (GESS)) according to the present invention, and FIG. 1B schematically shows a GESS vector (pGESS) employing the artificial genetic circuit according to the present invention and is an enlarged view of the gene expression regulatory region of the vector. In FIG. 1, TRF is a transcriptional regulation factor that means a region (e.g., dmpR: gene encoding the positive regulator of the phenol catabolic pathway) encoding a phenolic compound-degrading enzyme regulatory protein in the present invention, and the gene expression regulatory region can be largely divided into three regions: Px: a promoter regulating the expression of the phenolic compound-degrading enzyme regulatory protein; OpR (operator for reporter): a region to which the phenolic compound-degrading enzyme regulatory protein TRF binds to induce a downstream reporter gene; and $P_R$: a promoter regulating the expression of the reporter gene. Additionally, the artificial genetic circuit may comprise RBS (ribosome binding site), a forward transcriptional terminator (t▶), a reverse transcriptional terminator (t◀), etc.

As shown in FIGS. 1A and 1B, the term "artificial genetic circuit (Redesigned genetic circuit)" means a genetic construct comprising (i) a gene encoding a phenolic compound-degrading enzyme regulatory protein which recognizes a phenolic compound, (ii) at least one reporter gene selected from the group consisting of fluorescence protein-encoding genes and antibiotic resistance genes, and (iii) a gene expression regulatory region consisting of a promoter regulating the expression of the phenolic compound-degrading enzyme regulatory protein, a region to which the phenolic compound-degrading enzyme regulatory protein binds to induce the expression of a downstream reporter gene, and a promoter regulating the expression of the reporter gene.

As used herein, the phrase "enzyme to be screened" may be an enzyme that can liberate a phenolic compound by an enzymatic reaction. Examples of the enzymes include alpha-glucosidase, beta-glucosidase, cellulase, glycosylceramidase, phosphatase, phytase, esterase, lipase, urethanase, amidase, peptidase, proteinase, oxydoreductase, phenol-lyase, dihalogenase, isomerase, monooxyenase, and dioxygenase.

As used herein, the "phenolic compound-degrading enzyme regulatory protein" is a protein regulating the expression of a phenolic compound-degrading enzyme and senses phenol to operate the promoter regulating the expression of the phenolic compound-degrading enzyme and to induce the expression of the report linked to the promoter.

With respect to the "phenolic compound-degrading enzyme regulatory protein", genes having the activity of degrading aromatic organic compounds, including phenol, xylene, toluene and benzene, are found mainly in *Pseudomonas* sp. and *Acinetobacter* sp. These genes consist of multifunctional operons and are expressed by $\sigma^{54}$-dependent transcriptional activators. Typical examples of the transcriptional activators include XylR, DmpR, MopR, PhhR, PhlR, TbuT and the like, and among them, XylR involved in toluene and xylene catabolism in *Pseudomonas putida* (Ramos & Marques, (1997) *Annu. Rev. Microbiol.* 51: 341-372) and DmpR involved in phenol catabolism (Shingler et al., (1993) *J. Bacteriol.* 175: 1596-1604) are most well known. Particularly, in order to detect contaminated toluene, xylene or phenol from natural environments, XylR or DmpR has been frequently studied as the concept of microbial biosensors (Ramirez et al., (2004), U.S. Pat. No. 6,803,224 B2; Wise et al., (2004), U.S. Pat. No. 6,773,918 B2). The NtrC family regulator consists of a combination of a domain (domain A) recognizing an activator such as phenol or xylene, a domain (domain C) having ATPase activity, and a domain (domain D) functioning to bind to DNA. Thus, when there is no phenol molecule, domain A inhibits transcription, but when a phenol molecule binds to inhibit domain A, domains C and D show a function of activating transcription. In recent years, a study on the use of domain A to detect new substances and a study on the modification of specificity by domain A were reported (Pavel et al., (1994) *J. Bacteriol.* 176(4): 7550-7557).

Thus, the phenolic compound-degrading enzyme regulatory protein that is preferably used in the present invention may be dmpR that is a phenol-degrading operon regulatory protein from *P. putida*, or a variant thereof. DmpR is the $\sigma^{54}$-dependent transcriptional activity regulatory region of the dmp operon having the activity of degrading aromatic organic compounds, including phenol, xylene, toluene, and benzene. The dmp operon from *P. putida* consists of 15 genes, and among these genes, dmpKLMNOP encodes enzymes necessary for phenol hydroxylation, and dmpQB-CDEFGHI encodes enzymes of the meta catabolic pathway that degrades catechol intermediates. The expression of the dmpKLMNOP operon is activated when the $\sigma^{54}$-dependent transcriptional regulator dmpR binds to the dmp operator upstream of dmpK, and the transcriptional regulator dmpR is known as a $\sigma^{70}$ dependent transcriptional regulator (Lee et al., (1996) *J. Biol. Chem.* 271(29): 17281-17286). In addition, examples of the dmpR variant include E135K (meaning an E-to-K variation at position 135 of the amino acid sequence of dmpR), E172K, D135N, D135N/E172K, F65L, L184I, F42Y, R109C, L113V, D116N, F122L, K6E/F42S, Q10R/K117M, Q10R, D116G/K117R, D116V, etc. Because these variants have high affinity for phenols, various variants containing single or multiple variations at these positions or positions near thereto, as well as various dmpR variants, will fall within the scope of the present invention.

In the present invention, as shown in FIG. 1B, the "gene expression regulatory region" is a portion regulating the artificial genetic circuit consists of (i) a promoter regulating the expression of the phenolic compound-degrading enzyme regulatory protein that is a transcriptional regulator, (ii) a region to which the phenolic compound-degrading enzyme regulatory protein binds to induce the expression of a downstream reporter gene, and (iii) a promoter regulating the expression of the reporter gene. When there is no phenol molecule, domain A of the phenolic compound-degrading enzyme regulatory protein inhibits transcription, but when a phenol molecule binds to inhibit domain A, domains C and D show a function of activating transcription, and thus bind to the OpR (operator for reporter) region as shown in FIG. 1B, and the activity thereof is regulated by depending on $\sigma^{54}$.

As used herein, the term "promoter" means either a promoter regulating the expression of the phenolic compound-degrading enzyme regulatory protein, or a promoter regulating the expression of the reporter protein. For example, the promoter may be a *Pseudomonas* dmpR or dmp operon promoter or a promoter for expression of general protein. For high-level expression of a foreign protein, a high-expression promoter, such as a trc, T7, lac, or ara promoter, may be used, and particularly, the constitutive high-expression vector $P_{hce}$ that does not require an inducer may be used.

In the present invention, the promoter regulating the expression of the reporter protein may be a $\sigma^{54}$-dependent promoter from E. coli. In addition, a person skilled in the art will appreciate that the promoter may be derived from Pseudomonas putida, yeast or the like depending on the host of pGESS.

In the present invention, the artificial genetic circuit preferably may comprise, in addition to the above promoter, a ribosome binding site (RBS) facilitating the expression of the reporter gene and/or a transcriptional terminator. Namely, the artificial genetic circuit may comprise, in addition to the promoter, RBS and/or a transcriptional terminator, which regulates the expression of the regulatory protein.

Generally, the expression of a protein starts with the initiation codon AUG (methionine) or GUG (valine) in mRNA, and the discrimination between the protein initiation codons AUG and GUG and the AUG or GUG residue present in the ribosome protein is determined by RBS (or Shine-Dalgarno (SD) sequence) rich in purine bases of DNA, in which RBS is known to be different between species (Stryer, L., (1995) Biochemistry, (4th ed.) W. H. Freeman, Chapter 34, Protein Synthesis). The artificial genetic circuit constructed in the present invention comprises a transcriptional regulator from Pseudomonas, which is significantly different from E. coli, the host of the genetic circuit. Further, for $\sigma^{54}$-dependent gene expression, a $\sigma^{54}$-binding site or a $\sigma^{54}$-dependent regulator is significantly different from that derived from E. coli. Thus, in order to facilitate the expression of the reporter gene in the Pseudomonas RBS or the host E. coli, E. coli RBS or RBS that can be derived from all microbial strains may be used in the present invention. In one embodiment of the present invention, T7 RBS from bacteriophage T7 may be used.

In the present invention, the transcriptional terminator may preferably be rrnBT1T2 or tL3. In addition, any transcriptional terminator that is conventionally used in the art may be used in the present invention.

In the present invention, the reporter gene may be one or more selected from among fluorescence proteins and antibiotic resistance genes. As the fluorescence protein, GFP, $GFP_{UV}$ or RFP is preferably used. In addition, any fluorescence protein may be used so long as it can achieve the object of the present invention. Besides, examples of an antibiotic resistance gene that may be used in the present invention include conventional antibiotic resistance genes, including kanamycin, chloramphenicol, and tetracycline.

In one embodiment of the present invention, the reporter gene may be a dual reporter consisting of both a fluorescence protein and an antibiotic resistance gene, or a multiple reporter consisting of two or more genes. According to the present invention, the metagenomic library and the phenol-sensing artificial genetic circuit are stepwise transformed into a suitable microbial host. The transformation may be carried out using any known method. In order to increase the efficiency of the transformation, electroporation may preferably be used.

In the present invention, a gene encoding the enzyme to be screened may be provided in the form of a clone or genetic library. For example, it may be provided in the form of a single gene, a genomic library, a metagenome or a metagenomic library, which can be applied in the molecular biological field. In addition, the single gene may be provided in a form in which it is contained in a vector or a microorganism.

In the present invention, the artificial genetic circuit may be provided in the form of a vector or a microorganism. In the present invention, the microorganism may preferably be E. coli, yeast, a plant cell or an animal cell. Also, a cell-free extract obtained from such cells may be used.

According to the present invention, the microorganism transformed with the genetic circuit is treated with one or more substrates selected from among phenol-release compounds capable of liberating phenols by an enzymatic reaction. Preferably, in order to optimize the enzymatic reaction, the time of addition of the substrate can be controlled such that the cell growth step and the step of activating the genetic circuit are separated from each other. For example, the step of treatment with the substrate may consist of the steps of: collecting a healthy microorganism grown in nutrient medium; and treating the collected microorganism with the substrate in minimal medium.

The nutrient medium or minimal medium may be any medium which can generally be used in the art.

Preferably, the transformed microorganism recognizing phenols is treated with the substrate when the cells reach an $OD_{600}$ of about 1.5-4, whereby the enzyme activation reaction can be optimized. More preferably, the activation reaction is performed for 14-16 hours, whereby the enzymatic reaction can be optimized.

The transcriptional regulatory protein is $\sigma^{54}$-dependent and operates well in an environment in which nutrient components are limited (Sze et al., (1996) J. Bacteriol. 178: 3727-3735). For liquid culture, in LB medium, growth rate is high, but the reactivity of the genetic circuit is low. On the contrary, in M9 medium, reactivity is high, but growth rate is slow. For these reasons, LB and M9 media are not suitable for high-throughput screening. Also, when the substrate is added at the initial stage of culture, an enzymatic reaction will occur as the cells grow, whereby an error in the comparison of enzymatic activity will occur due to the difference in growth between the cells. In order to overcome these shortcomings, in an embodiment of the present invention, the time of addition of the substrate is controlled such that the cell growth step and the step of activating the artificial genetic circuit are separated from each other as follows, thereby optimizing the enzymatic reaction: 1) cell growth step of shake-culturing cells using LB medium rich in nutrients at 37° C., and then collecting the cells at a cell concentration ($OD_{600}$) of about 1.5-4; and 2) artificial genetic circuit-activating step of subjecting the collected cells to an enzymatic reaction using a substrate-containing M9 medium at 30° C. for 14-16 hours.

In the present invention, the "phenol-release compound" serves as a substrate that can be used to detect intracellular enzymatic activity. It is a compound capable of releasing phenol by an enzymatic reaction. Specifically, it is a compound capable of releasing the following phenolic compounds by an enzymatic reaction: phenol, 2-chlorophenol, 2-iodophenol, 2-fluorophenol, o-cresol, 2-ethylphenol, m-cresol, 2-nitrophenol, catechol, 2-methoxyphenol, 2-aminophenol, 2,3-dichlorophenol, 3-chlorophenol, 2,3-dimethylphenol, 3-nitrophenol, 4-chlorophenol, p-cresol, 2,5-dichlorophenol, 2,5-dimethylphenol, etc. This compound is also called a "phenol-tag substrate".

Examples of the phenol-release compound capable of liberating phenol by an enzymatic reaction, that is, the phenol-tag substrate, include phenolic compounds containing ester (—OOC—), ether (—OC—), glycoside (—O-Glc)

or phospho-ester (—O—PO₃), which substitutes for the hydroxyl group (—OH) of phenol, as well as phenol derivatives containing an alkyl (—CH₃), hydroxyl (—OH), carboxyl (—COOH), amino (—NH₂), thiol (—SH), amide (—NH—CO— or —CO—NH—), sulfide (—S—SH) or halogen group (—Cl, —Br, —F) at the ortho-, meta- or para-position, and or benzene ring compounds.

Specifically, examples of the phenol-tag substrate that is used in the present invention may include various phenol derivatives having a phenol group covalently coupled thereto. For example, when a phenolic compound containing ester (—OOC—), ether (—OC—), glycoside (—O-Glc) or phospho-ester (—O—PO₃), which substitutes for the hydroxyl group of phenol, is used as the substrate, it can be used to detect esterase, lipase, glycosidase, phosphatase or phytase activity. In addition, the phenol-tag substrate may be a substance prepared by introducing new methyl (—CH₃), hydroxyl (—OH), carboxyl (—COOH), amino (—NH₂) or thiol (—SH) into the ortho-, meta- or para-position. When a phenolic compound having amide (—NH—CO— or —CO—NH—) or sulfide (—S—SH) at the ortho-, meta- or para-position is used as the substrate, the phenolic compound having the amide group can be used to detect amidase or peptidase activity, and the phenolic compound having the sulfide group can be used to detect the activity of oxido-reductase.

In addition, when a phenolic compound having a new carbon bond coupled thereto, that is, Ph-C—(R), is used as the phenol-tag substrate, it can be used to detect the activity of phenol-lyase that breaks the carbon bond to liberate phenol. The phenol-tag substrate may also be a benzene ring compound that can detect the activity of oxygenase such as monooxygenase or dioxygenase, which is involved in the oxidation of aromatic compounds. A phenol compound containing a halogen, such as chlorine (Cl), bromine (Br) or fluorine (F), coupled thereto, may also be used as the substrate. In this case, the activity of enzymes that acts on the halogenated phenolic compound to dehalogenate or isomerize the compound can be detected according to the present invention.

In addition, the activity of transferase transferring a covalent bond from the above-mentioned phenolic compound to other organic molecules or the activity of ligase producing a new covalent bond can also be detected according to the same principle as described above in the present invention.

Thus, the use of various phenol-tag substrates as described in the present invention allows detection of intracellular hydrolase, oxido-reductase, isomerase, lyase, transferase and the like. The substrates that are used to detect intracellular enzymatic activity in the present invention refer to phenol-tag compounds, including various synthetic substrates such as phenol, o/p-nitrophenol, o/p-chlorophenol, etc. When a suitable enzyme acts on such phenol-tag compounds, phenol will be liberated from the phenol-tag compounds. For example, when *E. coli* β-galactosidase (lacZ) acts on phenyl-β-glucoside, the phenol compound will be liberated by the activity of the enzyme. Table 1 below shows examples of the characteristics of phenol-tag substrates and related enzymatic reactions.

TABLE 1

| Phenol-Substrates | | X-Groups | Target Enzymes |
|---|---|---|---|
| Ph-O-X | Ph(OH)-O-X | α β-glycosides, phosphate, phosphoro-thioate | α β-glycosidase, cellulase, glycosylceramidase, phosphatase, phytase |
| Ph-O-C(=O)X | Ph(OH)-O-C(=O)X | alkyl, amine | esterase, lipase, urethanase |
| Ph-NH-X | Ph(OH)-NH-X | alkyl, amino acids | amidase, peptidase, proteinase |
| Ph(OH)-S-SX | | alkyl, amino acids | oxidoreductases |
| Ph(OH)-X | | amino acids, pyruvate, halogen (Cl, Br, F) | phenol-lyase, dehalgenase, isomerase |

TABLE 1-continued

| Phenol-Substrates | X-Groups | Target Enzymes |
| --- | --- | --- |
| 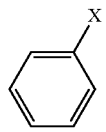 | alkyl, B(OH)$_2$ | mono-, di-oxygenases |

Specifically, when any enzymatic gene is introduced into a recombinant microorganism containing the artificial genetic circuit recognizing phenol and then the microorganism is treated with the phenol-tag substrate, the concentration of the phenolic compound will change depending on the function and activity of the enzymatic gene in the cells. Thus, when an increase in the amount of a reporter gene (such as fluorescence or antibiotic resistance reporter) by the expression inducing function of the phenolic compound is measured using various techniques such as fluorescence analysis or antibiotic resistance analysis, intracellular and extracellular enzymatic activities can be detected with high sensitivity. Also, the fluorescence protein or antibiotic resistance protein that is used as the reporter in the present invention can be measured using a high-sensitivity measurement method and is defined in a cell without passing through the cell membrane, and thus the property of a foreign gene that is expressed in the cell is individually exhibited. Thus, because a single cell acts as an independent reactor or analyzer, the activity of the reporter whose expression was induced by sensing the phenolic compound liberated by the enzymatic reaction can be measured using fluorescence-activated cell sorting (FACS), microcolony-fluorescence image analysis, fluorescence spectrum analysis or antibiotic selective medium, which can analyze several million to several ten million samples.

As used herein, the term "environmental sample" refers to a sample from an environment such as soil or seawater.

In the present invention, the metagenomic library can be constructed by introducing soil-derived DNA into a vector selected from the group consisting of plasmids, fosmids, cosmids, BAC and YAC.

Figure 2A:
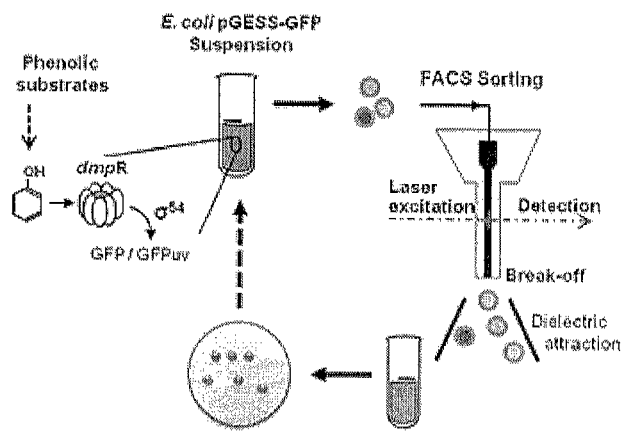
FIG. 2A shows high-throughput screening of the metagenomic library using the fluorescence protein reporter.

In the present invention, when a fluorescence protein is used as the reporter, microorganisms are treated with the substrate to perform an enzymatic reaction, and then high-throughput screening of microorganisms having fluorescence is performed using the fluorescence-activated cell sorter (FACS). The FACS is very suitable for the object of the present invention, because it allows the analysis and recovery of library strains in high throughput (~10$^6$ cells/min). The recovered strains are plated on a solid-state substrate plate (~10$^3$ cells/90 mm Petri dish), and strains having enzymatic activity are finally selected using a fluorescence microscope (see FIG. 2A).

Figure 2B:
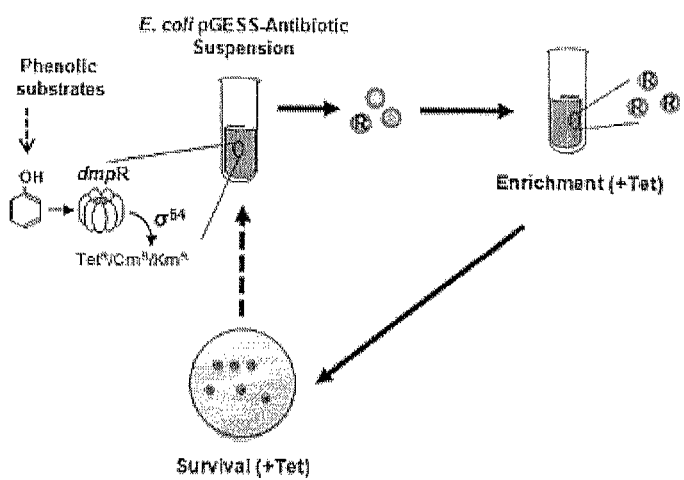
FIG. 2B shows high-throughput screening of the metagenomic library using the antibiotic resistance protein reporter.

When an antibiotic resistance protein is used as the reporter, strains are cultured in antibiotic-containing liquid medium such that only strains having enzymatic activity can grow. Finally, only strains having enzymatic activity are enriched in the culture medium. The cultured strains are plated on an antibiotic-containing solid substrate plate (~10$^3$ cells/90 mm; Petri dish), and strains having enzymatic activity are finally selected by observation of living colonies (see FIG. 2B).

When a dual reporter is used as the substrate, it may be a combination of the fluorescence reporter and the antibiotic resistance protein. It has an advantage in that false positive clones that can occur in high-throughput screening can be eliminated.

In the present invention, in order to recover a pure fosmid gene including a target gene excluding the artificial genetic circuit (pGESS-GFP) from selected microbial cells, the following three methods can be used.

Figure 3A:
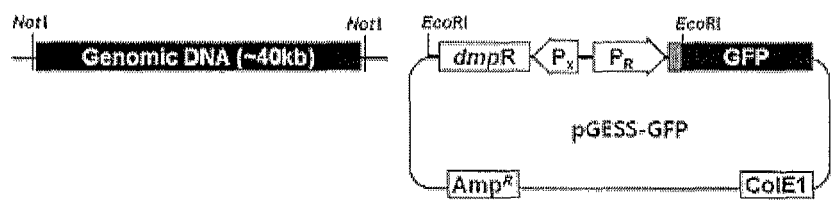
FIG. 3A shows a method of collection by treatment with restriction enzymes.

The first method is a method of treating the vector with restriction enzymes to remove artificial genetic circuit-containing DNA and recover the fosmid gene. Specifically, the vector is digested with restriction enzymes such as Not I and EcoR I into 2-3 fragments, and then the gene of the fosmid vector is recovered by gel electrophoresis (see FIG. 3A).

Figure 3B:
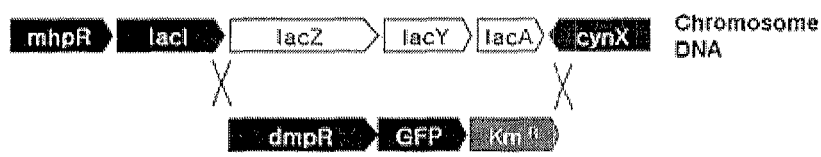
FIG. 3B shows a method of using microorganisms having introduced therein an artificial genetic circuit.

The second method is a method of constructing and using a microbial strain having the artificial genetic circuit introduced in its chromosomal system. According to this method, only the metagenomic gene-containing fosmid gene can be recovered without removing the artificial genetic gene, a plasmid-based homology problem can be avoided. Thus, this method makes it possible to construct more stable high-throughput screening technology (see FIG. 3B).

Figure 3C:
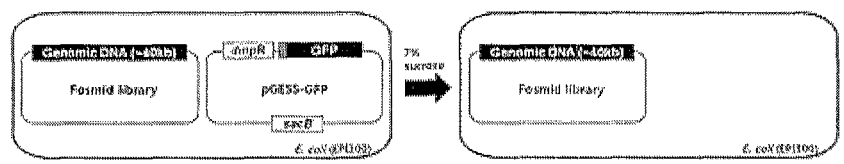
FIG. 3C shows a method of collection following a curing process performed by introducing a suicide gene into the artificial genetic circuit.

The third method is a method of introducing a suicide gene into the artificial genetic circuit. According to this method, the artificial genetic circuit having the suicide gene introduced therein can be lost by an additional curing process during the recovery of the fosmid gene, whereby only the fosmid gene can be recovered (see FIG. 3C).

According to the present invention, the identification of useful genes can be performed by any sequencing method known in the art. After the DNA and amino acid sequences have been analyzed, the information of the recovered gene can be obtained by the analysis of base homology in a databank (http://blast.ncbi.nlm.nih.gov).

Figure 4:
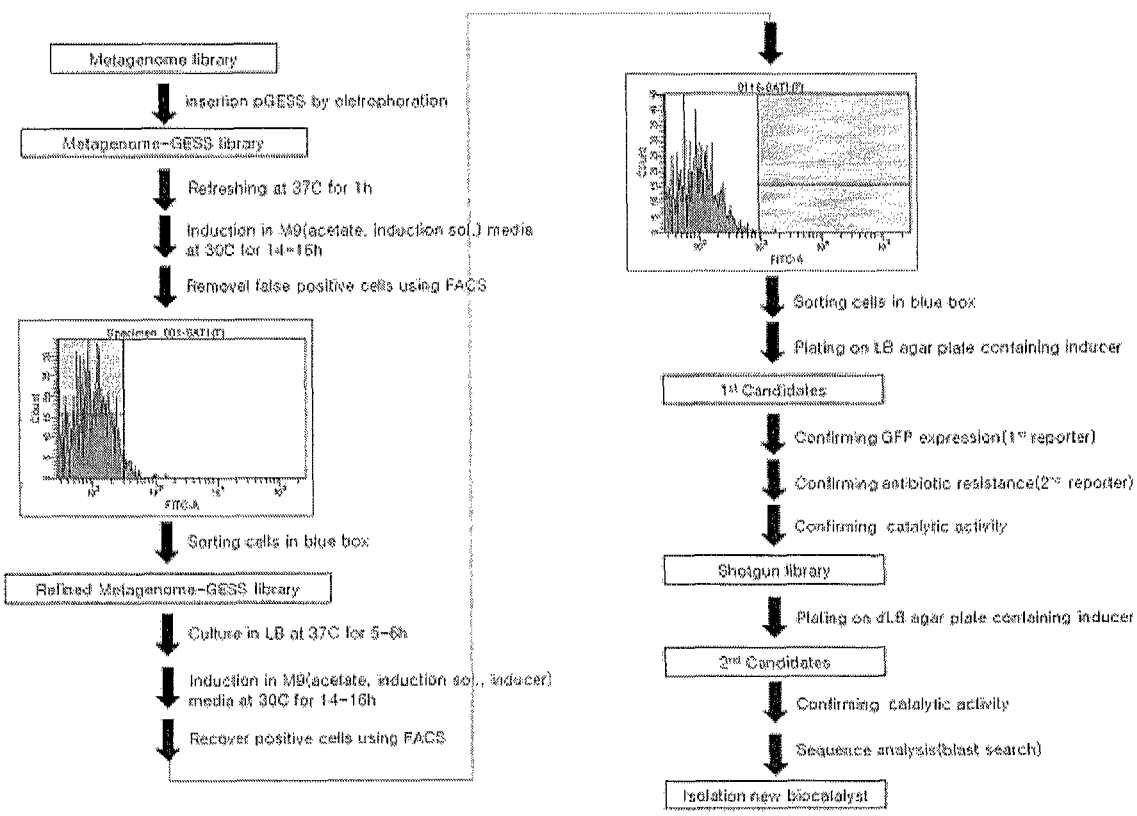
FIG. 4 shows a method of performing high-throughput screening of an enzymatically active gene from a metagenomic library using GESS (genetic enzyme screening system).

In a specific embodiment of the present invention, screening of a target enzyme from a metagenomic library using the artificial genetic circuit can be performed according to the process shown in FIG. 4.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1: Construction of Artificial Genetic Circuit Based on the Expression Regulator dmpR Detecting Phenol An artificial genetic circuit comprises a phenolic compound-degrading enzyme regulatory protein region, a gene expression regulatory region comprising promoters, and at least one reporter region selected from fluorescence proteins and antibiotic resistance genes.

An artificial genetic circuit (pGESS-FP) based on the plasmid pUC19 was constructed using *Pseudomonas putida*-derived phenol catabolic dmp operon as the phenolic compound-degrading enzyme regulatory protein detecting phenol, *P. putida* RBS as the region regulating the expression of the regulatory protein, and fluorescence protein (FP) as the reporter protein.

In the present invention, in order to construct the phenol-sensing artificial genetic circuit comprising EGFP (enhanced green fluorescence protein) gene as the reporter, a pMGFP plasmid (Ha et al., (2007) *Appl. Environ. Microbiol.* 73(22): 7408-7414) was digested with EcoR I and Hind III restriction enzymes to obtain a 720-bp EGFP fragment which was then introduced into a pUC19 vector, thereby constructing pUGFP.

In the present invention, PCR amplification was performed in *Pseudomonas putida* KCTC 1452 using forward and reverse primers (SEQ ID NO: 1 and SEQ ID NO: 2), thereby preparing a 2,157-bp DNA fragment (SEQ ID NO: 21) comprising a dmpR gene (1,692 bp) containing an EcoR I restriction enzyme linker, a dmp operator-promoter region, a portion (42 bp) of dmpK gene and a restriction enzyme sequence (12 bp) inserted during cloning. The dmpK gene was located (1,693-2,097 bp) 405-bp apart from dmpR, and the reporter gene was located 42-bp behind from the N-terminus of dmpK.

```
SEQ ID NO: 1:
5'-CCGGAATTCGAGCTGATCGAAAGTCGG-3'

SEQ ID NO: 2:
5'-CCGGAATTCCTAGCCTTCGATGCCGAT-3'
```

Figure 5:
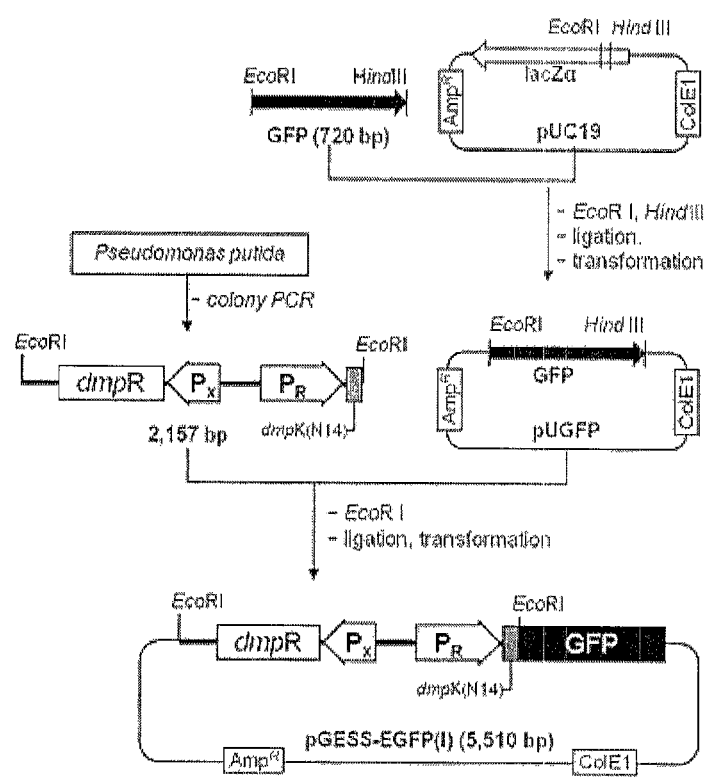
FIG. 5 shows a process of constructing pGESS-EGFP(I) containing a fluorescence protein (EGFP) as a reporter.

The N-terminal fragment of dmpK was allowed to remain in order to stably maintain the transcription enhancer function of the dmp operator-promoter region even if various fluorescence proteins or antibiotic resistance proteins were used as the reporter. The PCR product was cloned into the EcoR I site of pUGFP, thereby constructing pGESS-EGFP (I) (5,510 bp) (see FIG. 5).

In order to improve the expression of the reporter protein in the host *E. coli*, pGESS-EGFP(II) comprising *E. coli* RBS (T7 RBS) (Simons et al., (1984) *Proc. Natl. Acad. Sci. U.S.A.* 81: 1624-1628) and a transcriptional terminator, in addition to pGESS-EGFP(I) having *Pseudomonas* RBS, were constructed. *E. coli* T7 RBS was introduced before the reporter in the following manner. GFP gene was amplified by PCR using primers of SEQ ID NOS: 3 and 4 having 14-bp T7 RBS as a homologous sequence, and the PCR product together with DNA of pGESS-EGFP(I) which has digested with BsrG I restriction enzyme was introduced into *E. coli* DH5α containing a pKD-Cm vector, whereby T7 RBS in place of dmpK gene was introduced by a homologous recombination method.

```
SEQ ID NO: 3:
5'-GCACAGCTGTTGCACTTTGTCCTGCGCAATCCGCCAACCTGGAGA

AGGAGATATACATATGGTGAGCAAGGGCGAGGAGC-3'

SEQ ID NO: 4:
5'-GATTTAATCTGTATCAGGCTGAAAATCTTCTCTCATCCGCCAAAA

CAGAAGCTTACTTGTACAGCTTGTCC-3'
```

The homologous recombination was performed by preparing host cells and inserting a linearized gene (Zhang et al., (2000) *Nat. Biotech.* 18: 1314-1317; Zhang et al., (1998) *Nat. Genet.* 20: 123-128; Seung-Koo Lee et al. (2005) Korean Patent Application No. 10-2005-0116672). A single colony of *E. coli* DH5α containing a pKD46-Cm vector encoding λ-red recombinase was inoculated into 3 ml of LB liquid medium containing 25 µg/ml of chloramphenicol and cultured with shaking at 30° C. for 16 hours. The culture broth was inoculated into 100 ml of LB liquid medium (containing 25 µg/ml of chloramphenicol and 50 mM arabinose) at a concentration of 1% (v/v) and cultured with shaking at 30° C. until the cell concentration ($OD_{600}$/ml) reached 0.5-0.6. After completion of the culture, competent cells for electroporation were prepared (Molecular Cloning: A Laboratory Manual, Joseph Sambrook, David W. Russell), after which 10 ng of pGESS-EGFP(I), digested with BsrG I restriction enzyme, and 100 ng of a PCR product of GFP introduced with T7 RBS were added to the competent cell and subjected to electroporation (18 kV/cm, 25 µF). Then, 1 ml of SOC medium was added thereto and the homologous recombination of the cells was induced at 25° C. for 20 hours. The cells were plated on LB solid medium containing 50 µg/ml of ampicillin and then cultured overnight at 37° C. to select pGESS-EGFP(II). For reference, the pKD46-Cm vector contains a temperature sensitive origin of replication, and thus is removed at 37° C., so that cells having pGESS-EGFP(II) gene alone introduced therein are obtained.

425 bp of a rrnBT1T2 transcriptional terminator from pHCEIIB (BioLeaders, Korea) was amplified by PCR using primers of SEQ ID NOS: 5 and 6, and the 2,831-bp PCR product comprising dmpR, dmp operator-promoter, T7 RBS and GFP reporter protein region from pGESS-EGFP(I) was amplified using primers of SEQ ID NOS: 7 and 8, thereby preparing two DNA fragments. Overlap PCR was performed using the two DNA fragments as a template with primers of SEQ ID NOS: 5 and 8, whereby the two fragments were ligated with each other.

Figure 6:
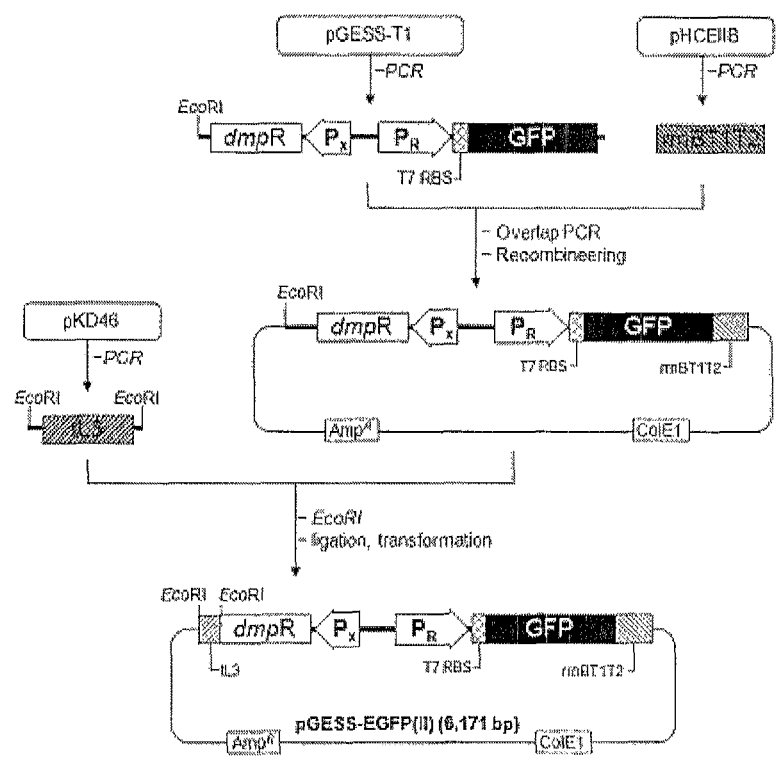
FIG. 6 shows a process of constructing pGESS-EGFP(II), which contains a fluorescence protein (EGFP) as a reporter and has the T7 RBS and transcriptional terminator introduced in a genetic circuit.

The resulting fragment was replaced into the original pGESS-EGFP(I) by a homologous recombination method. Then, the vector eas digested with EcoR I, after which a tL3 transcriptional terminator obtained from the pKD46 vector by PCR amplification using primers of SEQ ID NOS: 9 and 10 was ligated to the C-terminus of dmpR and introduced into *E. coli* by electroporation, thereby constructing 6,171-bp pGESS-EGFP(II) (see FIG. 6).

```
SEQ ID NO: 5:
5'-ATGGACAAGCTGTACAAGTAAGCTTCTGTTTTGGCGGATGAGAGA

AGA-3'

SEQ ID NO: 6:
5'-AGCGGATAACAATTTCACACAGAAACAGCTATGACCATGATTACGC

CAAGAGTTTGTAGAAACGCAAAAAGG-3'

SEQ ID NO: 7:
5'-TCTCTCATCCGCCAAAACAGGAATTCCTAGCCTTCGATGCCGATT

T-3'

SEQ ID NO: 8:
5'-TCTTCTCTCATCCGCCAAAACAGAAGCTTACTTGTACAGCTTGTC

CAT-3'

SEQ ID NO: 9:
5'-CCCGAATTCTTCTTCGTCTGTTTCTACTG-3'

SEQ ID NO: 10:
5'-CCCGAATTCAATGGCGATGACGCATCCTCA-3'
```

Also, in the present invention, in order to GFP$_{UV}$ gene advantageous for visual observation as the reporter in the system of the present invention, EGFP of pGESS-EGFP(I) was replaced with GFP$_{UV}$ to prepare pGESS-GFP$_{UV}$(I). Specifically, 717 bp GFP$_{UV}$ gene from pGFP$_{UV}$ (Clontech, USA) was amplified by PCR using forward and reverse primers of SEQ ID NOS: 11 and 12 and introduced into pGESS-EGFP(I) by homologous recombination.

```
SEQ ID NO: 11:
5'-CGGATAACAATTTCACACAGGAAACAGCTATGACCATGATTACGC

CAAGCTTATTTGTAGAGCTCATCCA-3'

SEQ ID NO: 12:
5'-ACCTGGAGATGGCCGTGACCAATACCCCCACACCGACTTTCGATC

AGCTCATGAGTAAAGGAGAAGAACT-3'
```

In many cases, an antibiotic resistance gene, such as chloramphenicol, tetracycline or kanamycin, in addition to fluorescence protein, is preferably used as the reporter gene of the artificial genetic circuit. Namely, when an antibiotic resistance gene is used as the reporter, no image analysis system is required, and more than $10^6$-$10^7$ colonies can be rapidly analyzed on one solid medium.

Figure 7:
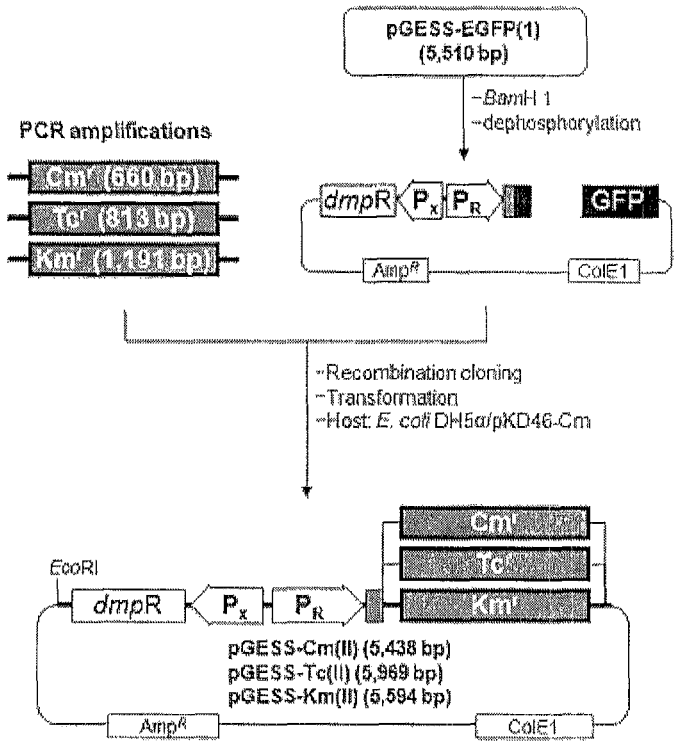
FIG. 7 shows a process of constructing pGESS-Cm(II), pGESS-Tc(II), pGESS-Km(II), which contain an antibiotic (chloramphenicol, tetracycline or kanamycin) as a reporter.
Figure 8:
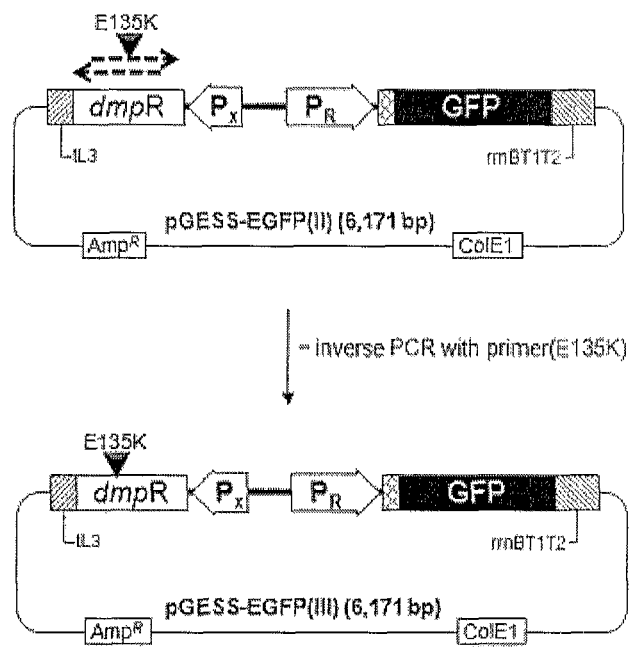
FIG. 8 shows a process of constructing pGESS-EGFP(III) substituted with mutant dmpR(E135K) in place of dmpR of pGESS-EGFP(II).

In order to construct a phenol-sensing genetic circuit comprising an antibiotic resistance gene as a reporter, chloramphenicol, tetracycline and kanamycin resistance genes were amplified by PCR using a primer set of SEQ ID NOS: 13 and 14, a primer set of SEQ ID NOS: 15 and 16 and a primer set of SEQ ID NOS: 17 and 18, respectively, thereby preparing DNA fragments of 660 bp, 813 bp and 1,191 bp, respectively. Then, the reporter region of pGESS-EGFP(II) was replaced with each of the antibiotic resistance genes by homologous recombination (see FIG. 7).

```
SEQ ID NO: 13:
5'-ACCTGGAGATGGCCGTGACCAATACCCCCACACCGACTTTCGATCA

GCTCATGGAGAAAAAAATCACTGG-3'

SEQ ID NO: 14:
5'-CGGATAACAATTTCACACAGGAAACAGCTATGACCATGATTACGCC

AAGCTTACGCCCCGCCCTGCCACT-3'

SEQ ID NO: 15:
5'-ACCTGGAGATGGCCGTGACCAATACCCCCACACCGACTTTCGATCA

GCTCATGAAATCTAACAATGCGCT-3'

SEQ ID NO: 16:
5'-CGGATAACAATTTCACACAGGAAACAGCTATGACCATGATTACGCC

AAGCTCAGGTCGAGGTGGCCCGGC-3'

SEQ ID NO: 17:
5'-ACCTGGAGATGGCCGTGACCAATACCCCCACACCGACTTTCGATCA

GCTCATGAGCCATATTCAACGGGA-3'

SEQ ID NO: 18:
5'-CGGATAACAATTTCACACAGGAAACAGCTATGACCATGATTACGCC

AAGCTTAGAAAAACTCATCGAGCA-3'
```

P-nitrophenol is widely used as a substrate to simply analyze the activity of various enzymes, including α-glycosidase, β-glycosidase, lipase and phosphatase, and thus can also be used as a highly useful phenol-tag substrate in the phenol-sensing genetic circuit of the present invention. In the present invention, in order to improve the ability of pGESS to sense p-nitrophenol, pGESS-EGFP(III) containing mutant dmpR (comprising a glutamic acid (E)-to-lysine (K) substitution at position 135 of the amino acid sequence of dmpR) was constructed in the following manner.

Specifically, the DNA sequence of dmpR was changed such that amino acid residue glutamic acid at position 135 could be replaced with lysine, after which the amino acid residue was extended by 20 bp in both directions. The resulting 40-bp sequence was subjected to point mutation using PCR primers of SEQ ID NO: 19 and SEQ ID NO: 20. Inverse PCR was performed using the pGESS-EGFP(II) plasmid as template DNA using the two primers. The inverse PCR reaction was performed using KOD DNA polymerase (Novagen, USA) under the following conditions, thereby obtaining a 6,171-bp PCR product: pre-denaturation at 94° C. for 3 min, and then 25 cycles of denaturation at 94° C. for 30 sec, primer annealing at 55° C. for 30 sec and DNA synthesis at 72° C. for 60 sec, followed by final extension at 72° C. for 5 min. The prepared PCR product was treated with Proteinase K, purified with a column (Qiagen, Germany), and then treated with Dpn I (Roche, Germany), thereby removing the plasmid used as the template DNA. Then, the sample was electrophoresed on agarose gel, and only the desired band was collected, purified with a column (Qiagen, Germany), and then transformed into E. coli DH5α (ElectroMax™-DH5α-ETM, Invitrogen, USA), thereby constructing 6,171-bp pGESS-EGFP(III).

```
SEQ ID NO: 19:
5'-GATCGACTCCTTCGAGGTGAAAATCTGCCAGACCGACCTG-3'

SEQ ID NO: 20:
5'-CAGGTCGGTCTGGCAGATTTTCACCTCGAAGGAGTCGATC-3'
```

Example 2: Selection of Optimal Host E. coli for Artificial Genetic Circuit

In the present invention, in order for pGESS to operate as intended, Pseudomonas dmpR should be heterologously expressed at a suitable level and should smoothly interact with E. coli $\sigma^{54}$-dependent transcriptional regulator (Sze et al., (1996) J. Bacteriol. 178(13): 3727-3735). Thus, the signal property of pGESS can vary depending on the biological properties and growth conditions of host microorganisms. In the present invention, in order to embody the phenol-sensing genetic circuit in a stable way, influences by i) the difference between host microorganisms and ii) the time point of induction of expression by the addition of phenol were examined to determine optimal conditions.

Figure 9A:
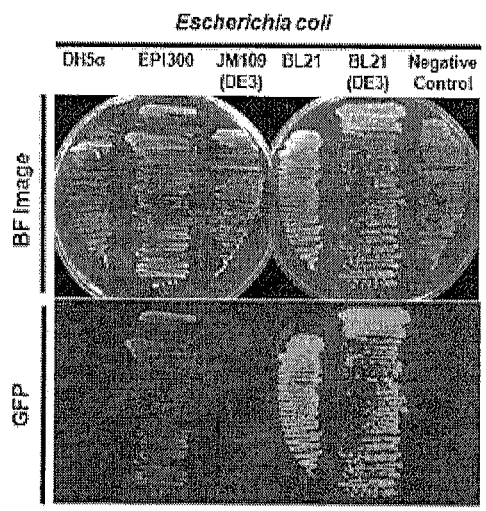
FIG. 9A is an image showing the degree of expression of fluorescence on phenol-containing solid media.

First, in this experiment, the phenol sensitivities of E. coli strains (DH5α, EPI300, JM109(DE3), BL21, and BL21 (DE3)) containing the artificial genetic circuit were examined to select a suitable bacterial strain. Specifically, LB solid medium containing 100 μM of phenol and 50 μg/ml of ampicillin was prepared, and each of E. coli strains (DH5α, EPI300, JM109(DE3), BL21, BL21(DE3)) containing pGESS-EGFP(I) and an EPI300 strain containing pGESS-Cm(II) as a control was cultured on the solid medium at 30° C. for 36 hours. FIG. 9A shows the reaction of the genetic circuit in each strain on the solid medium. As can be seen therein, the B type strains BL21 and BL21(DE3) showed higher sensitivities to the genetic circuit than the other strains. Then, the sensitivity of each E. coli strain to phenol in liquid medium was examined. Specifically, each of the pre-cultured strains was added to LB liquid medium (containing 50 μg/ml of ampicillin) at a concentration of 1%

Figure 9B:
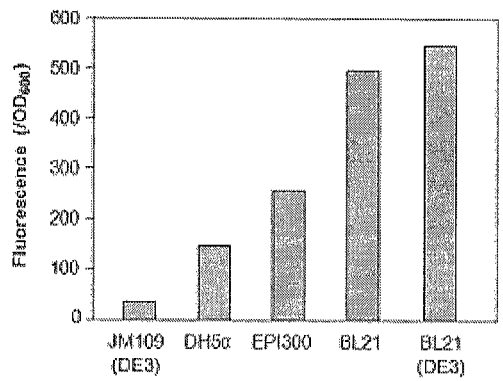
FIG. 9B is an image showing the degree of expression of fluorescence in phenol-containing liquid media.

(v/v) and then cultured with shaking at 37° C. for 8 hours. 100 µM of phenol was added to each of the cultures, which were then cultured with shaking at 30° C. for 20 hours, thereby inducing the expression of fluorescence. The analysis of fluorescence in each culture was performed in the following manner. 1.5 ml of each of the cultured strains was centrifuged and washed once with PBS buffer, and 0.5 ml of celLytic B solution (Sigma, USA), 0.2 mg/ml lysozyme (Sigma, USA) and 2-unit DNase I (Roche, Germany) were added thereto. Then, the cells were allowed to stand at 37° C. for 1 hour, and thus were lysed. The lysed cells were centrifuged, and the fluorescence intensity of the supernatant at a wavelength of 510 nm was measured with a fluorescence spectrometer (Varian, Australia) (see FIG. 9B). As a result, the same results as those in the solid culture were also obtained in the liquid culture.

Figure 9C:
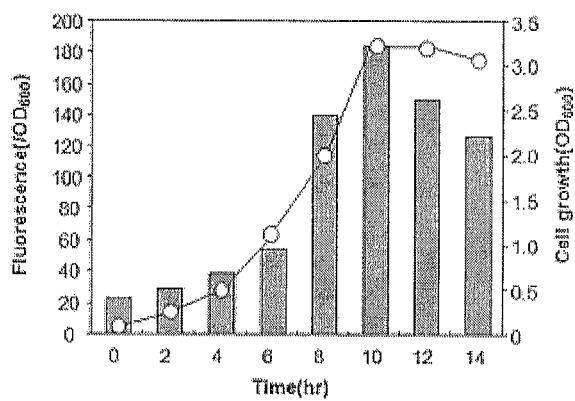
FIG. 9C shows the effect of time of addition of phenol on cell growth.

Next, the phenol reactivity of the GESS genetic circuit according to the time of addition of phenol and the cell growth state was examined. Specifically, a single colony of E. coli DH5α containing pGESS-EGFP(I) was inoculated into LB liquid medium containing 50 µg/ml of ampicillin and was cultured with shaking at 37° C. overnight. Each of the pre-cultured strains was inoculated into 100 ml of LB liquid medium containing 50 µg/ml of ampicillin at a concentration of 1% (v/v) and was cultured with shaking at 37° C. for 14 hours, while 5 ml of the culture was extracted at 2-hr intervals. A portion of the extracted culture was measured for absorbance at 600 nm to confirm the cell growth, and 100 µM of phenol was added to the remainder of the extracted culture and then allowed to react at 30° C. for 20 hours, after which the expression of fluorescence in the culture was analyzed. To analyze fluorescence, the cells were disrupted, and the fluorescence of the supernatant was analyzed using a fluorescence spectrometer. As a result, as can be seen in FIG. 9C, the intensity of fluorescence was more than 10 times different between the cell growth phases, and particularly, when phenol was added at the stationary phase, the expression of the genetic circuit was the highest. These results were consistent with the expression properties of $\sigma^{54}$.

Example 3: System Verification of Artificial Genetic Circuit and Quantitative Signal Analysis for Phenolic Compounds 1) Quantitative Analysis of Fluorescent Signal of Artificial Genetic Circuit for Phenol In order to quantitatively analyze the function of the artificial genetic circuit (constructed in Example 1) to sense phenol, a single colony of recombinant E. coli BL21 containing pGESS-EGFP(I) was inoculated into LB liquid medium containing 50 µg/ml of ampicillin and was cultured with shaking overnight at 37° C. The culture was $10^6$-fold diluted, and 100 µl of the dilution was plated on solid medium containing 50 µg/ml of amplicllin and 1-1000 µM phenol and was cultured 30° C. for 36 hours, after which the expression of fluorescence in the colony was observed with a fluorescence microscope. The fluorescence microscope was AZ100M (Nikon, Japan), and images were obtained using a CCD camera (DS-Qi1Mc, Nikon) and fluorescence filter set (GFP-HQ, Nikon) (Ex 455-485 nm, DM 495, BA 500-545), and the obtained images were processed using NIS-Elements software.

Figure 10A:
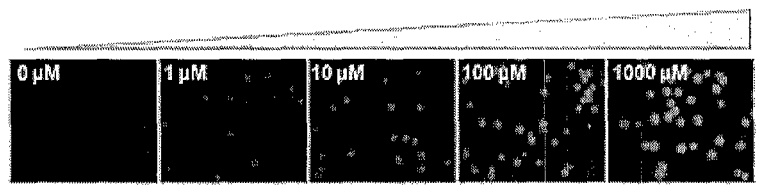
FIG. 10A shows that fluorescence intensity increases dependently on the concentration of phenol on solid medium.

As a result, as can be seen in FIG. 10A, no fluorescence was observed in the sample containing no phenol, whereas fluorescence was observed in the sample containing more than 1 µM of phenol. Also, the intensity of fluorescence increased as the concentration of phenol increased.

Figure 10B:
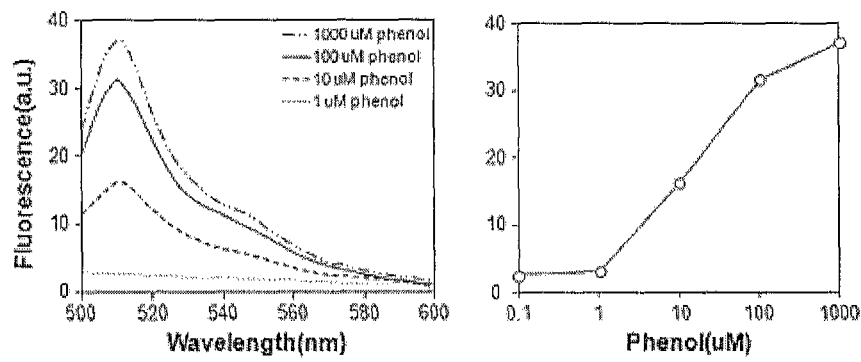
FIG. 10B shows that fluorescence intensity increases dependently on the concentration of phenol in liquid medium.

The dependence of sensitivity of the artificial genetic circuit on the concentration of the inducer phenol was confirmed using a fluorescence spectrometer. For this purpose, a single colony of recombinant E. coli containing pGESS-EGFP(I) was inoculated into LB liquid medium supplemented with 50 µg/ml of ampicillin and was cultured with shaking overnight at 37° C. The above pre-culture was inoculated into LB liquid medium containing 50 µg/ml of ampicillin and various concentrations (0.1-1000 µM) of phenol to a concentration of 1% (v/v) and was cultured with shaking at 30° C. for 20 hours. To analyze the intensity of fluorescence, the cells were disrupted, and the intensity of fluorescence in the supernatant was analyzed using a fluorescence spectrometer. As a result, as can be seen in FIG. 10B, a clear fluorescent signal was observed at a phenol concentration of 10 µM or more, and the intensity of fluorescence increased in proportion to the phenol concentration up to 1000 µM. Such results indicate that the phenol sensing genetic circuit of the present invention is quantitatively activated in the phenol concentration range of 1 to 1000 µM.

Figure 10C:
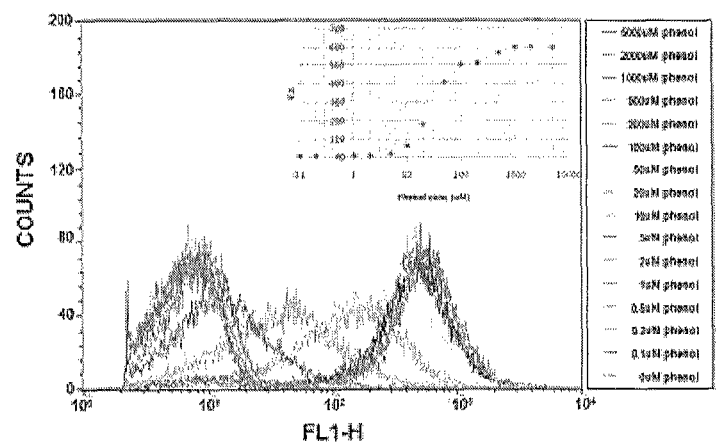
FIG. 10C shows the results of examining the phenol dependence of pGESS using FACS.

In addition, the quantitative analysis of the artificial genetic circuit for phenol was performed by FACS. A single colony of recombinant E. coli DH5a containing pGESS-EGFP(II) was inoculated into LB liquid medium containing 50 µg/ml of ampicillin and was cultured with shaking overnight at 37° C. The culture was inoculated into LB liquid medium containing 50 µg/ml of ampicillin to a concentration of 1% (v/v) and was cultured with shaking at 37° C. for 6 hours, and 2 ml of the culture was dispensed into each test tube. 0-5000 µM of phenol was added to each of the test tubes, and the culture was cultured with shaking at 30° C. for 18 hours, thereby inducing the expression of fluorescence in the culture. The intensity of fluorescence induced by each concentration of phenol was analyzed by FACS Calibur system (Becton Dickinson, USA). As a detector, a FSC, SSC, FL1-H (excitation=488 nm, emission=530/30 nm) detector was set, and data obtained by observing 10,000 sample cells were analyzed using Cell-Quest Pro (Becton Dickinson, USA). As a result, like the case of the results of analysis by the fluorescence microscope and the fluorescence spectrometer, the intensity of fluorescence was definitely distinguished between the presence and absence of phenol and increased as the phenol concentration increased (see FIG. 10C). FACS that can sense the signal as described above has a greater significance than other analysis methods, because the research of molecular evolution and the high-throughput analysis of a metagenomic library can be performed using the high-throughput analysis and sorting functions of FACS.

Next, the genetic circuits (pGESS-Cm(II), pGESS-Tc(II), and pGESS-Km(II)) comprising the antibiotic resistance gene as the reporter were used to perform quantitative antibiotic resistance analysis. A single colony of E. coli JM109(DE3) containing each genetic circuit comprising chloramphenicol, tetracycline or kanamycin resistance gene as a reporter was inoculated into liquid medium containing 50 µg/ml of ampicillin and was cultured with shaking overnight at 37° C. The pre-culture was $10^6$-fold diluted, and 100 µl of the dilution was plated on each of selective media and cultured overnight at 37° C. for 3 days. The number of colonies produced on the solid medium was counted, thereby performing the resistance test. 50 µg/ml of ampicillin and various concentrations (0, 10, 20 and 30 µg/ml) of each of selective antibiotics (chloramphenicol, tetracycline and kanamycin resistance) were added to each selective medium. Also, a transcriptional activator, that is, phenol, was added at a concentration of 1-1000 µM.

Figure 10D:
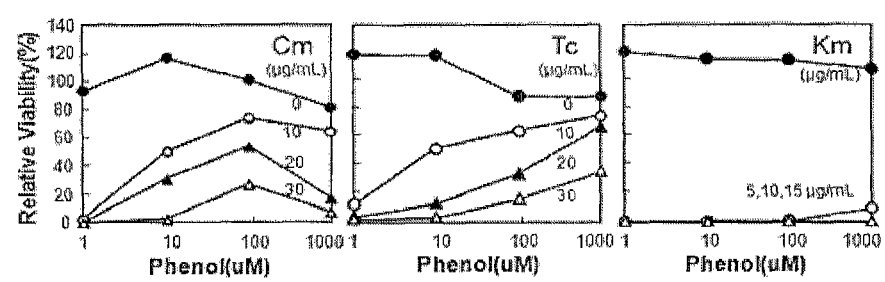
FIG. 10D shows colony counts indicating the phenol dependence of pGESS containing an antibiotic resistance protein as a reporter.

As a result, in the case of pGESS-Cm(II) comprising chloramphenicol resistance gene as the reporter, the resistance to chloramphenicol varied depending on the phenol concentration. Particularly, at a phenol concentration of 10 µM, pGESS-Cm(II) showed resistance to 20 µg/ml or less of chloramphenicol. For reference, when the phenol concentration increased to 100 µM and 1 mM, the resistances to chloramphenicol were increased to 40 µg/ml and 50 µg/ml, respectively. In the case of pGESS-Tc(II) comprising tetracycline resistance gene as a reporter, quantitative results similar to those in the case of chloramphenicol could be observed. Such results suggest that the phenol-sensing genetic circuits of the present invention can be effectively used for quantitative analysis of enzymatic activity. However, in the case of pGESS-Km(II) comprising kanamycin resistance gene as a reporter, the formation of colonies was not sensed. Thus, it was found that chloramphenicol resistance gene or tetracycline resistance gene is more preferably used as a reporter that can sense fine concentrations of phenol (see FIG. 10D).

2) Analysis of Signals of Artificial Genetic Circuit for Various Phenols

Whether the artificial genetic circuit senses the following phenol derivatives and the sensitivities of the genetic circuit to the phenol derivatives were examined: o-nitrophenol, m-nitrophenol, p-nitrophenol, o-chlorophenol, m-chlorophenol, p-chlorophenol, salicylic acid, 2-aminophenol, 2-methoxyphenol, o-cresol, m-cresol, p-cresol, catechol, resorcinol, 2-fluorophenol, 2-iodophenol, 2,4-dimethylphenol, 2,5-dimethylphenol, 3,4-dimethylphenol, 2,3-dimethylphenol, 3,5-dimethylphenol, 2,4-dichlorophenol, 2,5-dichlorophenol, 2,3-dichlorophenol, 2,6-dichlorophenol, 3,4-dichlorophenol, 3,5-dichlorophenol, 2,4-dinitrophenol, 3-methylcatechol, 2-ethylphenol, 3-ethylphenol, and benzene. Specifically, a single colony of E. coli DH5α containing pGESS-EGFP (I) was inoculated into LB liquid medium containing 50 µg/ml of ampicillin and was cultured overnight at 37° C. The culture was inoculated into LB medium containing 50 µg/ml of ampicillin to a concentration of 1% (v/v) and was cultured at 37° C. for about 8 hours until the $OD_{600}$ of the cells reached 3. Then, 100 uM of each of the phenol derivatives was added to the culture which was then cultured with shaking at 30° C. for 18 hours. 100 µl of each culture was extracted, and the distribution of fluorescence in individual cells was examined by FACS. Each of the samples was tested three times, and the measurements were averaged. As a result, as can be seen in FIG. 11A, the artificial genetic circuit strongly responded 10 compounds, including o-chlorophenol, o-nitrophenol, 2-aminophenol, 2-methoxyphenol, catechol, o-cresol, m-cresol, 2-ethylphenol, 2-fluorophenol, and 2-iodophenol, among the 31 compounds used in the experiment, and it weakly responded to m-chlorophenol, p-chlorophenol, m-nitrophenol, 2,5-dimethylphenol, 2,3-domethylphenol, 2,5-dichlorophenol, 2,3-dichlorophenol, and p-cresol, and did not respond to p-nitrophenol, suggesting that the artificial genetic circuit weakly responded to or did not respond to the compounds containing the substituent attached to the para-position of phenol.

In the case of the artificial genetic circuit comprising chloramphenicol resistance gene as the reporter, whether the genetic circuit responds to the substrates was examined. Specifically, a single colony of E. coli EPI300 containing pGESS-Cm (II) was inoculated into liquid medium containing 50 µg/ml of ampicillin and was cultured with shaking overnight at 37° C. The culture was inoculated into 50 µg/ml ampicillin-containing LB liquid medium to a concentration of 1% (v/v), and then 30 µg/ml of chloramphenicol and 100 µM of each of the phenol derivatives were added thereto and the cells were cultured with shaking at 37° C. for 8 hours. Then, the $OD_{600}$ of the cells was measured, thereby examining whether the genetic circuit responded to the phenol derivatives. As a control group, cells containing 100 µM of phenol without containing chloramphenicol were used.

As a result, the artificial genetic circuit comprising chloramphenicol resistance gene as the reporter strongly responded to o-chlorophenol, m-chlorophenol, o-nitrophenol, m-nitrophenol, catechol, 2-methoxyphenol, o-cresol, m-cresol, 2-fluorophenol, 2-iodophenol, 2,3-dimethylphenol, and 2-ethylphenol, similar to the use of the fluorescence protein, but it weakly responded to or did not respond to the compounds comprising the substituent attached to the para-position of phenol, for example, p-cresol, p-chlorophenol, and p-nitrophenol (see FIG. 11B).

As a result, it was shown that the level of expression of the fluorescence protein, that is, the degree of activation of the phenol-sensing genetic circuit, varied depending on the type and position of side chain of the phenol derivatives (see FIG. 11C).

Figure 12A:
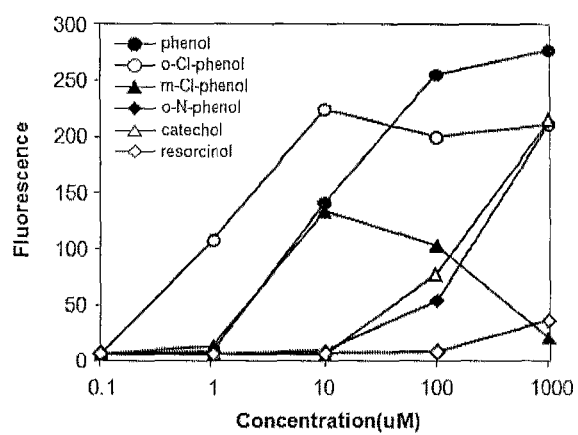
FIG. 12A shows responses obtained when using a fluorescence protein as a reporter.

3) Quantitative Analysis of Signals of Artificial Genetic Circuit for Various Phenols The signals of the artificial genetic circuit for phenolic compounds were quantitatively analyzed. Specifically, a single colony of E. coli DH5α containing pGESS-EGFP (I) was inoculated into LB liquid medium containing 50 µg/ml of ampicillin and was cultured with shaking overnight at 37° C. The culture was inoculated into LB medium containing 50 µg/ml of ampicillin to a concentration of 1% (v/v), and 0.1-1000 µM of each of phenol, o-chlorophenol, m-chlorophenol, o-nitrophenol, catechol and resorcinol was added thereto and cultured with shaking overnight at 30° C. The cells were lysed, and the supernatant was analyzed by a fluorescence spectrometer (Varian, Australia), thereby measuring the fluorescence of GFP at 510 nm. As a result, for o-chlorophenol, fluorescence was sensed even at a concentration of 0.1 µM, and for phenol and m-chlorophenol, fluorescence started to be sensed from a concentration of 1 µM. In addition, for catechol, o-nitrophenol and resorcinol, fluorescence started to be sensed from concentrations of 10 µM, 10 µM and 100 µM, respectively (see FIG. 12A). The above results suggest that the intensity of fluorescence varies depending on the kind or position of substituent and that various phenol substrates can be selectively used in order to ensure suitable measurement ranges.

Figure 12B:
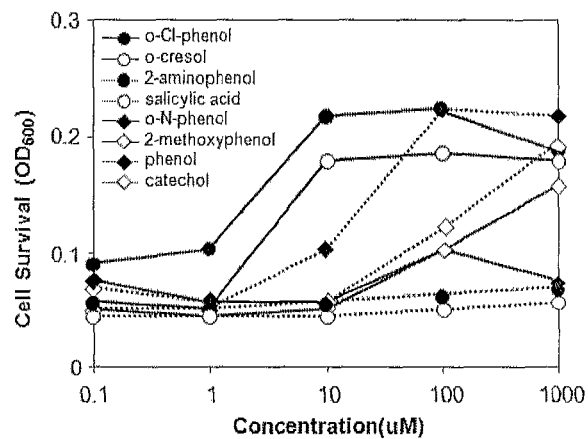
FIG. 12B shows responses obtained when using an antibiotic resistance protein as a reporter.

The quantitative analysis of the artificial genetic circuit for phenol derivatives was performed using antibiotic resistance. Specifically, a single colony of E. coli DH5α containing pGESS-Cm (II) was inoculated into LB liquid medium containing 50 µg/ml of ampicillin and was cultured with shaking overnight at 37° C. 50 µg/ml of ampicillin and 20 µg/ml of chloramphenicol were added to LB liquid medium, and 0-1000 uM of each of phenol, o-chlorophenol, o-cresol, 2-aminophenbol, salicylic acid, o-nitrophenol, 2-methoxyphenol and catechol was added to the LB medium. Then, the cultured cells were inoculated into the LB liquid medium and cultured at 37° C. for 18 hours, and whether the cells grew was observed. As a result, in the case in which the chloramphenicol resistance gene was used as the reporter, the growth of the cells varied depending on the kind or position of substituent, similar to the case of the GFP reporter (see FIG. 12B).

Figure 13A:
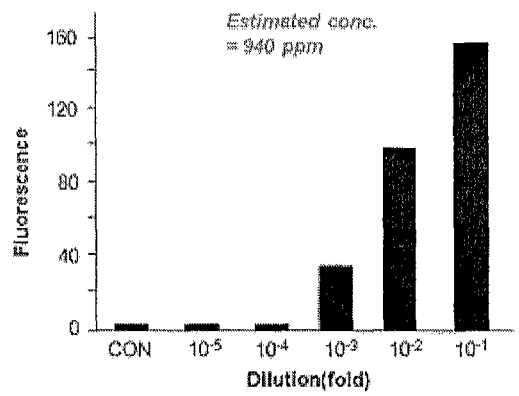
FIG. 13A shows the results of analyzing wastewater using pGESS.
Figure 13B:
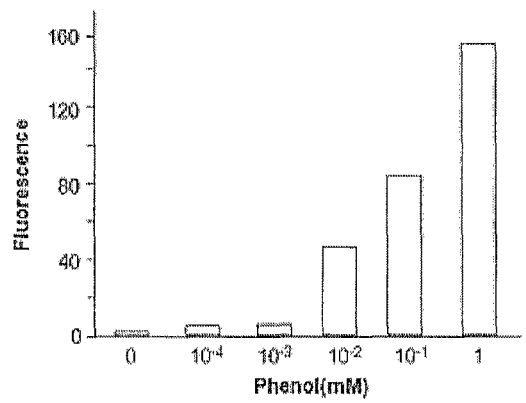
FIG. 13B shows the response of pGESS to phenol.

4) Quantitative Analysis of Signals of Artificial Genetic Circuit for Phenolic Wastewater In order to quantitatively analyze the phenol-sensing genetic circuit pGESS-EGFP (I), the analysis of concentration of phenolic compounds in wastewater containing various phenolic compounds was attempted. Specifically, a single colony of E. coli DH5α containing pGESS-EGFP (I) was inoculated into M9 liquid medium containing 50 μg/ml of ampicillin and was cultured overnight at 37° C. Then, the culture was inoculated into LB liquid medium containing 50 μg/ml of ampicillin to a concentration of 1% (v/v), coke wastewater (Shanghai, China) was diluted $10^{-1}$, $10^{-2}$, $10^{-3}$, $10^{-4}$ and $10^{-5}$ fold, added to the culture and allowed to react at 30° C. for 24 hours. Then, the cells were lysed, and the supernatant was analyzed with a fluorescence spectrometer (Varian, Australia), thereby measuring the fluorescence of GFP at 510 nm (see FIG. 13A). As a control, 0.1-1000 μM of phenol in place of coke wastewater was added and tested in the same manner as described above (see FIG. 13B).

Figure 13C:
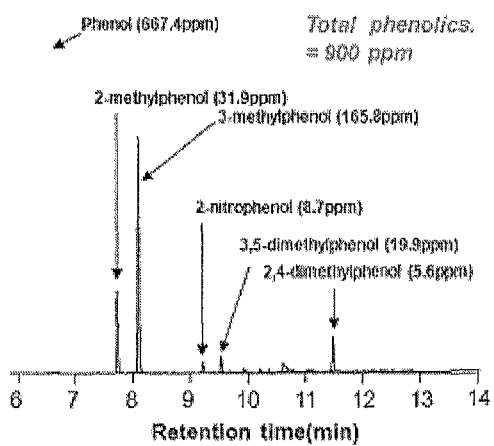
FIG. 13C shows the results of GC/MASS analysis of wastewater.

As a result, it could be observed that the intensity of fluorescence increased in proportion to the concentration of wastewater added increased. When the intensity of fluorescence was compared to the case in which phenol as the control was added, it could be estimated that the coke waste would contain about 10 mM (about 940 ppm) of phenolic compounds. Such results were consistent with the results of GC/MS analysis indicating that the wastewater contained phenol, 2-methylphenol, 3-methylphenol, 2-nitrophenol, 3,5-dimethylphenol and 2,4-dimethylphenol in amounts of 667.4 ppm, 31.9 ppm, 165.8 ppm, 8.7 ppm, 19.9 ppm and 5.6 ppm (see FIG. 13C). Thus, it was found that the phenol-sensing genetic circuit of the present invention can be used to generate quantitative signals proportional to the concentrations of phenolic components.

Example 4: Use of Artificial Genetic Circuit to Sense Intracellular Enzymatic Activity of Foreign Gene 1) Use of Artificial Genetic Circuit to Sense Enzymatic Activity The GESS genetic circuit was used to sense the activities of E. coli β-galactosidase, C. freundii tyrosine-phenol lyase (TPL), and Pseudomonas sp. methyl parathion hydrolase (MPH).

As described above, when phenyl-α/β-glycoside comprising glucoside linked to the hydroxyl group of phenol is used as a substrate, it can sense various α/β-glycosidase enzymatic activities. In the present invention, a single colony of E. coli EPI300 (Epicentre, USA) comprising a pCC1FOS™ vector containing the pGESS-GFP$_{UV}$ (I) genetic circuit and E. coli lacZ gene (β-galactosidase activity) was inoculated into LB liquid medium containing 50 μg/ml of ampicillin and 25 μg/ml of chloramphenicol and was cultured with shaking overnight at 37° C. 10 ml of the pre-culture was inoculated into LB liquid medium having the same composition as above to a concentration of 1% (v/v), and 0.1 mM phenyl-β-glycoside as a phenol-tag substrate was added thereto and incubated at 30° C. for 20 hours, after which the expression of fluorescence in the cells was measured with a fluorescence spectrometer. As a result, in the cells having β-galactosidase activity, the fluorescence of GFP was observed, but no fluorescence was observed in the cells having no β-galactosidase activity. This suggests that the pGESS genetic circuit of the present invention can be used to sense β-galactosidase enzymatic activity (see FIG. 14A).

The GESS genetic circuit of the present invention can also be used to sense a reaction (phenol-lyase) of liberating phenol from substrates (Ph-C—(R)) comprising carbon coupled to phenol. In the present invention, whether the GESS genetic circuit senses the activity of TPL (enzyme degrading tyrosine into phenol, pyruvic acid and ammonia) was examined in order to verify the effectiveness of TPL. Specifically, C. freundii TPL gene was cloned into pEC11a (obtained by replacing the on of pET11a(+) with ACYC ori) to prepare pEC-TPL which was then introduced into E. coli DH5α containing pGESS-EGFP (I).

A single colony of E. coli DH5α was inoculated into LB liquid medium containing 50 μg/ml of ampicillin and 25 μg/ml of chloramphenicol and was cultured with shaking overnight at 37° C. To LB liquid medium having the same composition as above, 1 mM IPTG (isopropyl-thio-β-D-galactopyranoside), 1 mM tyrosine and 10 μM PLP were added, and the pre-culture was added to the LB liquid medium to a concentration of 1% (v/v) and incubated at 30° C. for 20 hours, after which the expression of fluorescence in the cells was measured with a fluorescence spectrometer. As a result, the intensity of fluorescence in the cell lysis was significantly increased due to TPL activity, suggesting that the activity sensing technology of the present invention is also useful for analysis of phenol-lyase (see FIG. 14B).

Also, it was found that the GESS technology of the present invention can also sense the activity of MPH that degrades organophosphate, a wide-spectrum insecticide. Specifically, MPH gene was introduced into E. coli DH5α containing pGESS-EGFP (III) by electroporation, and the cells were pre-cultured overnight in the same manner as the above-described case of TPL. Then, 0.1 mM of methyl parathion, a phenol-tag compound that is a substrate of MPH, was added to the culture, and whether the genetic circuit sensed p-nitrophenol produced by degradation of the substrate was examined. The cells were lysed, and the supernatant was analyzed with a fluorescence spectrometer (Varian, Australia), thereby examining whether the emission wavelength of GFP was detected at 510 nm. As a result, no fluorescence was observed in the control which did not degrade methyl parathion, but strong fluorescence was observed in the presence of MPH (methyl parathion hydrolase) (see FIG. 14C).

Figure 15A:
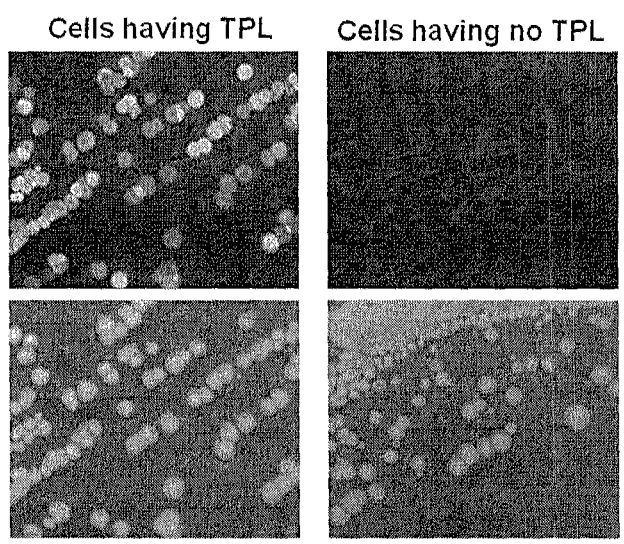
FIG. 15A shows the results of detecting the activity of TPL on solid medium using a fluorescence reporter.

2) Fluorescence Imaging, Fluorescence-Activated Cell Sorting and Antibiotic Resistance Analysis for Sensing Enzymatic Activity Using Artificial Genetic Circuit Sense of enzymatic activity by the GESS genetic circuit was observed by fluorescence images. Specifically, a single colony of recombinant E. coli containing TPL gene and pGESS-EGFP (I) was inoculated into LB liquid medium containing 50 μg/ml of ampicillin and was cultured with shaking overnight at 37° C. The pre-culture was diluted $10^6$-fold, and 100 μl of the dilution was streaked on LB solid medium containing 1 mM tyrosine, 10 μM PLP and 50 μg/ml of ampicillin and was cultured at 30° C. for 36 hours. Then, the fluorescence image of the colonies was observed with a fluorescence microscope (Nikon, Japan). As a control, a colony of E. coli containing pGESS-EGFP (I) without containing TPL gene was tested and observed in the same manner as above. As a result, no fluorescence was observed in the absence of TPL gene, but an image of the colony of E. coli containing pGESS-EGFP (I) was observed in the presence of TPL gene (see FIG. 15A).

Figure 15B:
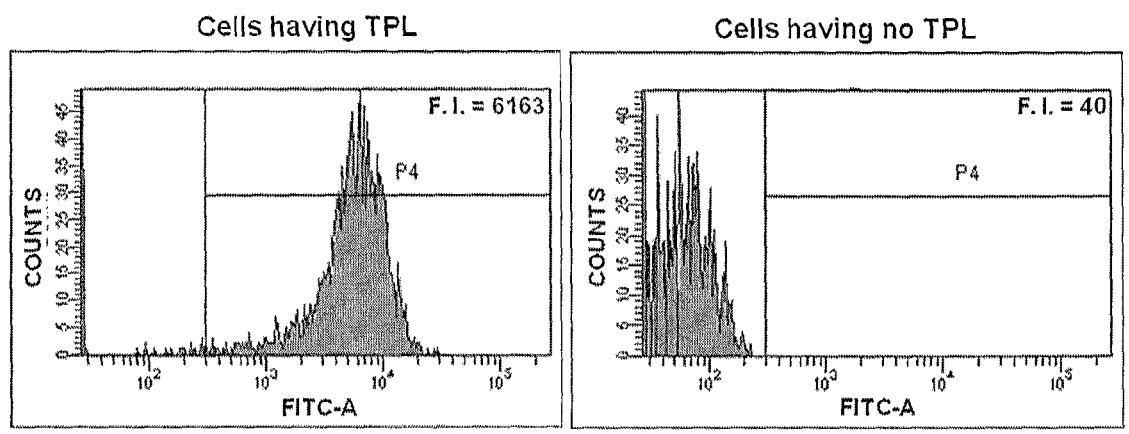
FIG. 15B shows the results of detecting the activity of TPL on liquid medium using a fluorescence reporter.

Results similar thereto could also be seen in the case in which the enzyme activity of a liquid sample was analyzed by FACS sorting. Specifically, activity was compared between recombinant E. coli containing TPL gene and pGESS-EGFP (I) and control recombinant *E. coli* containing pGESS-EGFP (I) without containing TPL gene. For this purpose, each colony was inoculated into LB medium containing 50 μg/ml of ampicillin and was cultured with shaking overnight at 37° C. The pre-culture was inoculated into LB liquid medium containing 1 mM tyrosine, 10 μM PLP (pyridoxal-5'-phosphate) and 50 μg/ml of ampicillin to a concentration of 1% (v/v) and was cultured with shaking at 30° C. for 20 hours. The measurement of fluorescence in the cultured cells was performed using FACSAria system (Becton Dickinson, USA). As a result, the distribution of fluorescence in the cell sample containing TPL was shifted to the right side compared to the distribution of fluorescence in the cell sample containing no TPL, indicating that the intensity of fluorescence in the cell sample containing TPL was higher (see FIG. 15B).

Figure 15C:
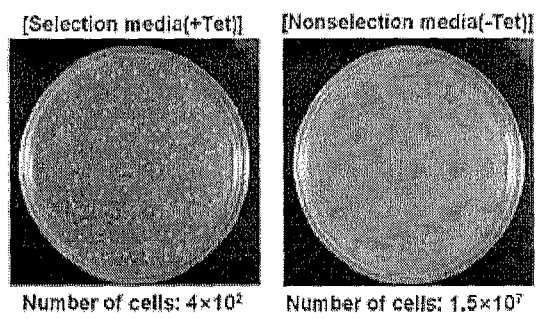
FIG. 15C shows the results of detecting the activity of TPL using an antibiotic (tetracycline) resistance protein.

Sensing of enzymatic activity by the GESS genetic circuit was observed by antibiotic resistance. Specifically, a single colony of recombinant *E. coli* containing TPL gene and pGESS-Tc (II) was inoculated into LB medium containing 50 μg/ml of ampicillin and was cultured with shaking overnight at 37° C. The culture was $10^6$-fold diluted, and 100 μl of the dilution was plated on LB solid medium containing 1 mM tyrosine, 10 μM PLP, 100 μg/ml of ampicillin and 20 μg/ml of tetracycline and was cultured at 30° C. for 36 hours, after which the pattern of proliferation of the colonies was observed. As a control, the same pre-culture as above was plated on solid medium containing no tetracycline and was observed. As a result, when there was no tetracycline, the GESS genetic circuit had no selectivity, and thus colonies proliferated throughout the medium, but when tetracycline existed, only colonies producing phenol by the enzymatic degradation of the substrate could survive. Thus, the selective sensitivity of GESS in the measurement of enzymatic activity could be seen (see FIG. 15C).

The above test results showed that the GESS system can achieve sense enzymatic activity using liquid or solid medium and can perform high-throughput analysis of enzymatic activity using not only fluorescence protein but also antibiotic resistance protein as a reporter.

3) Verification of Quantitative Ability of Artificial Genetic Circuit (GESS)

Whether different enzymatic activities can be quantitatively analyzed using the GESS was examined. As enzymes, tyrosine-phenol lyase (TPL(C)) from *Citrobacter freundii* and tyrosine-phenol lyase (TPL(S)) from *Symbiobacterium toebii* were used, and as a control, *E. coli* containing no enzyme was used. The enzymatic activity value measured using pGESS was compared with the enzymatic activity value measured using HPLC, thereby determining significance.

Specifically, each of TPL(C) and TPL(S), contained in a psHCE vector (obtained by treating pSTV28 (Takara, Japan) with Cla I and Tth111 I, and then inserting a HCE promoter from pHCEIIB (Takara, Japan) and a transcriptional terminator into the pSTV28), and a control psHCE vector was transformed into *E. coli* DH5α, thereby preparing strains having enzymatic activity. Each colony was inoculated into LB liquid medium containing 50 μg/ml of ampicillin and 12.5 μg/ml of chloramphenicol and was cultured with shaking overnight at 37° C. The culture was inoculated into M9 liquid medium containing 1 mM tyrosine, 10 μM PLP (pyridoxal-5'-phosphate), 50 μg/ml of ampicillin and 12.5 μg/ml of chloramphenicol to a concentration of 1% (v/v) and was cultured with shaking at 37° C. for 12 hours. The growth of the bacterial cells was predicted by measuring the absorbance ($OD_{600}$) using a UV/VIS spectrometer (Ultrospec 3000, Pharmacia Biotech, Sweden), and the intensity of fluorescence was measured using a fluorescence plate reader (Multi-label reader, PerkinElmer, USA).

To measure enzymatic activity, seed cells were prepared, after which they were inoculated into LB liquid medium containing 50 μg/ml of ampicillin and 12.5 μg/ml of chloramphenicol to a concentration of 1% (v/v) and were cultured at 37° C. for 24 hours. The cells were recovered from the culture medium by centrifugation (5000 rpm, 10 min) and washed once with 50 mM Tris-HCl buffer (pH 7.5). The cells were completely lysed using a sonicator (method: 3 sec disruption, 3 sec interruption, 20% intensity for 3 min; Vibra cell, Sonics, USA). To perform an enzymatic reaction, 1 mM tyrosine and 100 uM PLP were added to the cell lysis (1 mg/ml) in 100 mM potassium phosphate (pH 8.0) and incubated at 37° C. for 12 hours. The enzymatic activity was measured by HPLC (SCL-10A vp, Shimadzu, Japan) using C18 reverse column (C/N. 18R03, Chemco Pak, Japan) and 50:50 acetonitrile-water as buffer.

Figure 16A:
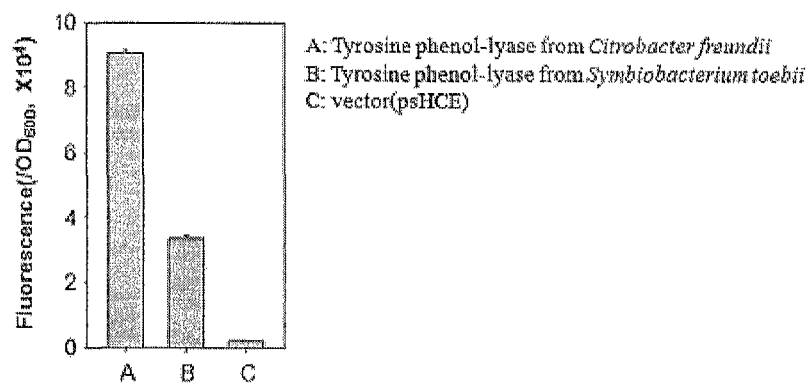
FIG. 16A shows the results of measuring the enzymatic activities of TPL from Citrobacter freundii and from Symbiobacterium toebii using pGESS.
Figure 16B:
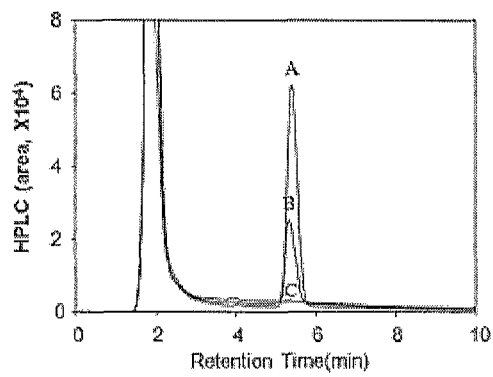
FIG. 16B shows the results of HPLC analysis of phenol produced after subjecting these strains to an enzymatic reaction.

FIG. 16A shows the activities of TPL(C), TPL(S) and psHCE analyzed by pGESS. As can be seen therein, the activity of TPL(C) was about 2.5 times higher than that of TPL(S). After the enzymatic reaction, the productions of phenol analyzed using HPLC were compared (see FIG. 16B). Like the results of pGESS, the activity of TPL(C) was about 2.5 times higher than that of TPL(S). Such results indicate that pGESS can be used to quantitatively analyze enzymes having various enzymatic activities.

Example 5: Optimization of Medium and Nutrients (Carbon Sources) for Increasing the Ability to Sense Phenol In the artificial genetic circuit according to the present invention, the phenolic compound-degrading enzyme regulatory protein that is a transcriptional regulatory protein is $\sigma^{54}$-dependent, and it is known that the nutrient conditions of media or strains influence the ability of artificial genetic circuits to sense phenol (Sze et al., (1996) *J. Bacteriol.* 178: 3727-3735). In order to optimize the ability to sense phenol, the sensitivity according to the nutrient conditions of media was examined and the sensitivity according to nutrients (carbon sources) was examined, thereby selecting an optimal medium.

Figure 17A:
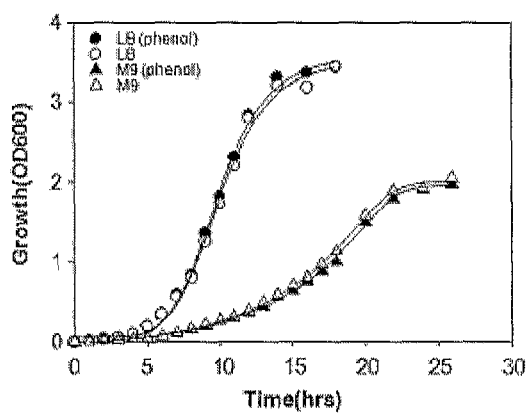
FIG. 17A shows the difference in growth rate between LB and M9 media.
Figure 17B:
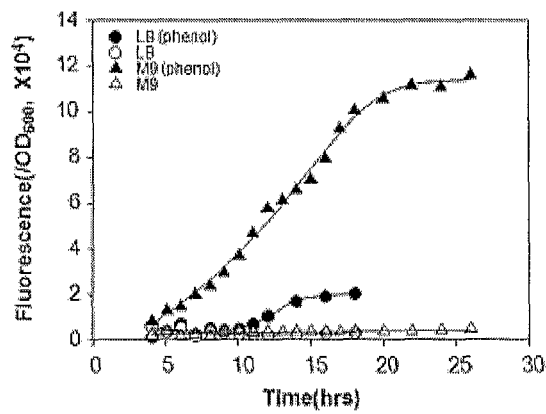
FIG. 17B shows the difference in reactivity between artificial genetic circuits.

First, cell growth and fluorescence intensity (sensitivity) according to the nutrient conditions were examined. As a strain, *E. coli* DH5α transformed with pGESS-EGFP (II) constructed in Example 1 was used, and as media, LB (per liter, 10 g tryptone, 5 g yeast extract, 10 g NaCl) and M9 (per liter, 12.8 g $Na_2HPO_4 \cdot 7H_2O$, 3 g $KH_2PO_4$, 0.5 g NaCl, 1 g $NH_4Cl$, 2 mM $MgSO_4$, 0.1 mM $CaCl_2$, 0.4% (w/v) Glucose, 0.01% (w/v) thiamine) media were used. 0.1 mM phenol was added to each medium to induce the expression of fluorescence of the artificial genetic circuit (pGESS-EGFP). In order to the inoculated strain healthy, the strain was inoculated into LB medium and was cultured with shaking overnight at 37° C. Next day, the pre-culture was inoculated into LB medium to a concentration of 3% (v/v) and cultured for about 2 hours ($OD_{600}$/ml=0.3-0.4), thereby preparing the strain at the initial exponential phase. The prepared strain culture was inoculated into 0.1 mM phenol-containing LB or M9 media to a concentration to a concentration of 1% (v/v) and was cultured with shaking at 30° C. Each medium was supplemented with 50 μg/ml of ampicillin as a selective marker. During the culture process, the culture was sampled at given time intervals, and the cell growth and fluorescence intensity thereof were examined. The cell growth was predicted by measuring the absorbance ($OD_{600}$) using a UV/VIS spectrometer (Ultrospec 3000, Pharmacia Biotech, Sweden), and the fluorescence intensity was measured using a fluorescence plate reader (Multi-label reader, PerkinElmer, USA). As a result, the cell growth was better in the LB medium (see FIG. 17A), but the fluorescence intensity (sensitivity) of the artificial genetic circuit of the present invention was higher in the M9 medium (see FIG. 17B).

Figure 18A:
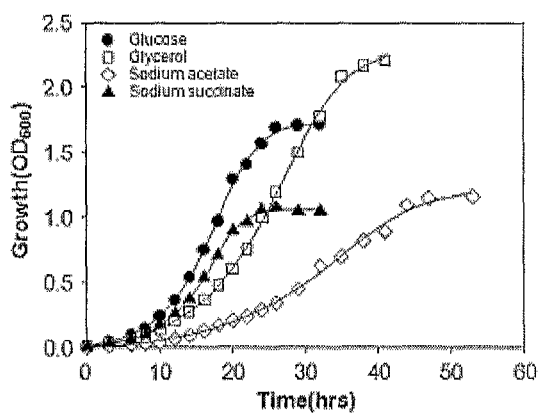
FIG. 18 shows the results of examining the effects of carbon sources of M9 medium in order to improve the ability of pGESS to detect phenol, in which FIG. 18A show the difference in growth rate between glucose, glycerol, succinate and acetate as carbon sources.
FIG. 18B shows the difference in reactivity in artificial genetic circuits.
Figure 18B:
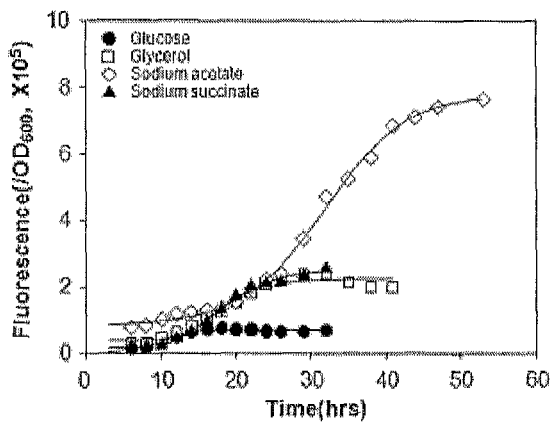

Second, cell growth and fluorescence intensity (sensitivity) according to the nutrients (carbon sources) of M9 medium were examined. As a strain, *E. coli* DH5α transformed with pGESS-EGFP (II) was used, and as basal medium, M9 (12.8 g $Na_2HPO_4.7H_2O$, 3 g $KH_2PO_4$, 0.5 g NaCl, 1 g $NH_4Cl$, 2 mM $MgSO_4$, 0.1 mM $CaCl_2$, 0.01% (w/v) thiamine) medium was used. As carbon sources, each of glucose, glycerol, Na-succinate and Na-acetate was added to the M9 medium at the same concentration of 0.4% (w/v). 0.1 mM phenol was added to the medium to induce the expression of fluorescence of the genetic circuit. Before one day, the colony was inoculated into LB medium and was cultured with shaking overnight at 37° C., and next day, the culture was inoculated into LB medium to a concentration of 3% (v/v) and cultured for about 2 hours ($OD_{600}$/ml=0.3-0.4), thereby preparing the strain at the initial exponential phase. The strain culture was inoculated into LB or M9 media containing 0.1 mM phenol to a concentration of 1% (v/v) and was cultured with shaking at 30° C. Each medium was supplemented with 50 μg/ml of ampicillin as a selective marker. During the culture process, the culture was sampled at given time intervals, and the cell growth and fluorescence intensity thereof were examined. The cell growth was predicted by measuring the absorbance ($OD_{600}$) using a UV/VIS spectrometer, and the fluorescence intensity was measured using a florescence plate reader. As a result, the bacterial cell growth ($OD_{600}$) was most rapid in the glucose-containing medium and was the highest in the glycerol-containing medium (see FIG. 18A). The fluorescence intensity (sensitivity) was the highest in the acetate-containing medium, although the growth rate was slow in the acetate-containing medium (see FIG. 18B).

Example 6: 2-Step Analysis (Growth Step-Analysis Step) of Activity for Increasing the Ability to Sense Phenol In the present invention, in order to increase the ability of the genetic circuit to sense phenolic compounds, the reaction of the genetic circuit was performed using the optimal medium and carbon source selected in Example 5, and the cell growth step and the step of activating (analyzing) the genetic circuit were separated from each other, thereby attempting the optimization of the sense system. Specifically, the bacterial cells were made healthy using LB medium during growth, and the cells were recovered and the activity of the genetic circuit therein was analyzed in the M9 medium containing acetate as a carbon source.

First, examination was made on a growth phase at which bacterial cells are to be recovered during cell culture on LB medium. As a strain, an *E. coli* DH5α strain introduced with tyrosine phenol-lyase degrading L-tyrosine was used in order to induce an enzymatic reaction liberating phenol, and as a control, an *E. coli* DH5α strain containing no tyrosine phenol-lyase was used. The two strains were introduced with the genetic circuit (pGESS-EGFP (II)). Specifically, the strains were constructed in the following manner. TPL gene (GenBank: X66978.1) from *C. freundii* was cloned into psHCE to prepare psHCE-TPL which was then introduced into *E. coli* DH5α transformed with pGESS-EGFP (II) constructed in Example 1.

Figure 19A:
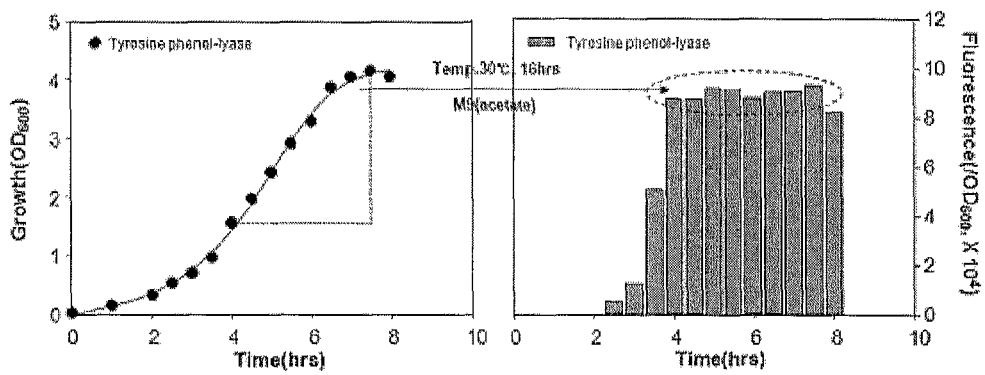
FIG. 19A shows the results of culturing each library using LB medium and examining the time point at which each library is to move from the growth step to the activating step.

The strain was inoculated into LB medium and was shakep-cultured overnight at 37° C., and next day, the culture was inoculated into LB medium to a concentration of 1% (v/v) and was cultured shake-at 37° C., while the cells were recovered at various points of time. Using the recovered cells, the activation of the genetic circuit was performed. For activation of the genetic activation, the recovered bacterial cells were washed once with M9 medium and suspended in M9 medium (acetate) containing 1 mM tyrosine and 10 μM PLP (pyridoxal 5'-phosphate) as substrates, and the cells were cultured with shaking at 30° C. for 16 hours to perform the activation of the genetic circuit. Each medium was supplemented with 50 μg/ml of ampicillin and 25 μg/ml of chloramphenicol as selective markers. The cell concentration was measured using a UV/VIS spectrometer, and the fluorescence intensity was measured using a fluorescence plate reader. As a result, it was found that, if the cells were recovered when the cell growth ($OD_{600}$/ml) reached about 1.5-4, the enzymatic reaction was stably performed (see FIG. 19A).

Figure 19B:
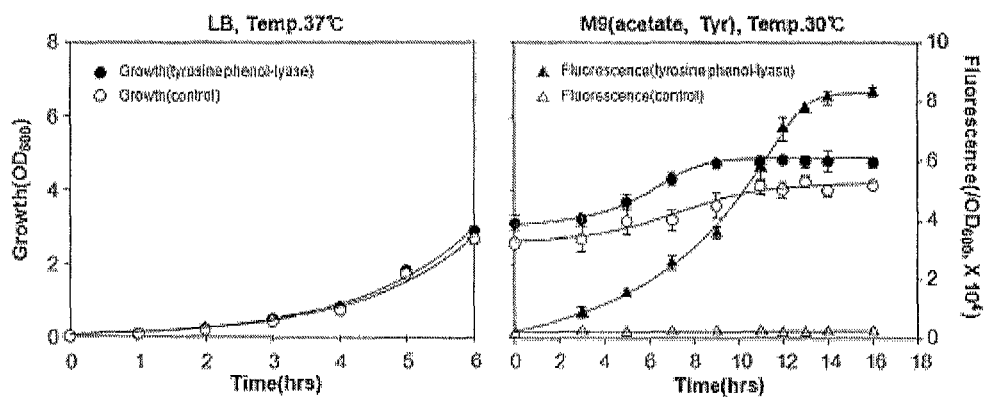
FIG. 19B shows the results of examining the time taken for the activation of the genetic circuit to reach the maximum after the cell growth step.
Figure 19C:
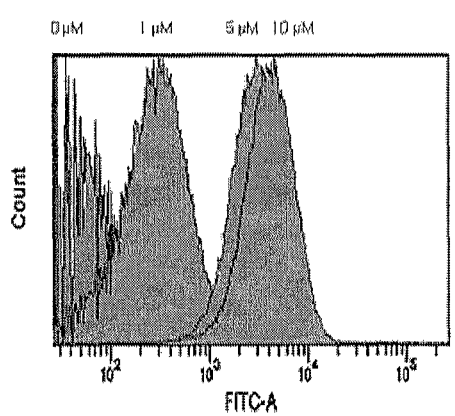
FIG. 19C shows FACS results indicating that the sensitivity of the genetic circuit to phenol was increased as a result of attempting the separation of the genetic circuit activating step.

Second, examination was made on the period of time during which the step of activating the enzymatic reaction is to be maintained on M9 medium. Specifically, the same strains as above were used, and when the cell growth ($OD_{600}$/ml) in LB medium reached about 3 (cultured for about 6 hours), the cells were recovered and subjected to washing and enzymatic reaction as described above. During the step of activating the genetic circuit, the cells were sampled, and the concentration and fluorescence intensity thereof were measured. The cell concentration was measured using a UV/VIS spectrophotometer, and the fluorescence intensity was measured using a fluorescence plate reader. As a result, it could be seen that the time during which the enzymatic reaction sufficiently occurred was 14-16 hours (see FIG. 19B).

Third, the degree of improvement in sensitivity to phenol by 2-step (growth step-analysis step) activity analysis was examined. Specifically, a colony introduced with the genetic circuit was inoculated into LB medium and was cultured with shaking overnight at 37° C., and next day, the culture was inoculated into LB medium at a concentration of 1% (v/v) and was cultured with shaking at 37° C. When the cell growth ($OD_{600}$/ml) reached about 2.5, the cultured cells were recovered and subjected to activation of the genetic circuit. For activation of the genetic circuit, the recovered bacterial cells were washed once with M9 medium, after they were suspended in M9 (acetate) media containing various concentrations of phenols and were cultured with shaking at 30° C. for 16 hours. Each medium was supplemented with 50 μg/ml of ampicillin as a selective marker. The intensity of fluorescence in cells induced by each concentration of phenol was measured using FACSAria system (Becton Dickinson, US). As a detector, an FSC, SSC, FL1-H (excitation=488 nm, emission=530/30 nm) detector was set, and data obtained by 50,000 sample cells were analyzed using FACSDiVa (Becton Dickinson, USA) (see FIG. 19 C).

Figure 19D:
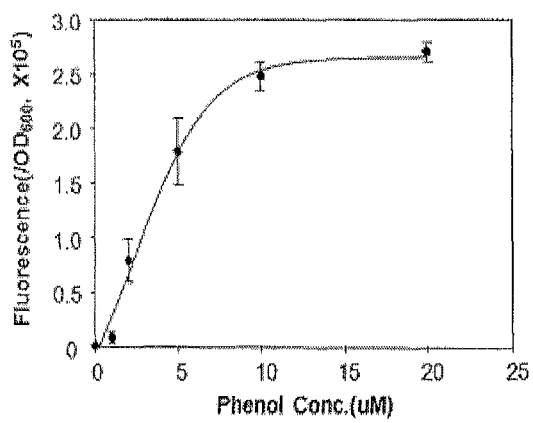
FIG. 19D is a graphic diagram showing the results of quantifying the sensitivity of the genetic circuit to phenol.

As a result, at least 1 μM phenol could be sensed by 2-step activity analysis, and the concentration range of phenol which could be quantitatively analyzed by the genetic circuit was in the range of 1-10 μM, which was about 10 times higher than the previous sensitivity, and the reaction value was about 5 times increased (see FIG. 19D).

Example 7: Improvement of Sensitivity and Recognition Specificity of Artificial Genetic Circuit (GESS)

As mentioned in the above Examples, in order to improve the sensitivity of the genetic circuit to phenolic components, the optimal medium and carbon source were selected, and the two-step method (cell growth step and genetic circuit-activating (analyzing) step) was developed, thereby performing the optimization of reaction conditions for the genetic circuit. Next, in order to increase the sensitivity and recognition specificity of the genetic circuit, the improvement of the artificial genetic circuit was performed. Specifically, a genetic circuit (pGESS-EGFP (III)) comprising mutant protein dmpR (E135K) having increased affinity for para-nitrophenol was newly developed (see Example 1) and was applied to optimized reaction conditions.

Figure 20A:
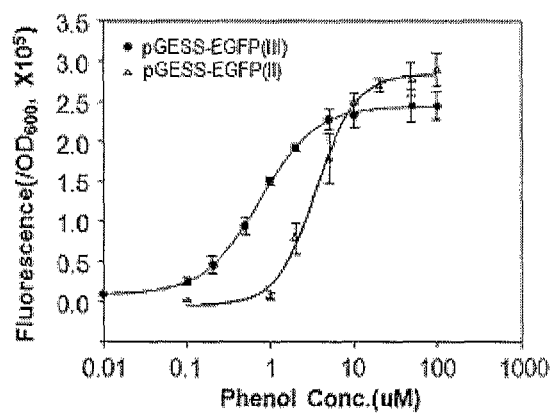
FIG. 20A shows improvements in the sensitivities of pGESS-EGFP(II) and pGESS-EGFP(III) to phenol.

The colony introduced with the pGESS-EGFP (II) or pGESS-EGFP (III) genetic circuit was inoculated into LB medium and was cultured with shaking at 37° C. Next day, the culture was inoculated into LB medium to a concentration of 1% (v/v) and was cultured with shaking at 37° C. When the cell growth ($OD_{600}$/ml) reached about 2.5, the cultured cells were recovered and subjected to activation of the genetic circuit. For activation of the genetic circuit, the recovered bacterial cells were washed once with M9 medium, after which they were suspended in M9 (acetate) media containing various concentrations of phenol and were cultured with shaking. Each medium was supplemented with 50 µg/ml of ampicillin as a selection marker. The bacterial cell growth was predicted by measuring absorbance ($OD_{600}$) using a UV/VIS spectrometer (Ultrospec 3000, Pharmacia Biotech, Sweden), and the fluorescence intensity was measured using a fluorescence plate reader (Multi-label reader, PerkinElmer, USA). As a result, when the genetic circuit was provided with mutant dmpR, the range of phenol which could be quantitatively sensed was about 0.1-10 µM, which was about 10 times higher than the case of wild dmpR, and the range of quantification also about 10 times increased (see FIG. 20A).

Figure 20B:
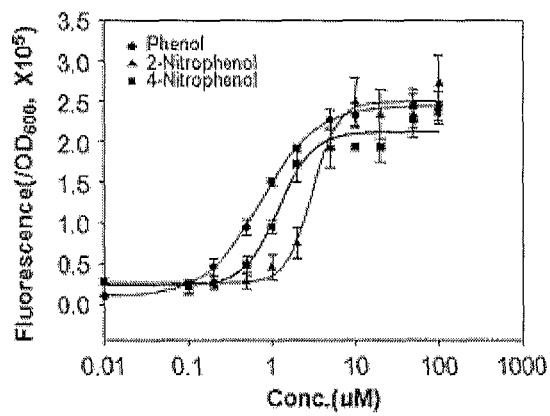
FIG. 20B shows improvements in the recognition specificities of pGESS-EGFP(III) for 2-nitrophenol and 4-nitrophenol as well as phenol.

Next, the measurement of sensitivities to 2-nitrophenol and 4-nitrophenol was performed. The measurement was performed in the same manner as above, and various concentrations of 2-nitrophenol and 4-nitrophenol in addition to phenol were added and allowed to react. As a result, sensitivity was the highest in phenol and was higher in order of 4-nitrophenol and 2-nitrophenol, and the three phenols could also be quantitatively sensed at a concentration of 0.1-10 µM (see FIG. 20B).

Example 8: High-Throughput Screening of Tyrosine Phenol-Lyase Gene from Genomic Library from *Citrobacter freundii*

It was already reported that *Citrobacter freundii*, a gram-negative bacterial strain, contains tyrosine phenol-lyase in its chromosome (Kiick et al., (1988) *Biochemistry* 27(19): 7333-7338; Demidkina et al., (1988) *FEBS Lett.* 232(2): 381-382; Chen et al., (1993) *Biochemistry* 32(43): 11591-11599). Tyrosine phenol-lyase from *Citrobacter freundii*, the expression of which is induced by TyrR, has a specific activity of about 1.9 (Chen et al., (1995) *Eur. J. Biochem.* 229(2): 540-549; Lee et al., (2006) *FEBS J.* 273: 5564-5573). In order to screen tyrosine phenol-lyase from a library based on a fosmid vector of low copy number, a high-sensitivity screening system is required.

In this Example, in order to verify the sensitivity and efficiency of the method according to the present invention, high-throughput screening of low-activity tyrosine phenol-lyase from a genomic library from *Citrobacter freundii* was attempted using the GESS system of the present invention.

The genomic library from *Citrobacter freundii* was constructed by SolGent Co., Ltd. (Korea), and the diversity of the genomic library was about $6.5 \times 10^3$. When the total chromosomal size of *Citrobacter freundii* is assumed to be about 5 Mb, the size of a chromosomal fragment which is introduced into the fosmid vector is about 30 kb. Thus, it was considered that the constructed library contains all the total chromosomes of *Citrobacter freundii*.

The artificial genetic circuit (pGESS-GFP$_{UV}$ (I)) constructed in Example 1 and the above-constructed genomic library were sequentially transformed into *E. coli* EPI300 strain (Epicentre, USA) by electroporation, thereby constructing a library whose high-throughput screening is possible. The constructed library was recovered into storage buffer and concentrated to a concentration of about $10^{10}$ cells/ml, and 0.5 ml was dispensed into each of 1.5 ml tubes and stored in a deep freezer.

Figure 21A:
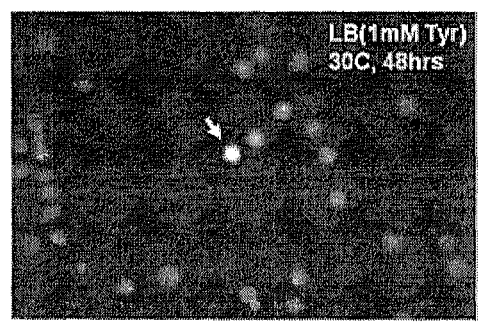
FIG. 21A shows the results of screening colonies showing the response (fluorescence) of the genetic circuit after plating a library on tyrosine-containing solid medium.

The metagenomic library stored in the deep freezer was inoculated into 3 ml of LB medium at a concentration of 1% (v/v) (about $10^8$ cells) and cultured at 37° C. for 12 hours, thereby preparing a healthy library. High-throughput screening was performed using LB medium containing 1 mM tyrosine and 10 µM PLP (pyridoxal 5'-phosphate). In order to increase the expression level of the gene introduced into the fosmid vector, 1× Copy-control solution and 50 µg/ml of ampicillin and 12.5 µg/ml of chloramphenicol were selective markers were added to the medium. The culture was suitable diluted, and the dilution was plated on the solid medium such that about 2-300 colonies (a total of 1,000 colonies) were produced. Then, the cells were cultured at 30° C. for 48 hours to induce enzymatic reactions in the cells and the expression of fluorescence. The fluorescent colonies were observed using an image analyzer (Gel Doc 2000 gel documentation system, Bio Rad, USA), and image analysis was performed using the image program (Quantity One, Bio Rad, USA) (see FIG. 21A).

Figure 21B:
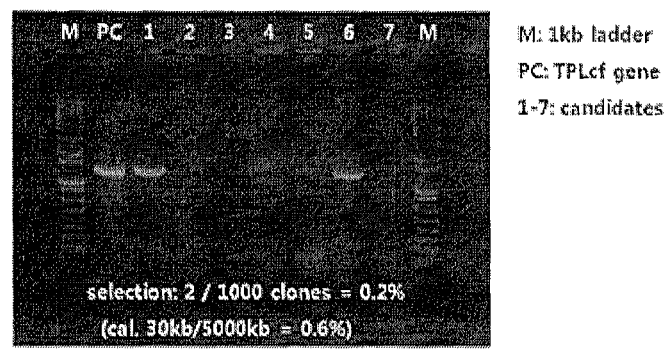
FIG. 21B shows the results of a polymerase chain reaction performed to determine whether tyrosine phenol-lyase is contained in the screened colonies.

As a result, among about 1,000 colonies, 7 colonies considered to have fluorescence were selected. Also, genes in the colonies were analyzed using polymerase chain reaction (PCR), and as a result, it was found that 2 colonies contained tyrosine phenol-lyase gene (see FIG. 21B).

When the total chromosomal size of *Citrobacter freundii* is assumed to be about 5 Mb, the size of a chromosomal fragment which is introduced into the fosmid vector is about 30 kb. Thus, the probability for tyrosine phenol-lyase to be screened was estimated to be 0.6% (6/1000 clones). The actual ratio of tyrosine phenol-lyase screened by the GESS system was 0.2% (2/1000 clones) which was similar to the estimated value.

Thus, the use of the GESS system according to the present invention allowed high-sensitivity screening of tyrosine phenol-lyase of single copy cloned into the fosmid vector. The probability of active clone hits was not lower than the estimated probability, suggesting that the GESS technology according to the present invention can be effectively used to screen useful foreign genes.

Example 9: Construction of Metagenomic Library from Oil-Contaminated Soil

Figure 22A:
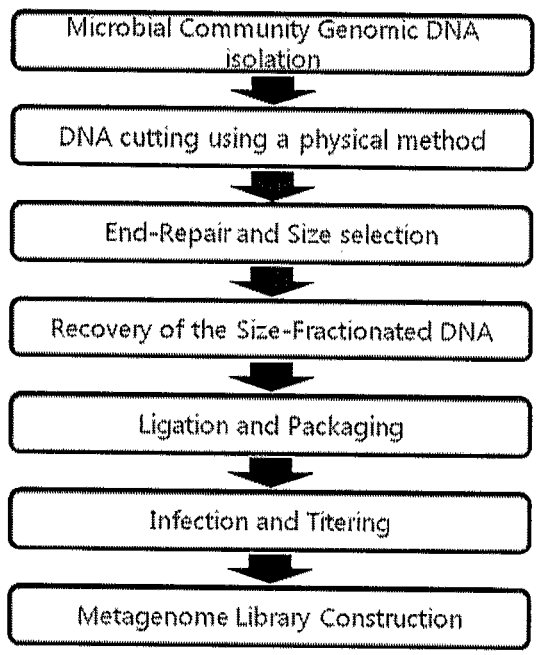
FIG. 22A shows a method of constructing a metagenomic library by extracting DNA from a microbial community.

To construct a metagenomic library, a microbial community (accession number: KCTC 11077BP) from oil-contaminated soil was obtained from the Korean Collection for Type Culture, the Korea Research Institute of Bioscience and Biotechnology. Total genomic DNA was isolated from the microbial community and cut to suitable sizes using a physical method. The sizes of the cut genomic DNA fragments were examined using 0.4% agarose gel, and as a result, it was found that the genomic DNA fragments had various sizes. The genomic DNA fragments were blunt-ended using an end-repair enzyme mix and electrophoresed, and about 30-kb end-repaired DNA was recovered from the gel and used as a DNA fragment to construct a metagenomic library. About 30 kb DNA fragment was ligated with a pCC1FOS vector (Epicentre, USA), and then packaged with fosmid clones using a packaging extract. The phage packaged with the fosmid clones was mixed with E. coli EPI300 (Epicentre, USA) and then allowed to stand at 37° C. for 45 minutes, thereby inducing the infection of the phage. The phage was plated on LB medium (10 g tryptone, 5 g yeast extract, 10 g NaCl, 1.5 g agar) containing 12.5 μg/ml of chloramphenicol and was then sufficiently cultured at 37° C. for 30-40 hours. The bacterial cells were counted, and the total size of the library was calculated. The diversity of the obtained metagenomic library was about $8 \times 10^4$ (see FIG. 22A).

The total size of the metagenomic library obtained according to the above method was about 400 Mb. Thus, when the average genomic size of each microbial strain is assumed to be about 4 Mb, the metagenomic library was determined to have information of about 100 or more genomes.

Figure 22B:
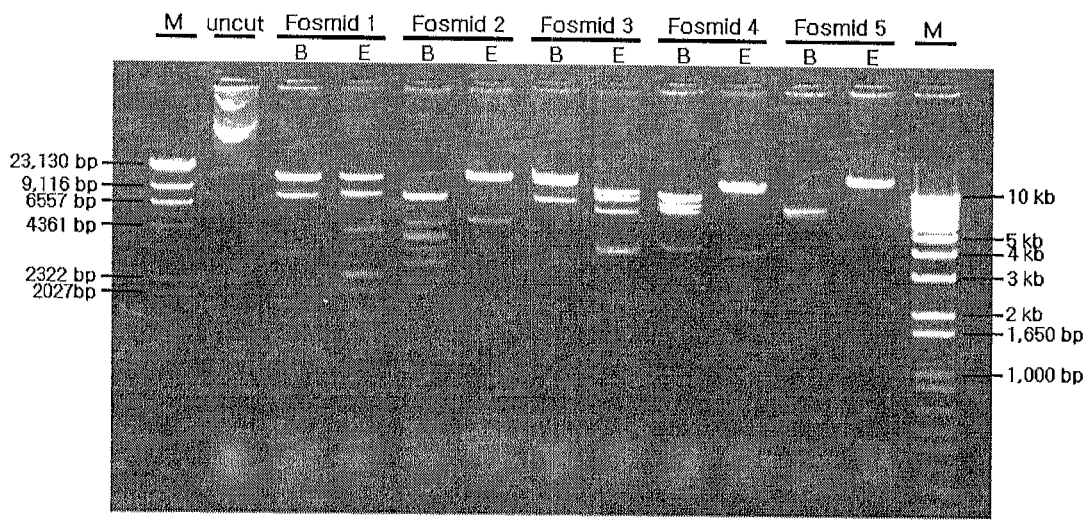
FIG. 22B shows an image of identifying the size of a gene inserted in the fosmid vector by treating the metagenomic library with restriction enzymes.

To confirm the total metagenomic library, five single bacterial strains were cultured with shaking in LB liquid medium (per liter, 10 g tryptone, 5 g yeast extract, 10 g NaCl) containing 12.5 μg/ml of chloramphenicol and 1× Copy-control solution (Epicentre, USA) for 5 hours, DNA was isolated therefrom and completely digested with BamH I and EcoR I, and DNA fragments introduced into the fosmid vectors were confirmed. The sizes of the DNA fragments were summed and the sizes of the fosmid vectors were subtracted. As a result, the size of the DNA fragments introduced into the fosmid vectors was about 27-35 kb, and the average size was about 30 kb (see FIG. 22B).

Figure 23:
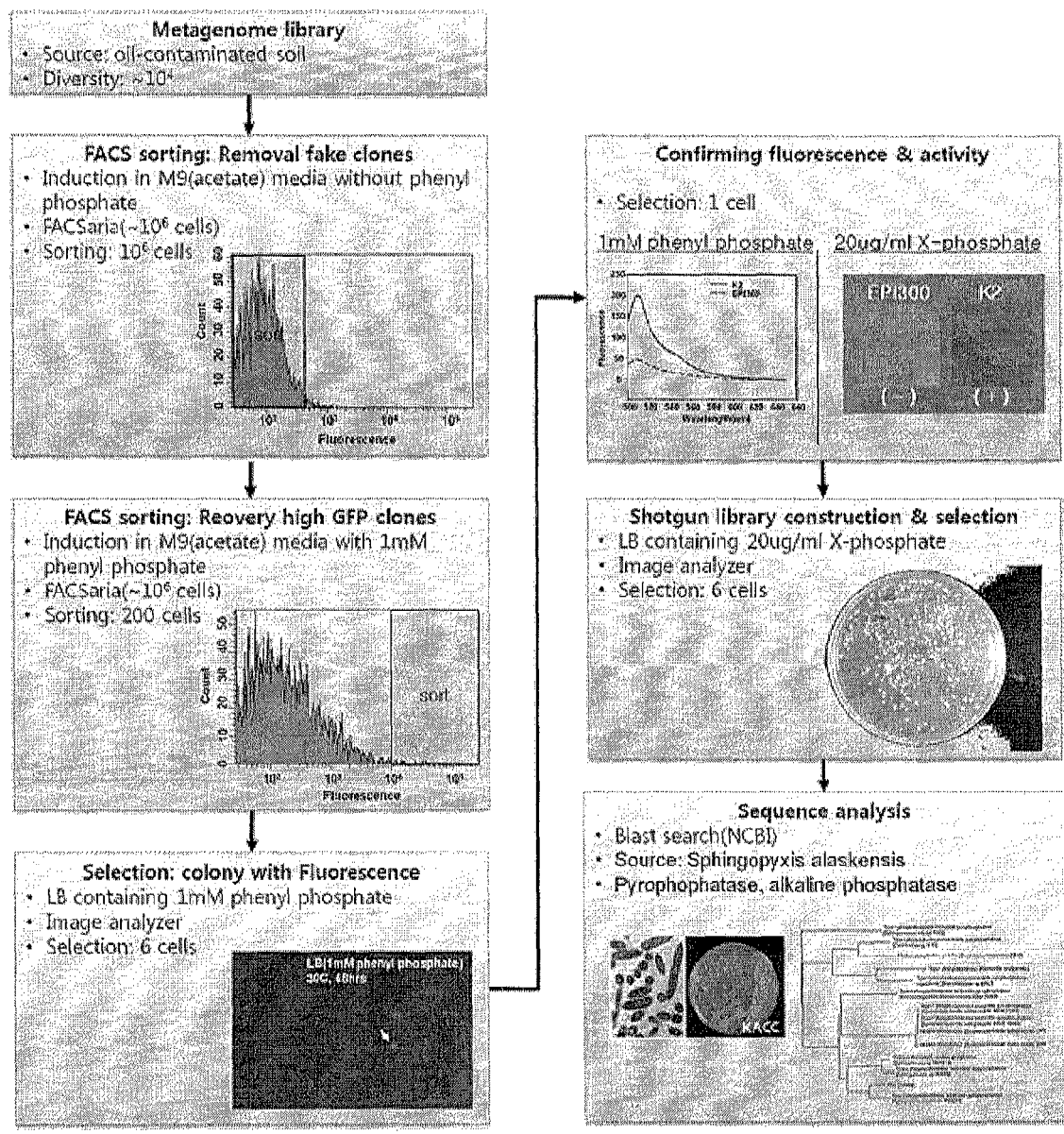
FIG. 23 shows a process of performing high-throughput screening of alkaline phosphatase from a metagenomic library using the GESS system.

Example 10: High-Throughput Screening of Alkaline Phosphatase from Environmental Metagenome pGESS-GFP$_{UV}$(I) constructed in Example 1 was introduced into the metagenomic library, constructed in Example 9, by electroporation, and the high-throughput screening of phosphatase using the GESS system was attempted (see FIG. 23).

The metagenomic library introduced with pGESS-GFP$_{UV}$ (I) was concentrated to a concentration of about $10^{10}$ cells/ml in storage buffer (per liter, 1×TY medium (8 g tryptone, 5 g yeast extract, 2.5 g NaCl), 15% (v/v) glycerol, 2% (v/v) glucose), and 0.5 ml was dispensed into each of 1.5 ml tubes and stored in a deep freezer.

The metagenomic library introduced with pGESS-GFP$_{UV}$ (I), stored in the deep freezer, was inoculated into 10 ml of LB medium at a concentration of 1% (v/v) (about $10^8$ cells) and cultured at 37° C. for 12 hours, thereby preparing a healthy library. The culture was inoculated into 2 ml of LB medium at a concentration of 1% (v/v) and cultured at 37° C. until the cell concentration (OD$_{600}$/ml) reached about 2.5-3 (about 5-6 hours). Then, the library was recovered by centrifugation (4000 rpm, 10 min). The library was washed with M9 medium (per liter, 12.8 g Na$_2$HPO$_4$.7H$_2$O, 3 g KH$_2$PO$_4$, 0.5 g NaCl, 1 g NH$_4$Cl, 2 mM MgSO$_4$, 0.1 mM CaCl$_2$, 0.4% (w/v) Glucose, 0.01% (w/v) thiamine) after centrifugation (4000 rpm, 10 min) and suspension. Then, in order to remove false positives clones showing fluorescence even in the absence of a substrate, the library was suspended in M9 media containing no phenyl phosphate and shaken at 30° C. for 16 hours. Each medium was supplemented with 1× Copy-control solution and 50 μg/ml of ampicillin and 12.5 μg/ml of chloramphenicol as selective markers. After shaking, $10^6$ non-fluorescent cells excluding false positive clones (fluorescent clones) were recovered using a fluorescence-activated cell sorting (FACS) (FACSaria, BD, USA, 407 nm violet laser, BP Filter 530/30), and they were inoculated into LB medium and cultured at 37° C. for 12 hours or more.

Next, an experiment was carried out to screen candidates showing fluorescence by the substrate phenyl phosphate. Specifically, the recovered bacterial cells were inoculated into 2 ml of LB medium to a concentration of 1% (v/v) and cultured at 37° C. until the cell concentration (OD$_{600}$/ml) reached about 2.5-3 (for about 5-6 hours), after which the library was recovered by centrifugation (4000 rpm, 10 min). The library was washed with M9 medium after centrifugation (4000 rpm, 10 min) and suspension.

Then, the library was suspended into M9 media containing 1 mM phenyl phosphate and was shaken at 30° C. to 16 hours, thereby performing an enzymatic reaction in cells. Each medium was supplemented with 1× Copy-control solution and 50 μg/ml of ampicillin and 12.5 μg/ml of chloramphenicol as selective markers. After the enzymatic reaction, the fluorescence pattern of the fluorescent library was analyzed by FACS, and 200 colonies showing strong fluorescence were recovered.

Then, the recovered colonies were plated on solid media supplemented with a substrate, and colonies showing strong fluorescence were selected. Specifically, the cells recovered by FACS were plated on LB solid media containing 1 mM phenyl phosphate and were cultured at 30° C. for 48 hours to induce the sufficient expression of fluorescence. In order to increase the expression level of the metagenomic library introduced into the fosmid vector, the medium was supplemented with 1× Copy-control solution and 50 μg/ml of ampicillin and 12.5 μg/ml of chloramphenicol as selection markers. The fluorescent colonies were observed using an image analyzer (Gel Doc 2000 gel documentation system, Bio Rad, USA), and image analysis was performed using an image analysis program (Quantity One, Bio Rad, USA). As a result, 47 colonies were produced, and among them, 6 colonies estimated to express strong fluorescence were selected.

In order to verify the enzymatic activity of the isolated clones, 5-bromo-4-chloro-3-indolyl phosphate (BCIP) was used as a color development substrate. This substrate has the same chromogen as that of X-gal which is frequently used in molecular biological studies, and it can recognize phosphatase activity by color development. The selected clones were streaked on LB solid media supplemented with 20 μg/ml of BCIP and were cultured at 30° C. overnight. Whether the clones developed color was examined, and as a result, one clone developing color was selected.

The selected clone was cultured in LB medium and subjected to the same enzymatic reaction as above, and the fluorescence spectrum thereof was analyzed. For fluorescence analysis, the cells subjected to the enzymatic reaction were recovered by centrifugation (4000 rpm, 10 min) and washed once with PBS buffer, after which CelLytic B (Sigma, USA), 20 μg/ml lysozyme (Sigma, USA) and DNAase I (Roche, Swiss) were added thereto to lyse the cell wall. The cell debris was settled by centrifugation (15000 rpm, 15 min), and the supernatant was collected and the fluorescence spectrum (excitation 385 nm) thereof was analyzed by a fluorescence analyzer (Fluorometer, varian, Australia). As a result, the emission of fluorescence at 510 nm was observed, and this fluorescence was stronger than that in the control group having the genetic circuit alone.

Example 11: Recovery and Isolation of Alkaline Phosphatase

DNA was extracted from the alkaline phosphatase-containing fosmid clone selected in Example 10, after which it was digested with Not I restriction enzyme and subjected to pulse-field gel electrophoresis (PFGE). As a result, it was found that about 37-40 kb gene was inserted in the fosmid vector.

Specifically, the fosmid clone was inoculated into LB medium containing 50 μg/ml of ampicillin and it was confirmed that pGESS-GFP$_{UV}$(I) did not exist in the clone. Then, the selected E. coli EPI300 containing alkaline phosphatase was inoculated into 100 ml of LB liquid medium supplemented with 1× Copy-control solution and was cultured at 37° C. for 5 hours. Then, the cultured clone was recovered, and DNA was isolated from the recovered clone using midi-prep kit (Qiagen, USA). The isolated DNA was digested with Not I restriction enzyme and subjected to PFGE, after which 37-40 kb gene excluding the fosmid vector was isolated therefrom. Then, the gene was cut using a DNA cutter (Hydroshear, Gene Machines, USA) to obtain an about 3-7 kb DNA fragment. The DNA fragment was recovered and phosphorylated. A pSTV28 (Takara, Japan) plasmid vector digested with BamH I was ligated with the phosphorylated DNA and then inserted into E. coli DH10B (Takara, Japan) by electroporation, thereby constructing a shotgun library. The diversity of the library was about $4\times10^4$. Based on the fact that the size of the gene introduced into the fosmid vector was about 40 kb, it was concluded that the library contained the full length of the internal gene of the fosmid clone. The shotgun library was introduced into E. coli DH5α containing pGESS-GFP$_{UV}$ (I), and 6 clones having phosphatase activity were finally selected by a combination of the screening method employing the recombinant genetic circuit (pGESS-GFP$_{UV}$ (I)) and a color development substrate (BCIP) method.

Figure 24:
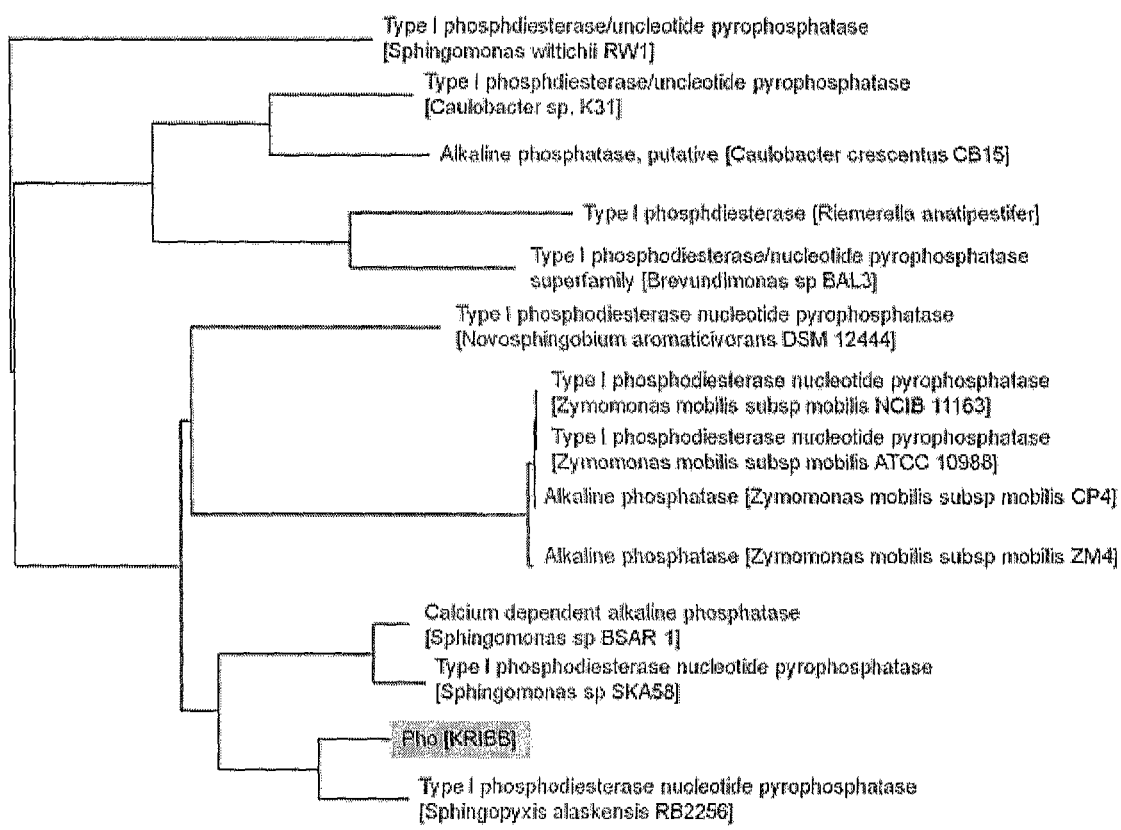
FIG. 24 is a distance tree showing highly homologous sequences after blast searching based on the amino acid sequence of novel alkaline phosphatase (Pho [KRIBB]: novel alkaline phosphatase screened according to the present invention).

Example 12: Comparison of Base Sequence and Identity of Alkaline Phosphatase The 6 clones showing alkaline phosphatase activity were subjected to base sequence analysis. As a result, the sizes of genes in the clones were about 2.2-5.4 kb, in which 2 of the 6 clones were identical, and the about 3 kb clones contained the full-length of the largest gene of 5,428 bp. The largest clone was sequenced (http://blast.ncbi.nlm.nih.gov), and as a result, it show high identity with about 5 kb sequences including nucleotide pyrophosphatase in the genome of Sphingopyxis alaskensis RB2256 and showed an identity (=1455/1835 (79%)) of about 79% with nucleotide pyrophosphatase. When the size of pyrophosphatase was estimated, it could be seen that the alkaline phosphatase had a length of 1,824 bp (SEQ ID NO: 2) and consisted of 607 amino acids (SEQ ID NO: 1). In the present invention, the protein was named "alkaline phosphatase Pho". In addition, the protein was BLAST searched based on the amino acid sequence thereof, and the identity thereof was analyzed by the distance tree. As a result, the protein showed high identity with phosphodiesterase and alkaline phosphatase (see FIG. 24).

For reference, Sphingopyxis alaskensis RB2256 is a strain of psychrophilic (4 to 10° C.) microorganisms which are distributed in the Alaska's deep sea, exist in the North Sea and the North Pacific in large amounts and are widely found in land in addition to the sea. In order for the microbial strain to grow in deep waters lacking nutrients, it should be able to effectively absorb fine concentrations of nutrients. For this purpose, Sphingopyxis alaskensis has a fine body size (0.1 μm$^3$ or less) having a large surface area per volume, has high affinity for micronutrients, and can use various nutrients. Thus, the strain is receiving attention in cell biology.

Example 13: Analysis of Enzymatic Properties of Novel Alkaline Phosphatase

The optimum pH and temperature, thermal stability and substrate specificity of the selected alkaline phosphatase and the effect thereof on metal ions were examined. An enzymatic reaction was performed in the following manner. The enzymatic reaction was performed using a mixture of 50 mM diethanolamine, DEA (pH 9.0) buffer, 0.5 mM para-nitrophenylphosphate (pNPP) and the enzyme at 37° C. for 5 minutes. The same amount of 1M NaOH was added to stop the enzymatic reaction, and the amount of nitrophenol produced by the enzymatic reaction was measured. the measurement was performed by measuring the absorbance at 405 nm using a fluorescence plate reader (Victor5, Perkin-Elmer, USA). 1 unit was defined as the amount of enzyme that can produce 1 μmol of para-nitrophenol per minute at 37° C.

(1) Examination of Properties at Various pHs and Temperatures

Figure 25A:
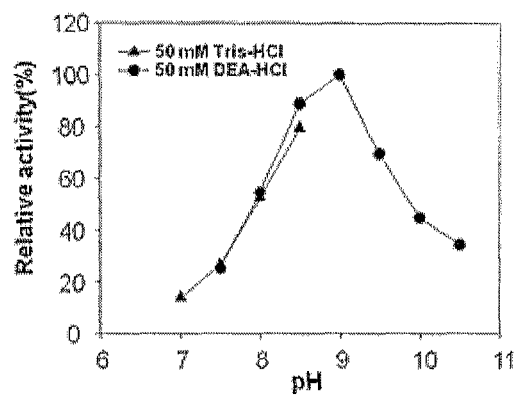
FIG. 25A is an image showing the optimum pH indicating the highest activity.

In order to examine the optimum pH of the novel alkaline phosphatase, the activities thereof at a pH of 7.0 to 10.5 were compared. At a pH of 7.0 to 8.5, 50 mM Tris-HCl buffer was used, and at a pH of 7.5 to 10.5, 50 mM DEA buffer was used. As a result, the alkaline phosphatase showed the highest activity at a pH of 9.0 (see FIG. 25A).

Figure 25B:
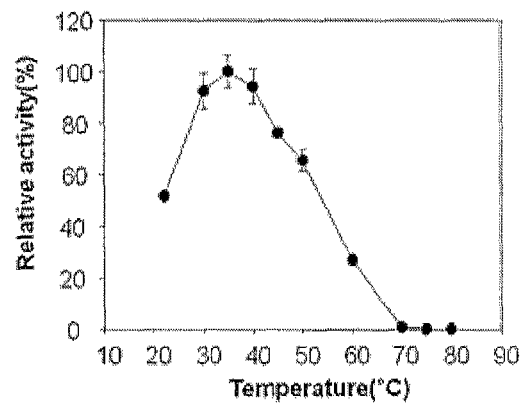
FIG. 25B is an image showing the optimum temperature indicating the highest activity.
Figure 25C:
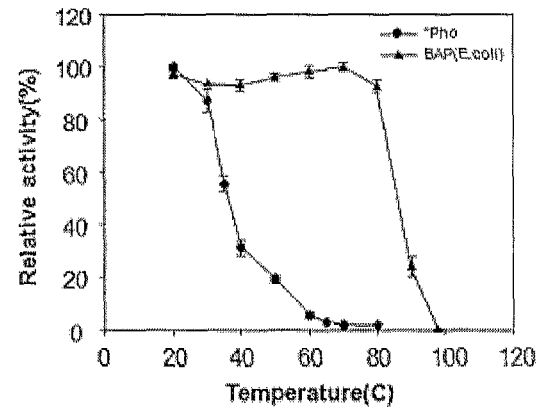
FIG. 25C shows the degrees of thermal inactivation of enzymes.

In addition, the activities of the enzyme at various temperatures were compared. As a result, the enzyme showed the optimum activity at 35° C. (see FIG. 25B). In addition, in order to examine the thermal inactivation of the enzyme, the enzyme was allowed to stand at various temperatures for 15 minutes, and then the remaining enzymatic activity was measured. As a result, the activity of the enzyme decreased rapidly as the temperature increased, and at 65° C., only an enzymatic activity of about 3% or less remained. However, alkaline phosphatase (BAP) from E. coli had high thermal stability, so that the activity thereof was not inactivated at 80° C. or below (see FIG. 25C).

INDUSTRIAL APPLICABILITY

As described above, when the inventive method for screening and quantifying target enzymatic activity is used, useful genes can be screened from various genetic communities, including environmental or metagenomic libraries. Further, the sensitivity of the genetic circuit to phenol derivatives and the expression thereof can be controlled, and thus the genetic circuit can rapidly sense and quantify various enzymatic activities. Thus, the invention can be advantageously used in the protein engineering technology for enzyme modification. Particularly, it can quantitatively investigate enzymatic activity, and thus can be applied to molecular evolution technology.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method of detecting, screening, or quantifying the activity of one or more biosynthesis enzymes performing enzymatic reactions using compounds having a phenol group bound thereto as substrates, using an artificial genetic circuit, the method comprising the steps of:
   (a) providing an artificial genetic circuit for detecting said phenolic compound or microorganisms containing in their chromosomal DNA or cytoplasm an artificial genetic circuit for detecting said phenolic compound, the artificial genetic circuit comprising:
   (i) a gene encoding a transcriptional regulator to which said phenolic compound binds,
   (ii) at least one reporter gene selected from the group consisting of fluorescence protein-encoding genes and antibiotic resistance genes, and
   (iii) a gene expression regulatory region consisting of a promoter regulating the expression of said transcriptional regulator,
   a promoter regulating the expression of the reporter gene, and
   a region, located between the promoter regulating the expression of the reporter gene and reporter gene, to which said transcriptional regulator binds to induce the expression of a downstream reporter gene,
   wherein the phenolic compound binds to (i) transcriptional regulator to induce binding of the transcriptional regulator to the (iii) gene expression regulatory region and activate the promoter of the reporter gene such that the reporter gene located downstream of the gene expression regulatory region is expressed;
   (b) providing a clone or gene library containing one or more of a gene encoding a biosynthesis enzyme for said phenolic compound;
   (c) introducing the clone or gene library and the artificial gene circuit for detecting said phenolic compound into host microorganisms to prepare recombinant microorganisms or introducing the clone or gene library into the microorganisms containing the artificial gene circuit for detecting said phenolic compound to prepare recombinant microorganisms;
   (d) treating the recombinant microorganisms with a compound capable of liberating said phenolic compound by an enzymatic reaction of the biosynthesis enzyme for production of phenolic compound that is to be detected, screened, or quantified; and
   (e) detecting or quantifying the activity of the reporter protein whose expression was induced by sensing said phenolic compound liberated by the enzymatic reaction of the biosynthesis enzyme for production of phenolic compound that is to be detected, screened, or quantified.

2. A method of screening target enzyme activity of one or more biosynthesis enzymes performing enzymatic reactions using compounds having a phenol group bound thereto as substrates, using an artificial genetic circuit, the method comprising the steps of:
   (a) providing microorganisms containing in their chromosomal DNA or cytoplasm an artificial genetic circuit for detecting the phenolic compound, the artificial genetic circuit comprising
   (i) a gene encoding a transcriptional regulator to which the phenolic compound binds,
   (ii) at least one reporter gene selected from the group consisting of fluorescence protein-encoding genes and antibiotic resistance genes, and
   (iii) a gene expression regulatory region consisting of a promoter regulating the expression of the transcriptional regulator, a promoter regulating the expression of the reporter gene, and a region, located between the promoter regulating the expression of the reporter gene and reporter gene, to which said transcriptional regulator binds to induce the expression of a downstream reporter gene, wherein the phenolic compound binds to (i) transcriptional regulator to induce binding of the transcriptional regulator to the (iii) gene expression regulatory region and activate the promoter of the reporter gene such that the reporter gene located downstream of the gene expression regulatory region is expressed;

(b) providing a clone or gene library containing one or more of a gene encoding a biosynthesis enzyme for the production of phenolic compound;

(c) introducing the clone or gene library into microorganisms containing the artificial gene circuit for detecting the phenolic compound to prepare recombinant microorganisms or introducing the clone or gene library into the microorganisms containing the artificial gene circuit for detecting said phenolic compound to prepare recombinant microorganisms;

(d) treating the recombinant microorganisms with a compound capable of liberating the phenolic compound by an enzymatic reaction of the biosynthesis enzyme for the production of phenolic compound that is to be detected, screened, or quantified; and (e) detecting the activity of the reporter protein whose expression was induced by sensing the phenolic compound liberated by the enzymatic reaction of the biosynthesis enzyme for the production of phenolic compound that is to be detected, screened, or quantified.

3. A method of quantifying target enzyme activity of one or more biosynthesis enzymes performing enzymatic reactions using compounds having a phenol group bound thereto as substrates using an artificial genetic circuit, the method comprising the steps of:

(a) providing an artificial genetic circuit for detecting the phenolic compound or microorganisms containing in their chromosomal DNA or cytoplasm an artificial genetic circuit for detecting the phenolic compound, the artificial genetic circuit comprising (i) a gene encoding a transcriptional regulator to which the phenolic compound binds, (ii) at least one reporter gene selected from the group consisting of fluorescence protein-encoding genes and antibiotic resistance genes, and (iii) a gene expression regulatory region consisting of a promoter regulating the expression of the transcriptional regulator, a promoter regulating the expression of the reporter gene, and a region, located between the promoter regulating the expression of the reporter gene and reporter gene, to which said transcriptional regulator binds to induce the expression of a downstream reporter gene, wherein the phenolic compound binds to (i) transcriptional regulator to induce binding of the transcriptional regulator to the (iii) gene expression regulatory region and activate the promoter of the reporter gene such that the reporter gene located downstream of the gene expression regulatory region is expressed;

(b) providing a clone or gene library containing one or more of a gene encoding a biosynthesis enzyme for the production of phenolic compound;

(c) introducing the clone or gene library and the artificial gene circuit for detecting the phenolic compound into host microorganisms to prepare recombinant microorganisms or introducing the clone or gene library into the microorganisms containing the artificial gene circuit for detecting the phenolic compound to prepare recombinant microorganisms;

(d) treating the recombinant microorganisms with a compound capable of liberating the phenolic compound by an enzymatic reaction of the biosynthesis enzyme for the production of phenolic compound that is to be detected, screened, or quantified; and (e) quantifying the activity of the reporter protein whose expression was induced by sensing the phenolic compound liberated by the enzymatic reaction of the biosynthesis enzyme for the production of phenolic compound that is to be detected, screened, or quantified.

4. A method of quantifying target enzyme activity of one or more biosynthesis enzymes performing enzymatic reactions using compounds having a phenol group bound thereto as substrates, using an artificial genetic circuit, the method comprising the steps of:

(a) providing microorganisms containing in their chromosomal DNA or cytoplasm an artificial genetic circuit for detecting the phenolic compound, the artificial genetic circuit comprising (i) a gene encoding a transcriptional regulator to which the phenolic compound binds, (ii) at least one reporter gene selected from the group consisting of fluorescence protein-encoding genes and antibiotic resistance genes, and (iii) a gene expression regulatory region consisting of a promoter regulating the expression of the transcriptional regulator, a promoter regulating the expression of the reporter gene, and a region, located between the promoter regulating the expression of the reporter gene and reporter gene, to which said transcriptional regulator binds to induce the expression of a downstream reporter gene, wherein the phenolic compound binds to (i) transcriptional regulator to induce binding of the transcriptional regulator to the (iii) gene expression regulatory region and activate the promoter of the reporter gene such that the reporter gene located downstream of the gene expression regulatory region is expressed;

(b) providing a clone or gene library containing one or more of a gene encoding a phenolic compound biosynthesis enzyme for the production of phenolic compound;

(c) introducing the clone or gene library into microorganisms containing the artificial gene circuit for detecting the phenolic compound to prepare recombinant microorganisms;

(d) treating the recombinant microorganisms with a compound capable of liberating the phenolic compound by an enzymatic reaction of the biosynthesis enzyme for the production of phenolic compound that is to be detected, screened, or quantified; and (e) quantifying the activity of the reporter protein whose expression was induced by sensing the phenolic compound liberated by the enzymatic reaction of the biosynthesis enzyme for the production of phenolic compound that is to be detected, screened, or quantified.

5. A method of screening a target enzyme capable of liberating a phenolic compound by the reaction of an enzyme from a metagenomic library, the method comprising the steps of:

(a) providing a metagenomic library from a natural environment;

(b) providing an artificial genetic circuit for detecting the phenolic compound, the artificial genetic circuit comprising (i) a gene encoding a transcriptional regulator to which the phenolic compound binds, (ii) at least one reporter gene selected from the group consisting of fluorescence protein-encoding genes and antibiotic resistance genes, and (iii) a gene expression regulatory region consisting of a promoter regulating the expression of the phenolic compound-sensing transcriptional regulator, a promoter regulating the expression of the reporter gene, and a region, located between the promoter regulating the expression of the reporter gene and reporter gene, to which said transcriptional regulator binds to induce the expression of a downstream reporter gene, wherein the phenolic compound binds to (i) transcriptional regulator to induce binding of the transcriptional regulator to the (iii) gene expression regulatory region and activate the promoter of the reporter gene such that the reporter gene located downstream of the gene expression regulatory region is expressed;

(c) introducing the metagenomic library and the artificial genetic circuit into host microorganisms to construct a library of transformed microorganisms or introducing the metagenomic library into the microorganisms containing the artificial gene circuit to construct a library of transformed organisms;

(d) treating the library of transformed microorganisms with a compound capable of liberating the phenolic compound by an enzymatic reaction of the biosynthesis enzyme for the production of phenolic compound that is to be detected, screened, or quantified;

(e) measuring the activity of the reporter protein whose expression was induced by sensing the phenolic compound liberated by the enzymatic reaction, thereby performing high-throughput screening of microorganisms having activity of liberating the phenolic compound by the enzymatic reaction of the biosynthesis enzyme for the production of phenolic compound that is to be detected, screened, or quantified; and (f) collecting a gene of the enzyme, which is capable of liberating the phenolic compound by an enzymatic reaction, from the screened microorganisms, and then identifying the gene by sequencing.

6. A method of screening a target enzyme capable of liberating a phenolic compound by the reaction of an enzyme from a metagenomic library, the method comprising the steps of:

(a) providing a metagenomic library from a natural environment;

(b) providing microorganisms containing in their chromosomal DNA or cytoplasm an artificial genetic circuit for detecting the phenolic compound, the artificial genetic circuit comprising (i) a gene encoding a transcriptional regulator to which the phenolic compound binds, (ii) at least one reporter gene selected from the group consisting of fluorescence protein-encoding genes and antibiotic resistance genes, and (iii) a gene expression regulatory region consisting of a promoter regulating the expression of the transcriptional regulator, a promoter regulating the expression of the reporter gene, and a region, located between the promoter regulating the expression of the reporter gene and reporter gene, to which said transcriptional regulator binds to induce the expression of a downstream reporter gene, wherein the phenolic compound binds to (i) transcriptional regulator to induce binding of the transcriptional regulator to the (iii) gene expression regulatory region and activate the promoter of the reporter gene such that the reporter gene located downstream of the gene expression regulatory region is expressed;

(c) introducing the metagenomic library into the microorganisms containing in their chromosomal DNA or cytoplasm the artificial genetic circuit to construct a library of transformed microorganisms;

(d) treating the library of transformed microorganisms with a compound capable of liberating the phenolic compound by an enzymatic reaction;

(e) measuring the activity of the reporter protein whose expression was induced by sensing the phenolic compound liberated by the enzymatic reaction, thereby performing high-throughput screening of microorganisms having activity of liberating the phenolic compound by the enzymatic reaction of the biosynthesis enzyme for the production of phenolic compound that is to be detected, screened, or quantified; and (f) collecting a gene of the enzyme, which is capable of liberating the phenolic compound by the enzymatic reaction of the biosynthesis enzyme for the production of phenolic compound that is to be detected, screened, or quantified, from the screened microorganisms, and then identifying the gene by sequencing.

7. The method of claim 1, wherein the reporter gene and the promoter regulating the expression of the reporter gene are operably linked to each other.

8. The method of claim 1, wherein the gene encoding the transcriptional regulator to which the phenolic compound binds and the promoter regulating the expression of the transcriptional regulator are operably linked to each other.

9. The method of claim 1, wherein the enzymes is selected from the group consisting of alpha-glucosidase, beta-glucosidase, cellulase, glycosylceramidase, phosphatase, phytase, esterase, lipase, urethanase, amidase, peptidase, proteinase, oxydoreductase, phenol-lyase, dihalogenase, isomerase, monooxyenase, and dioxygenase.

10. The method of claim 1, wherein the compound capable of liberating the phenolic compound by an enzymatic reaction is a compound selected from the group consisting of phenol, o-chlorophenol, m-chlorophenol, p-chlorophenol, o-nitrophenol, m-nitrophenol, p-nitrophenol, salicylic acid, 2-aminophenol, 2-methoxyphenol, catechol, resorcinol, 3-methylcatechol, 2,4-dimethylphenol, 2,5-dimethylphenol, 3,4-dimethylphenol, 2,3-dimethylphenol, 3,5-dimethylphenol, 2,4-dichlorophenol, 2,5-dichlorophenol, 2,3-dichlorophenol, 2,6-dichlorophenol, 3,4-dichlorophenol, 3,5-dichlorophenol, 2,4-dinitrophenol, o-cresol, m-cresol, p-cresol, 2-ethylphenol, 3-ethylphenol, 2-fluorophenol, 2-iodophenol, and benzene.

11. The method of claim 1, wherein the compound capable of liberating the phenolic compound by an enzymatic reaction is selected from the group consisting of phenolic compounds containing ester, glycoside or phosphoester, which substitutes for the hydroxyl group (—OH) of phenol; phenol derivatives containing an alkyl, hydroxyl, carboxyl, amino, thiol, amide, sulfide or halogen group at the ortho-, meta- or para-position; and benzene ring compounds.

12. The method of claim 1, wherein the transcriptional regulator to which the phenolic compound binds is DmpR or its variant.

13. The method of claim 1, wherein the fluorescence protein is selected from the group consisting of GFP, $GFP_{UV}$ and RFP.

14. The method of claim 1, wherein the antibiotic resistance gene is selected from the group consisting of kanamycin, chloramphenicol and tetracycline.

15. The method of claim 1, wherein detecting or quantifying the activity of the reporter protein is performed by using a method selected from the group consisting of microcolony-fluorescence image analysis, fluorescence spectrum analysis, fluorescence-activated cell sorting (FACS), and antibiotic resistance measuring method.

16. The method of claim 1, wherein the microorganism is selected from the group consisting of *E. coli*, yeast, a plant cell or an animal cell.

17. The method of claim 1, wherein *E. coli* RBS sequence is inserted into the artificial genetic circuit to facilitate the expression of the reporter gene in *E. coli*.

18. The method of claim 1, wherein the reporter gene is a dual reporter consisting of both a fluorescence protein and an antibiotic resistance gene.

19. The method of claim 5, wherein the metagenomic library is constructed by introducing soil-derived DNA into a vector selected from the group consisting of plasmids, fosmids, cosmids, BAC and YAC.

20. The method of claim 5, wherein the step of collecting the gene of the enzyme is performed by treatment of restriction enzyme.

21. The method of claim 5, wherein the genetic circuit further contains a suicide gene sacB.

22. The method of claim 5, wherein the treatment of the library of transformed microorganisms with the compound capable of liberating the phenolic compound by the enzymatic reaction is performed when the cell growth value ($OD_{600}$/ml) of the transformed microorganisms reached about 1.5-4.

23. The method of claim 5, wherein the enzymatic reaction is performed during 14~16 hours after the treatment of the library of transformed organisms with the compound capable of liberating the phenolic compound by the enzymatic reaction.

24. The method of claim 5, wherein the step of treatment of the library of transformed microorganisms with the compound capable of liberating the phenolic compound by the enzymatic reaction comprises the steps of: (i) collecting a microorganism grown in nutrient medium; and (ii) treating the collected microorganism with the compound in minimal medium.

* * * * *

SEQUENCE LISTING

<160> NUMBER OF SEQ ID NOS: 21

<210> SEQ ID NO 1
<211> LENGTH: 27
<212> TYPE: DNA
<213> ORGANISM: Artificial
<220> FEATURE:
<223> OTHER INFORMATION: primer

<400> SEQUENCE: 1
ccggaattcg agctgatcga aagtcgg                                          27

<210> SEQ ID NO 2
<211> LENGTH: 27
<212> TYPE: DNA
<213> ORGANISM: Artificial
<220> FEATURE:
<223> OTHER INFORMATION: primer

<400> SEQUENCE: 2
ccggaattcc tagccttcga tgccgat                                          27

<210> SEQ ID NO 3
<211> LENGTH: 80
<212> TYPE: DNA
<213> ORGANISM: Artificial
<220> FEATURE:
<223> OTHER INFORMATION: primer

<400> SEQUENCE: 3
gcacagctgt tgcactttgt cctgcgcaat ccgccaacct ggagaaggag atatacatat      60
ggtgagcaag ggcgaggagc                                                  80

<210> SEQ ID NO 4
<211> LENGTH: 71
<212> TYPE: DNA
<213> ORGANISM: Artificial
<220> FEATURE:
<223> OTHER INFORMATION: primer

<400> SEQUENCE: 4
gatttaatct gtatcaggct gaaaatcttc tctcatccgc caaaacagaa gcttacttgt      60
acagcttgtc c                                                           71

<210> SEQ ID NO 5
<211> LENGTH: 48
<212> TYPE: DNA
<213> ORGANISM: Artificial
<220> FEATURE:
<223> OTHER INFORMATION: primer

<400> SEQUENCE: 5
atggacaagc tgtacaagta agcttctgtt ttggcggatg agagaaga                   48

<210> SEQ ID NO 6
<211> LENGTH: 72
<212> TYPE: DNA
<213> ORGANISM: Artificial
<220> FEATURE:
<223> OTHER INFORMATION: primer

<400> SEQUENCE: 6
agcggataac aatttcacac agaaacagct atgaccatga ttacgccaag agtttgtaga      60
aacgcaaaaa gg                                                          72

```
<210> SEQ ID NO 7
<211> LENGTH: 46
<212> TYPE: DNA
<213> ORGANISM: Artificial
<220> FEATURE:
<223> OTHER INFORMATION: primer

<400> SEQUENCE: 7
tctctcatcc gccaaaacag gaattcctag ccttcgatgc cgattt          46

<210> SEQ ID NO 8
<211> LENGTH: 48
<212> TYPE: DNA
<213> ORGANISM: Artificial
<220> FEATURE:
<223> OTHER INFORMATION: primer

<400> SEQUENCE: 8
tcttctctca tccgccaaaa cagaagctta cttgtacagc ttgtccat        48

<210> SEQ ID NO 9
<211> LENGTH: 29
<212> TYPE: DNA
<213> ORGANISM: Artificial
<220> FEATURE:
<223> OTHER INFORMATION: primer

<400> SEQUENCE: 9
cccgaattct tcttcgtctg tttctactg                             29

<210> SEQ ID NO 10
<211> LENGTH: 30
<212> TYPE: DNA
<213> ORGANISM: Artificial
<220> FEATURE:
<223> OTHER INFORMATION: primer

<400> SEQUENCE: 10
cccgaattca atggcgatga cgcatcctca                            30

<210> SEQ ID NO 11
<211> LENGTH: 70
<212> TYPE: DNA
<213> ORGANISM: Artificial
<220> FEATURE:
<223> OTHER INFORMATION: primer

<400> SEQUENCE: 11
cggataacaa tttcacacag gaaacagcta tgaccatgat tacgccaagc ttatttgtag   60
agctcatcca                                                          70

<210> SEQ ID NO 12
<211> LENGTH: 70
<212> TYPE: DNA
<213> ORGANISM: Artificial
<220> FEATURE:
<223> OTHER INFORMATION: primer

<400> SEQUENCE: 12
acctggagat ggccgtgacc aatacccccca caccgacttt cgatcagctc atgagtaaag   60
gagaagaact                                                          70

<210> SEQ ID NO 13
```

```
<211> LENGTH: 70
<212> TYPE: DNA
<213> ORGANISM: Artificial
<220> FEATURE:
<223> OTHER INFORMATION: primer

<400> SEQUENCE: 13
acctggagat ggccgtgacc ataccccca caccgactttt cgatcagctc atggagaaaa    60
aaatcactgg                                                            70

<210> SEQ ID NO 14
<211> LENGTH: 70
<212> TYPE: DNA
<213> ORGANISM: Artificial
<220> FEATURE:
<223> OTHER INFORMATION: primer

<400> SEQUENCE: 14
cggataacaa tttcacacag gaaacagcta tgaccatgat tacgccaagc ttacgccccg    60
ccctgccact                                                            70

<210> SEQ ID NO 15
<211> LENGTH: 70
<212> TYPE: DNA
<213> ORGANISM: Artificial
<220> FEATURE:
<223> OTHER INFORMATION: primer

<400> SEQUENCE: 15
acctggagat ggccgtgacc ataccccca caccgactttt cgatcagctc atgaaatcta    60
acaatgcgct                                                            70

<210> SEQ ID NO 16
<211> LENGTH: 70
<212> TYPE: DNA
<213> ORGANISM: Artificial
<220> FEATURE:
<223> OTHER INFORMATION: primer

<400> SEQUENCE: 16
cggataacaa tttcacacag gaaacagcta tgaccatgat tacgccaagc tcaggtcgag    60
gtggcccggc                                                            70

<210> SEQ ID NO 17
<211> LENGTH: 70
<212> TYPE: DNA
<213> ORGANISM: Artificial
<220> FEATURE:
<223> OTHER INFORMATION: primer

<400> SEQUENCE: 17
acctggagat ggccgtgacc ataccccca caccgactttt cgatcagctc atgagccata    60
ttcaacggga                                                            70

<210> SEQ ID NO 18
<211> LENGTH: 70
<212> TYPE: DNA
<213> ORGANISM: Artificial
<220> FEATURE:
<223> OTHER INFORMATION: primer

<400> SEQUENCE: 18
cggataacaa tttcacacag gaaacagcta tgaccatgat tacgccaagc ttagaaaaac    60
```
tcatcgagca 70

<210> SEQ ID NO 19
<211> LENGTH: 40
<212> TYPE: DNA
<213> ORGANISM: Artificial
<220> FEATURE:
<223> OTHER INFORMATION: primer

<400> SEQUENCE: 19
gatcgactcc ttcgaggtga aaatctgcca gaccgacctg        40

<210> SEQ ID NO 20
<211> LENGTH: 40
<212> TYPE: DNA
<213> ORGANISM: Artificial
<220> FEATURE:
<223> OTHER INFORMATION: primer

<400> SEQUENCE: 20
caggtcggtc tggcagattt tcacctcgaa ggagtcgatc        40

<210> SEQ ID NO 21
<211> LENGTH: 2157
<212> TYPE: DNA
<213> ORGANISM: Artificial
<220> FEATURE:
<223> OTHER INFORMATION: DNA fragment consisting of dmpR gene including
      EcoRI, dmp operator-promoter, partial sequence of dmpK gene and
      restriction enzyme sequence

<400> SEQUENCE: 21
ccggaattcg agctgatcga aagtcggtgt gggggtattg gtcacggcca tctccaggtt        60
ggcggattgc gcaggacaaa gtgcaacagc tgtgccaagg tctgaaaacc gacttcaagg       120
tattgttttt caatgtgttt ctaatttta gaatgatcgg agcgagcgaa attaagccgc        180
gcttgcgcag gctttttaag catttgatca attgcccaag gccgcttgag caaatgctca      240
tggcgcagct gaaggctgat ctctagcact aaagtcactg ccgtcgattg atcatttggt      300
tgacttttgc cagatactga ggtcggctat ggggagctgg cgcaggtgaa aaaactgccg      360
attttcccca tgaccccatc tggaatcgcc gcctgccttg cgctatagcg gcgaccctga      420
tttccccatc taaaaataaa taggggcctc gcttacatgc cgatcaagta caagcctgaa      480
atccagcact ccgatttcaa ggacctgacc aacctgatcc acttccagag cacggaaggc      540
aagatctggc ttggcgaaca acgcatgctg ttgctgcagg tttcagcaat ggccagcttt      600
cgccgggaaa tggtcaatac cctgggcatc gaacgcgcca agggcttctt cctgcgccag      660
ggttaccagt ccggctgaa ggatgccgaa ctggccagga agcttagacc gaatgccagc      720
gagtacgaca tgttcctcgc cggcccgcag ctgcattcgc tcaagggtct ggtcaaggtc      780
cgccccaccg aggtcgatat cgacaaggaa tgcgggcgct tctatgccga gatggagtgg      840
atcgactcct tcgaggtgga aatctgccag accgacctgg ggcagatgca agaccgggtg      900
tgctggactc tgctcggcta cgcctgcgcc tattcctcgg cgttcatggg ccgggaaatc      960
atcttcaagg aagtcagctg ccgcggctgc ggcggcgaca gtgccgggt cattggcaag     1020 ccggccgaag agtgggacga cgttgccagc ttcaaacagt atttcaagaa cgaccccatc     1080
atcgaggaac tctacgagtt gcaatcgcaa ctggtgtcgc tgcgtaccaa cctcgacaaa     1140
caggaaggcc agtactacgg catcggtcag acccggcct accagaccgt gcgcaatatg     1200

-continued

```
atggacaagg ccgcacaggg caaagtctcg gtgctgctgc ttggcgagac cggggtcggc    1260
aaggaggtca tcgcgcgtag cgtgcacctg cgcagcaaac gcgccgccga gccctttgtc    1320
gcggtgaact gtgcggcgat cccgccggac ctgatcgagt ccgaattgtt cggcgtggaa    1380
aaaggcgcct tcaccggcgc cacccagtca cgcatgggcc gcttcgagcg ggccgacaag    1440
ggcaccatct tccttgacga ggtgatcgaa ctcagcccgc gcgctcaggc cagtttgctg    1500
cgcgtgctgc aagaaggcga gctggagcga gttggcgaca accgcacgcg caagatcgac    1560
gtaagggtta tcgcagccac ccacgaggac ctggccgaag cggtcaaggc cgggcgtttt    1620
cgcgccgacc tgtactaccg gctgaacgtt ttcccggtgg cgatcccggc gttgcgcgaa    1680
cgccgcgagg acattccact gctggttgag cacttccttc agcgcttcca ccaggagtac    1740
ggcaagagaa ccctcggcct ttcagacaaa gccctggagg cctgcctgca ttacagttgg    1800
ccgggcaata tccgtgagct ggagaacgtc atcgagcgcg gcatcatcct caccgatccg    1860
aacgaaagca tcagcgtgca ggcgctgttc ccacgggcgc cggaagagcc gcagaccgcc    1920
agcgagcggg tgtcgtcgga cggcgtgctg attcagccag gcaatggcca gggcagttgg    1980
atcagccagt tgttgagcag cggcctgagc ctcgacgaga tcgaggaaag cctgatgcgc    2040
aaagccatgc aacaggccaa ccaaaacgtc tccggtgccg cgcgcttgct cggcctaagc    2100
cgaccggcac tggcctatcg gctgaagaaa atcggcatcg aaggctagga attccgg      2157
```